(12) United States Patent
Korley et al.

(10) Patent No.: US 9,797,075 B2
(45) Date of Patent: Oct. 24, 2017

(54) POLYMER COMPOSITE AND METHOD OF FORMING SAME

(75) Inventors: LaShanda Korley, Cleveland, OH (US); David A. Stone, Pittsburgh, PA (US); Gary E. Wnek, Cleveland, OH (US); Nandula Wanasekara, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 5 days.

(21) Appl. No.: 14/125,201

(22) PCT Filed: Jun. 11, 2012

(86) PCT No.: PCT/US2012/041969
§ 371 (c)(1),
(2), (4) Date: Aug. 14, 2014

(87) PCT Pub. No.: WO2012/171040
PCT Pub. Date: Dec. 13, 2012

(65) Prior Publication Data
US 2015/0038038 A1    Feb. 5, 2015

Related U.S. Application Data

(60) Provisional application No. 61/495,942, filed on Jun. 10, 2011.

(51) Int. Cl.
*D04H 1/728* (2012.01)
*A61L 31/06* (2006.01)
(Continued)

(52) U.S. Cl.
CPC .............. *D04H 1/728* (2013.01); *A61L 31/06* (2013.01); *A61L 31/10* (2013.01); *A61L 31/16* (2013.01);
(Continued)

(58) Field of Classification Search
CPC .......... A61L 31/06; A61L 31/10; A61L 31/16; C08L 29/04; C08L 71/02; B82Y 30/00;
(Continued)

(56) References Cited

U.S. PATENT DOCUMENTS

| | | | |
|---|---|---|---|
| 6,295,167 B1 | 9/2001 | Uematsu et al. | |
| 2004/0018226 A1* | 1/2004 | Wnek .................. | A61F 2/08 424/443 |

(Continued)

OTHER PUBLICATIONS

International Search Report issued for PCT/US2012/041969 mailed on Sep. 5, 2012.
(Continued)

*Primary Examiner* — Arti Singh-Pandey
(74) *Attorney, Agent, or Firm* — Benesch, Friedlander, Coplan & Aronoff, LLP

(57) ABSTRACT

In accordance with one embodiment, a polymer composite comprises a filler and a matrix. The filler comprises an electrospun polymer mat. The matrix comprises a polymer film. The filler is arranged to respond to stimuli by altering its mechanical properties. In one example, the mat can be electrospun from poly(vinyl alcohol), and the matrix can be formed from ethylene oxide-epichlorohydrin 1:1 copolymer. The filler can be arranged so that the tensile storage modulus of the polymer composite changes in response to the filler being exposed to a stimulus. In another example, the filler is about four percent by weight of the polymer composite.

7 Claims, 62 Drawing Sheets

(51) Int. Cl.
*A61L 31/10* (2006.01)
*A61L 31/16* (2006.01)
*D06M 15/53* (2006.01)
*D06M 15/55* (2006.01)
*B82Y 30/00* (2011.01)
*D01D 5/00* (2006.01)
*D01F 6/14* (2006.01)

(52) U.S. Cl.
CPC ............ *D06M 15/53* (2013.01); *D06M 15/55* (2013.01); *B82Y 30/00* (2013.01); *D01D 5/0007* (2013.01); *D01F 6/14* (2013.01); *D10B 2321/06* (2013.01); *D10B 2401/062* (2013.01); *D10B 2401/20* (2013.01); *Y10T 442/2877* (2015.04)

(58) Field of Classification Search
CPC ........ D01D 5/0007; D01F 6/14; D06M 15/53; D06M 15/55; D04H 1/728; D10B 2321/06; D10B 2401/062; D10B 2401/20; Y10T 442/2877

USPC ........................................................ 442/166
See application file for complete search history.

(56) References Cited

U.S. PATENT DOCUMENTS

2004/0241436 A1   12/2004   Hsieh et al.
2011/0138685 A1   6/2011    Kalayci et al.

OTHER PUBLICATIONS

Written Opinion issued for PCT/US2012/041969 mailed on Sep. 5, 2012.

Capadona et al., "Nanocomposites Inspired by the Sea Cucumber Dermis," Mar. 7, 2008, Science, vol. 319, p. 1370-1374.

* cited by examiner

α-helix

β-sheet

End-group Functionalization

Appending succinic anhydride adds ≈ 202 mass units

Small amounts of γ-lactam end-group is observed after reaction

Quantitative yield

PDMS Addition - Triblock

GPC (THF) shows unimodal distribution
NMR (600 MHz, CDCl$_3$) indicates appropriate degrees of polymerization
90 % yield
PDI ≈ 2.2 (broadness due to PDMS)

DP ≈ 11     DP ≈ 62

Morphological Characterization

DSC and SAXS indicate phase separated morphology due to PDMS and PBLG thermal transitions and scattering peak, respectively Short range ordering is confirmed by scattering of mixed secondary structure PBLG and amorphous PDMS AFM further confirms phase separation with an interconnected network morphology a b c d 10% PVA w/v in Water   5% PVAc w/v in Toluene   ⟹   4 wt% PVA. PVAc composite ❑ Two tan delta peaks were observed for PVAMMT12.
❑ The first peak in PVAMMT12 may arise from the amorphous phase of PVA that crystallizes with the thermal energy.

Ca²⁺ absorption causes the composite to be transparent.

A = Composite – Dry
B = Composite – after NaOH
C = Composite – after CaCl₂

Procedure

- Soak the mat in methanol – overnight
- Drying - ~ 5 hours
- Pour PVAc solution into teflon dish
- Place the mat in the dish
- Pour more PVAc solution to fully immerse the mat
- Dry it for few days (~ 5 days)

Procedure

- Soak the mat in methanol – overnight
- Drying - ~ 5 hours
- Pour PVAc solution into Teflon dish
- Dry it to make a film
- Place the mat on top of the PVAc film
- Pour more PVAc solution to fully immerse the mat
- Dry it for few days (~ 5 days)

PVA.Elvax *44* wt%

PVA.Elvax *15* wt%

PVA.EOEPI *15* wt%

PVA.Elvax *15* wt%

PVA.EOEPI *15* wt%

POLYMER COMPOSITE AND METHOD OF FORMING SAME

RELATED APPLICATIONS

This application is a national stage application under 35 U.S.C. §371 of International Application No. PCT/US2012/041969 filed Jun. 11, 2012, which claims the priority to and the full benefit of U.S. Provisional Patent Application Ser. No. 61/495,942 filed Jun. 10, 2011, the entire disclosure of which is specifically incorporated herein by reference.

TECHNICAL FIELD

This application relates generally to forming materials and structures, and more particularly, to forming materials and structures that mimic naturally occurring materials.

BACKGROUND

Materials and structures that occur in nature can include properties suitable for a variety of applications. Such materials and structures can be mimicked to provide useful articles. For example, naturally forming materials can be capable of withstanding many complex and harsh environments, while still maintaining their mechanical properties.

SUMMARY

In accordance with one embodiment, a polymer composite comprises a filler and a matrix. The filler comprises an electrospun polymer mat. The matrix comprises a polymer film. The filler is arranged to respond to stimuli by altering its mechanical properties. In one example, the mat can be electrospun from poly(vinyl alcohol), and the matrix can be formed from ethylene oxide-epichlorohydrin 1:1 copolymer. The filler can be arranged so that the tensile storage modulus of the polymer composite changes in response to the filler being exposed to a stimulus. In another example, the filler is about four percent by weight of the polymer composite.

DETAILED DESCRIPTION

The apparatuses and methods disclosed in this document are described in detail by way of examples and with reference to the figures. It will be appreciated that modifications to disclosed and described examples, arrangements, configurations, components, elements, apparatuses, methods, materials, etc. can be made and may be desired for a specific application. In this disclosure, any identification of specific shapes, materials, techniques, arrangements, etc. are either related to a specific example presented or are merely a general description of such a shape, material, technique, arrangement, etc. Identifications of specific details or examples are not intended to be and should not be construed as mandatory or limiting unless specifically designated as such. Selected examples of articles, apparatuses and methods for forming materials and structures that mimic those found in nature are hereinafter disclosed and described in detail with reference made to figures, charts and graphs.

Mimicking materials and structures found in nature can provide inspiration for a number of fabricated materials and structures that are suitable for a variety of applications. For example, structures found in naturally occurring materials can be the inspiration for designing and fabricating materials that have suitable attributes such as, for example, suitable mechanical, optical, chemical properties and the like. In one example, articles inspired by naturally occurring materials and structures can be used as a drug delivery system. In another example, articles inspired by naturally occurring materials and structures can include generally translucent optical properties.

Figure 1:
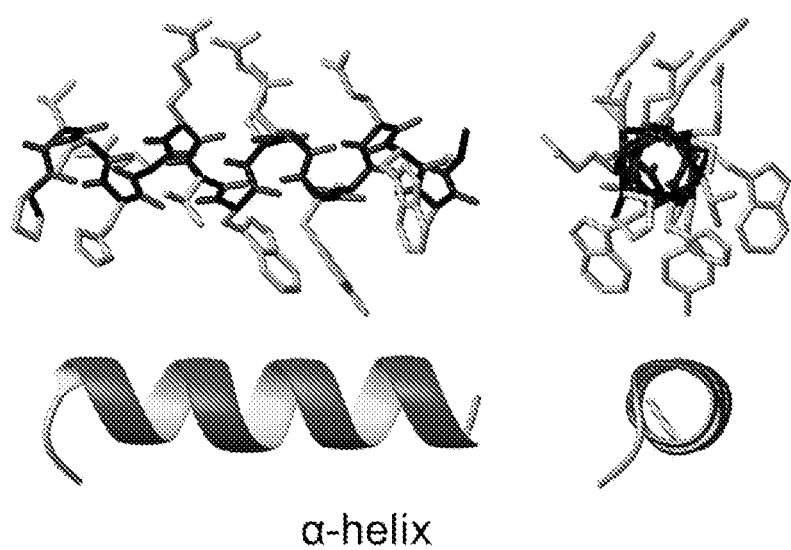
FIG. 1 illustrates examples of α-helix structure.
Figure 2:
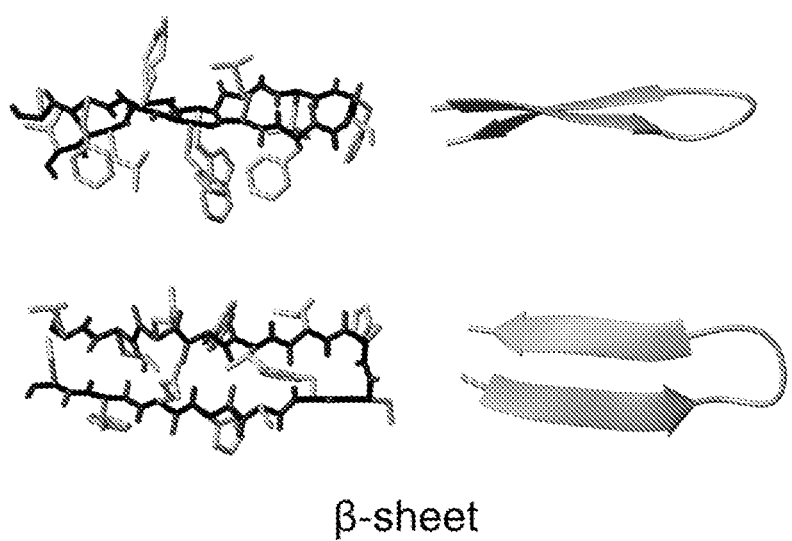
FIG. 2 illustrates examples of β-sheet structures.
Figure 3:
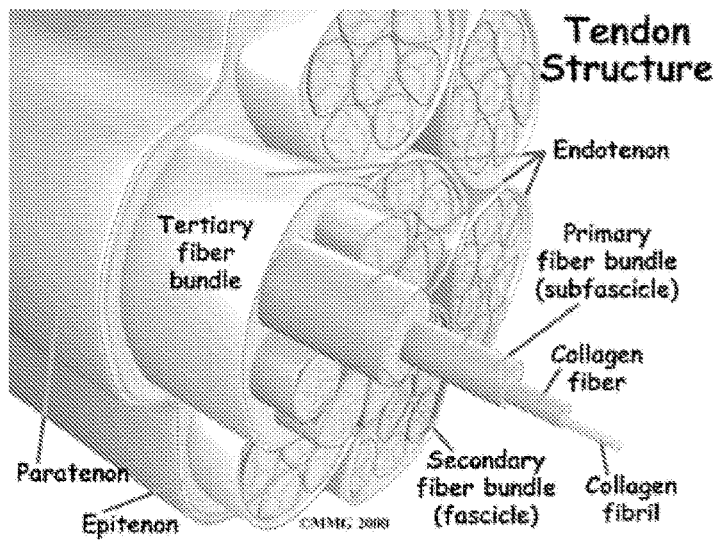
FIG. 3 illustrates an example of hierarchical structure of a tendon.
Figure 4:
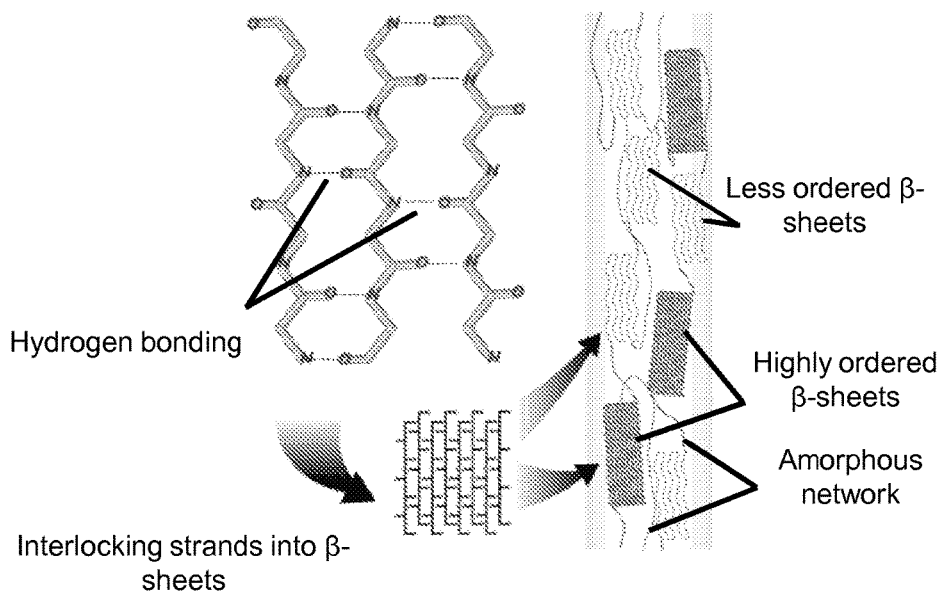
FIG. 4 illustrates an example of hierarchical structure of silk.

Hierarchical organization is a design pattern found throughout nature to construct materials that are mechanically robust and tough. Multiple levels of organization, acting through a cascading failure mechanism, for example, allow materials to absorb substantial quantities of energy before ultimate failure. There can be several significant energy absorbing structures found throughout nature such as, for example, α-helix and β-sheet. Such energy absorbing structures can be incorporated in the design of a high performance polymeric material. FIG. 1 illustrates examples of α-helix structure. FIG. 2 illustrates examples of β-sheet structure. Additional hierarchical structures found in nature are illustrated in FIGS. 3 and 4. FIG. 3 illustrates hierarchical ordering in a tendon, and FIG. 4 illustrates the hierarchical ordering of silk.

Figure 5:
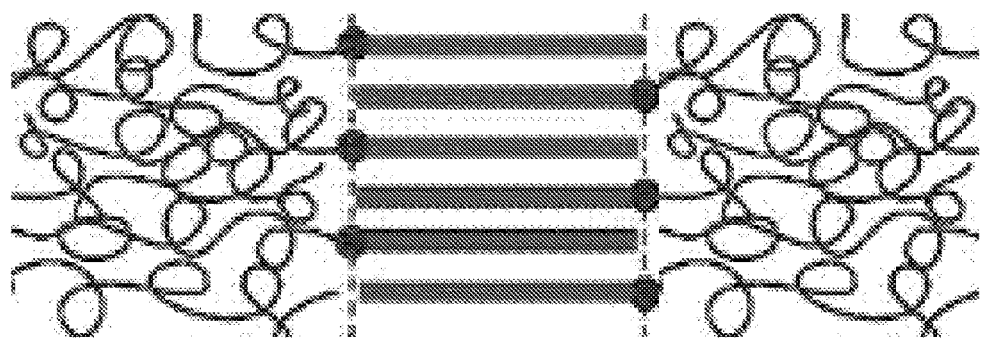
FIG. 5 illustrates an example of block copolymer morphology of coil-rod-coil copolymer structure.
Figure 6:
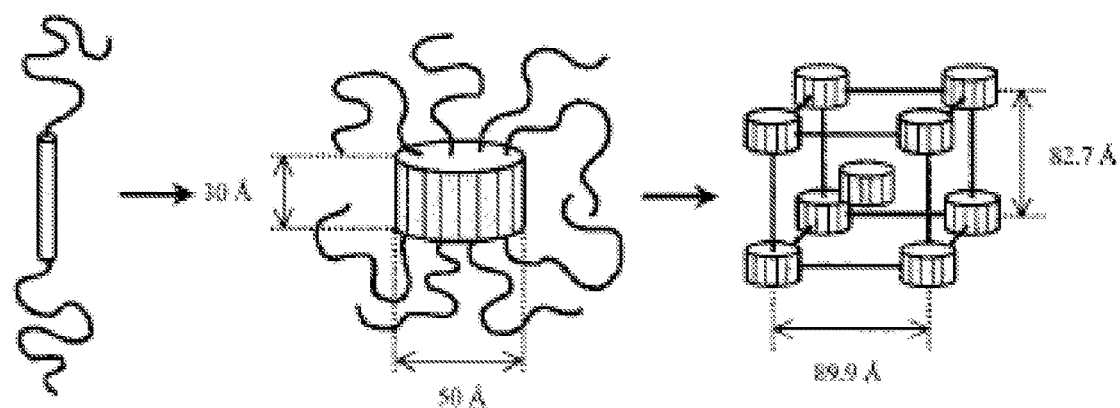
FIG. 6 illustrates an example of block copolymer morphology of a tetragonal structure.
Figure 7:
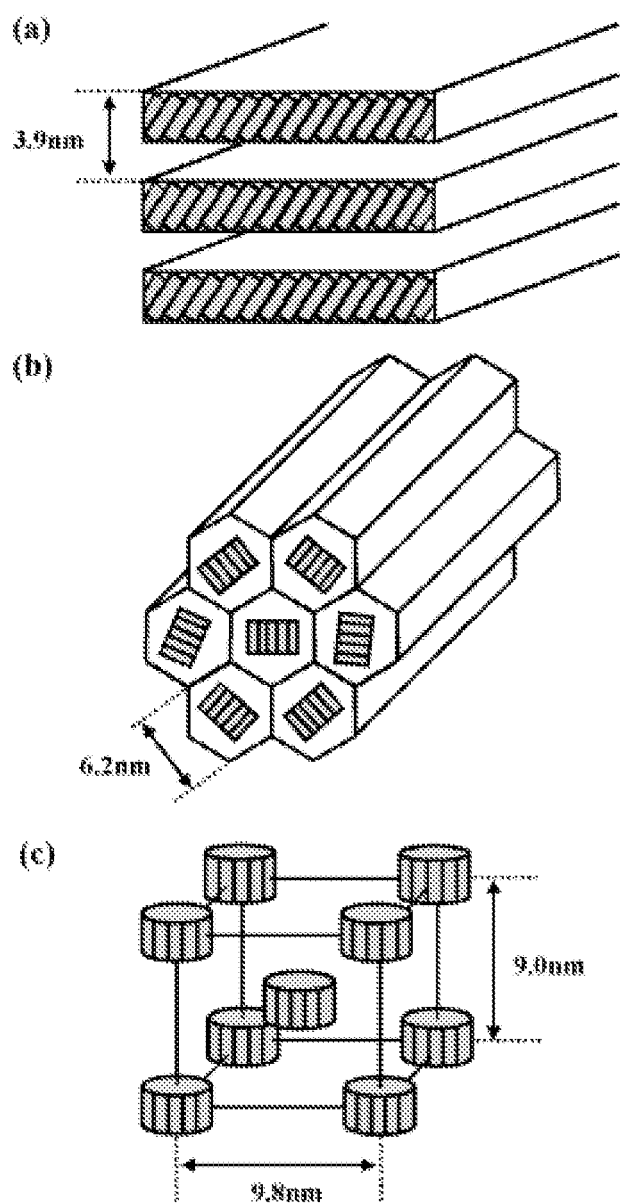
FIG. 7 illustrates examples of block copolymer morphology structures with coil length and molecular weight variations.
Figure 8:
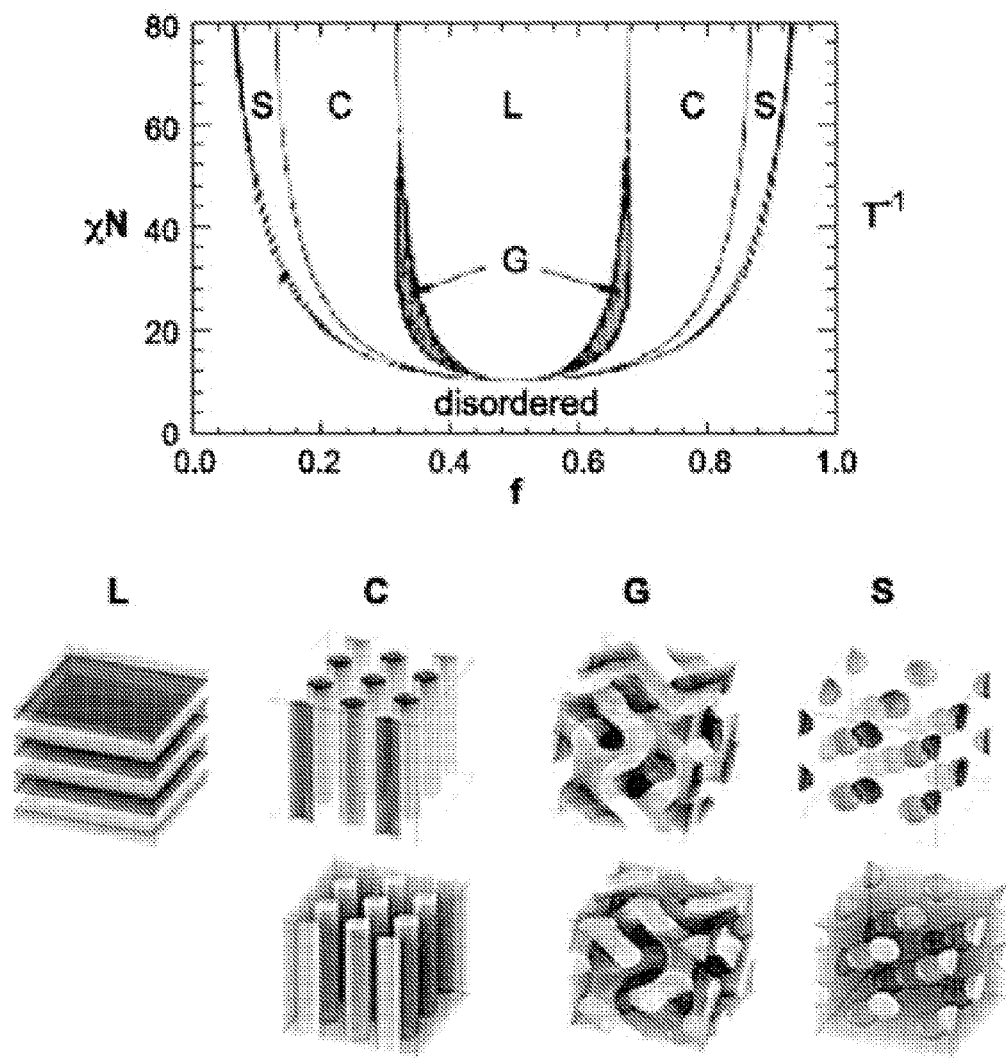
FIG. 8 illustrates a block copolymer phase diagram and examples of common morphologies.
Figure 9:
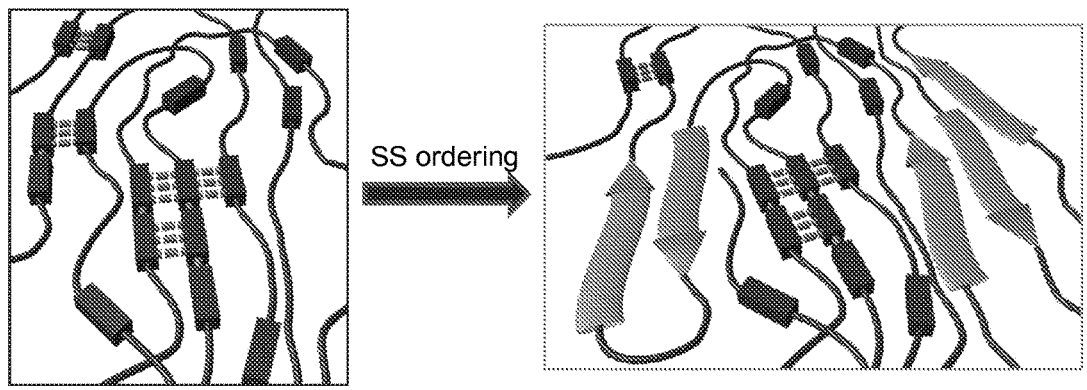
FIG. 9 illustrates an example of Soft Segment (SS) ordering.
Figure 10:
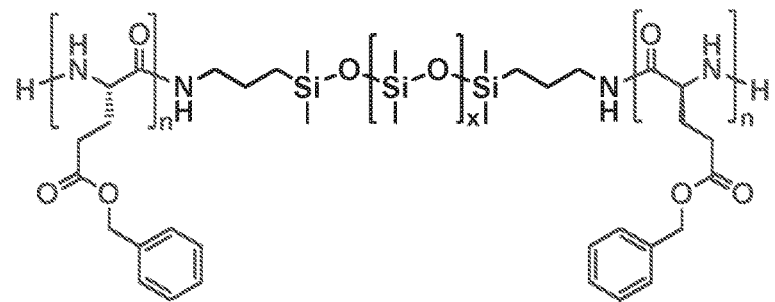
FIG. 10 portrays an example chemical notation of an example of Soft Segment (SS) ordering.
Figure 11:
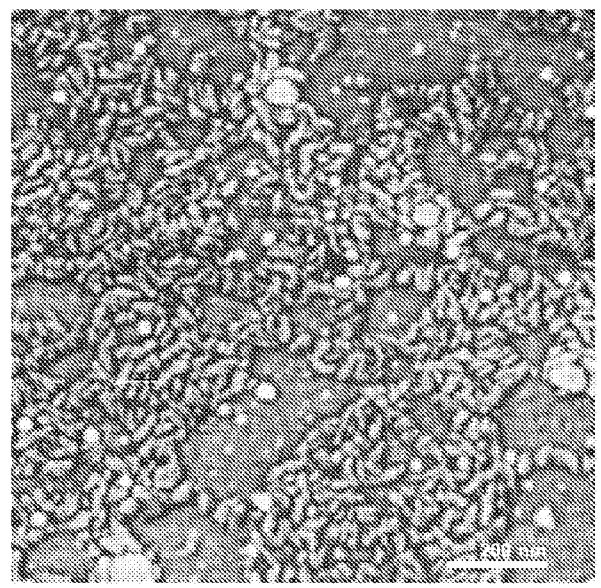
FIG. 11 portrays an atomic force microscope topographical scan of an example morphology.
Figure 12:
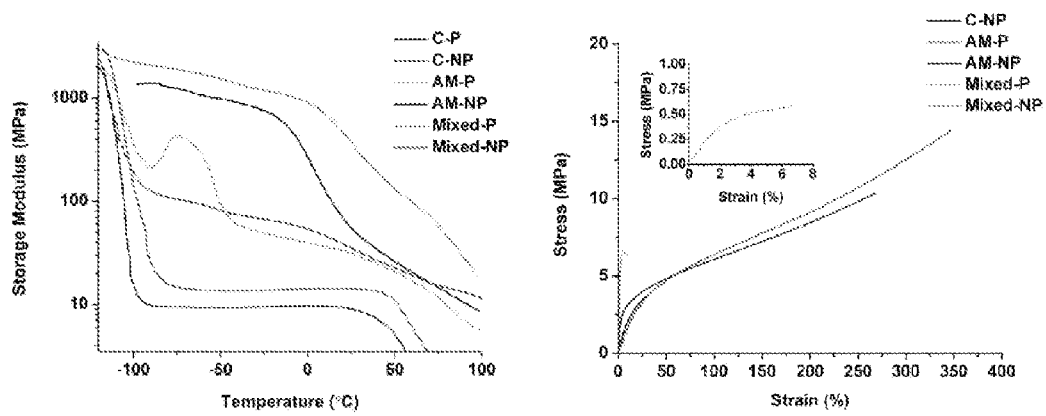
FIG. 12 portrays graphic data concerning DMA and tensile results of exemplary material.

Block copolymers such as, for example, coil-rod-coil structures, can exhibit an array of morphologies. For example, such morphologies can be lamellae or novel three-dimensional tetragonal lattices. Morphologies can depend upon characteristics such as coil length and molecular weight. Examples of morphologies are generally illustrated in FIGS. 5-8. FIG. 5 illustrates an example of coil-rod-coil copolymer structure. FIG. 6 illustrates an example of a tetragonal structure. FIG. 7 illustrates examples of coil length and molecular weight variation allowing formations of: a) lamellar structure, b) two-dimensional hexagonal structure, and c) three-dimensional tetragonal structure. FIG. 8 illustrates a block copolymer phase diagram and common morphologies Soft segment (SS) ordering can enhance mechanical properties in a series of polyurethane/ureas (PUU). Such soft segment ordering is illustrated in FIGS. 9 and 10. FIG. 11 shows a peptidic rod-coil-rod PUU copolymer, with AMF of peptide random fiber-like morphology. FIG. 12 illustrates DMA (left) and tensile (right) of PUUs containing peptidic ordering (x-P) based on the PBLG-PDMS-PBLG SS moiety. C-x, AM-x, and Mixed-x, can be crystalline, amorphous and combination of crystalline/amorphous hard segments.

Mechanical properties can be enhanced with the addition of elastomeric layer between glassy segments. Peptidic coil-rod-coil copolymers can be developed that are hierarchically self-assembling and that mimic natural structures. In one example, a peptidic coil-rod-coil copolymer can be incorporated into segmented polymers to achieve hierarchical organization. Such hierarchical organization can affect thermal and mechanical properties of the material. Examples of man-made material with such hierarchical organization are illustrated and described in FIGS. 13-19 below.

Figure 13:
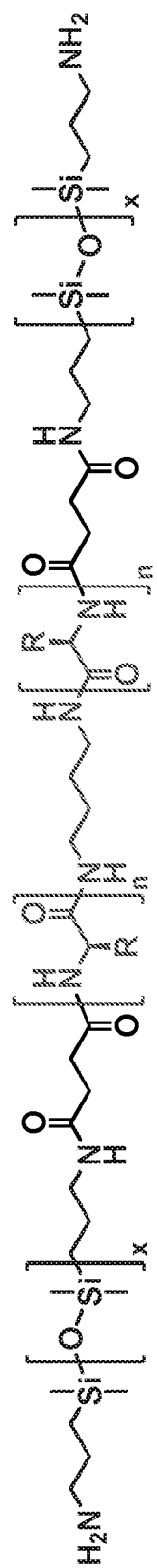
FIG. 13 portrays a chemical notation of an example of man-made material with subject hierarchical organization.
Figure 14:
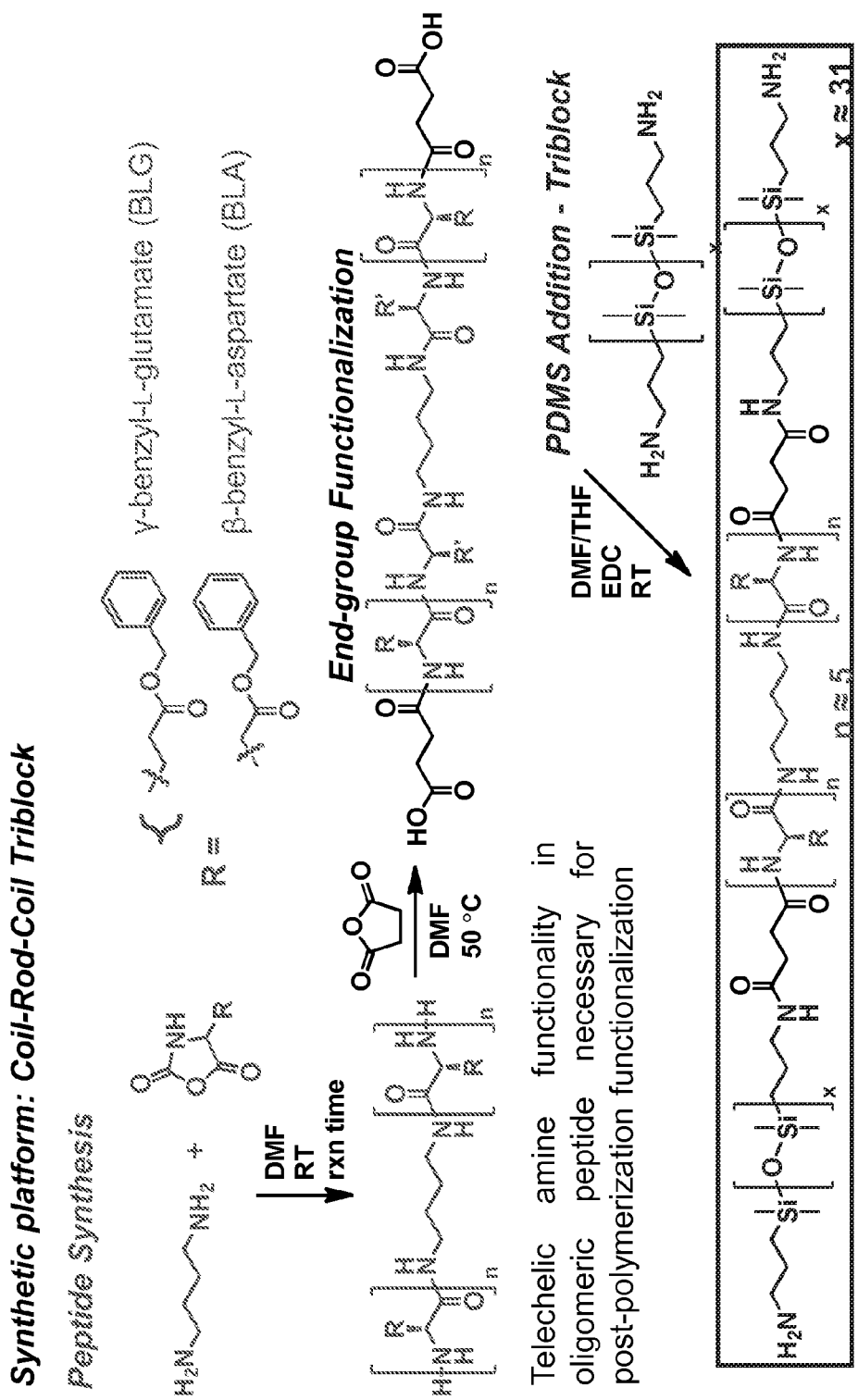
FIG. 14 illustrates peptide synthesis, end group functionalization, and PDMS addition of the man-made material of FIG. 13.
Figure 15:
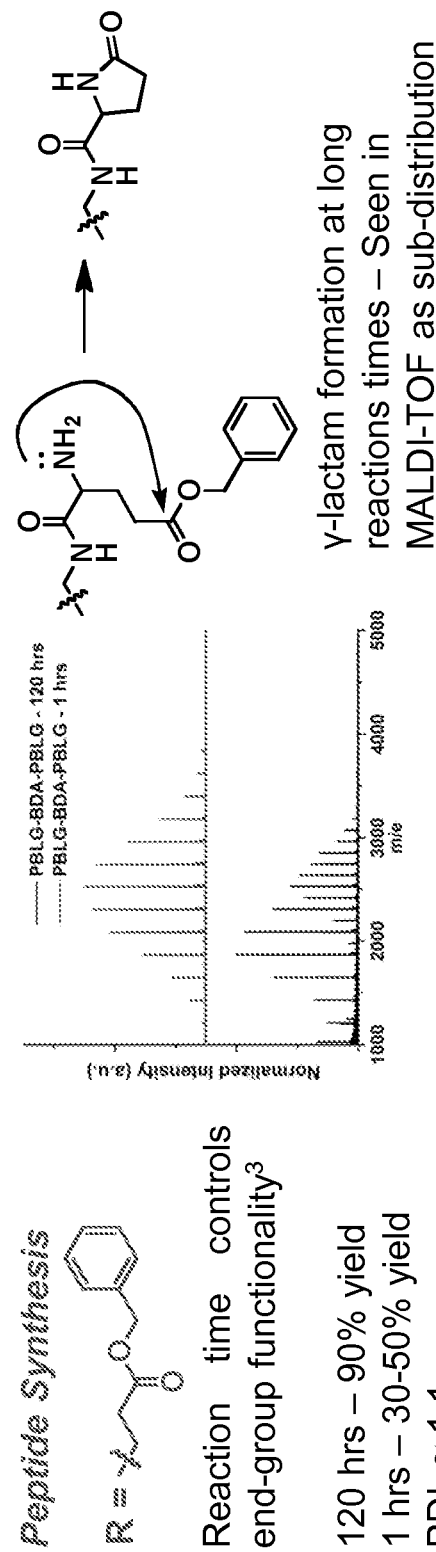
FIG. 15 illustrates in greater detail the peptide synthesis of FIG. 14.
Figure 16:
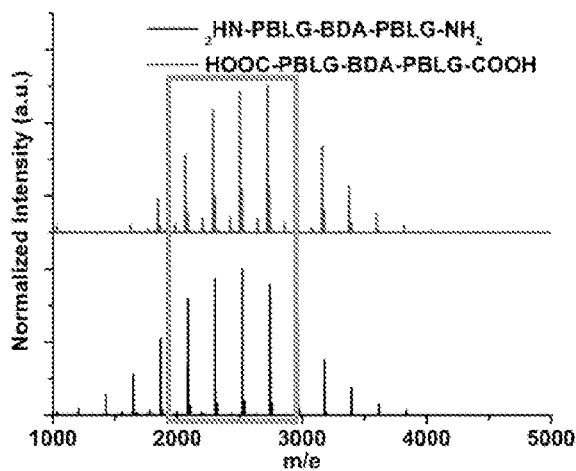
FIG. 16 illustrates in greater detail the end group functionalization of FIG. 14.
Figure 16:
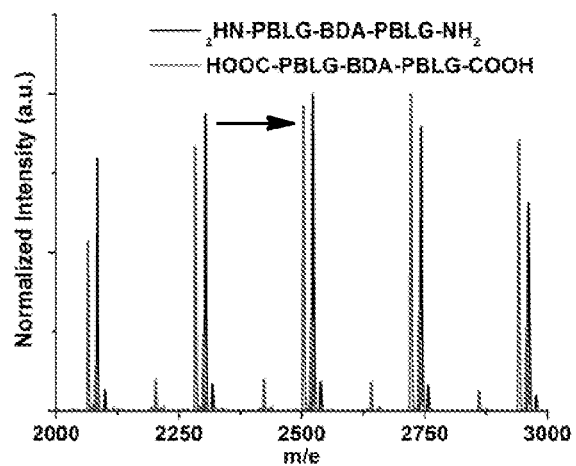
Figure 17:
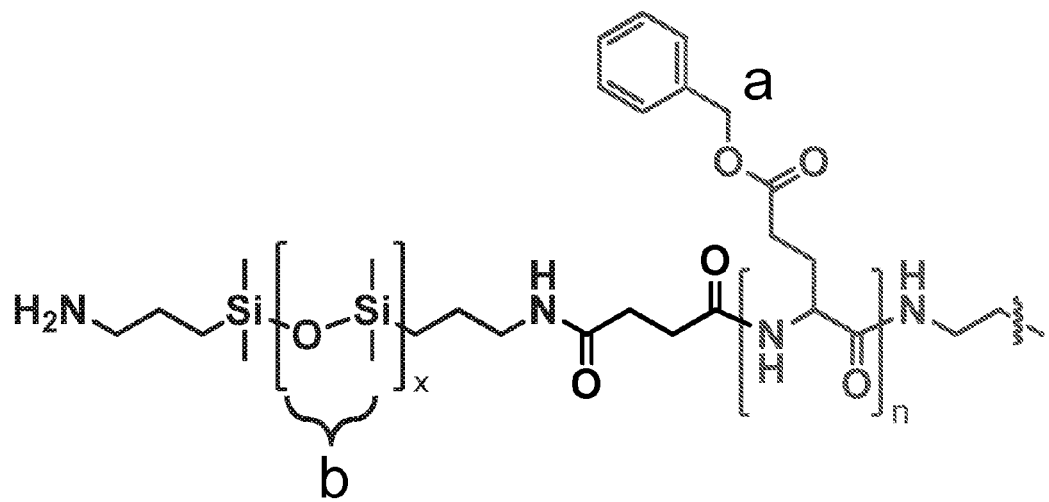
FIG. 17 illustrates in greater detail the PDMS addition of FIG. 14.
Figure 17:
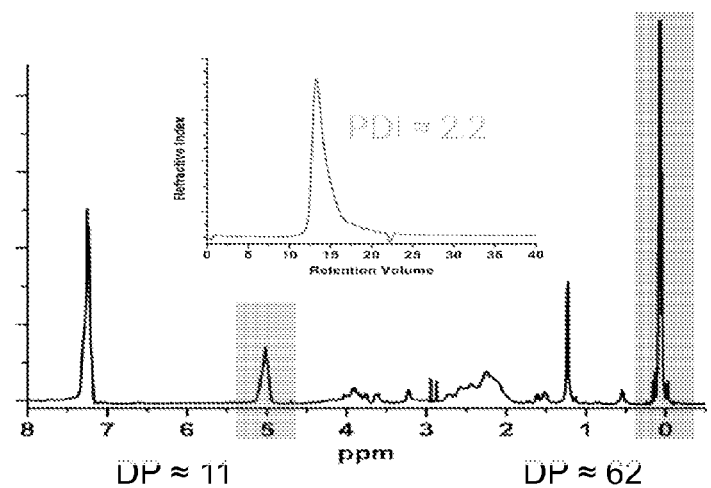
Figure 18:
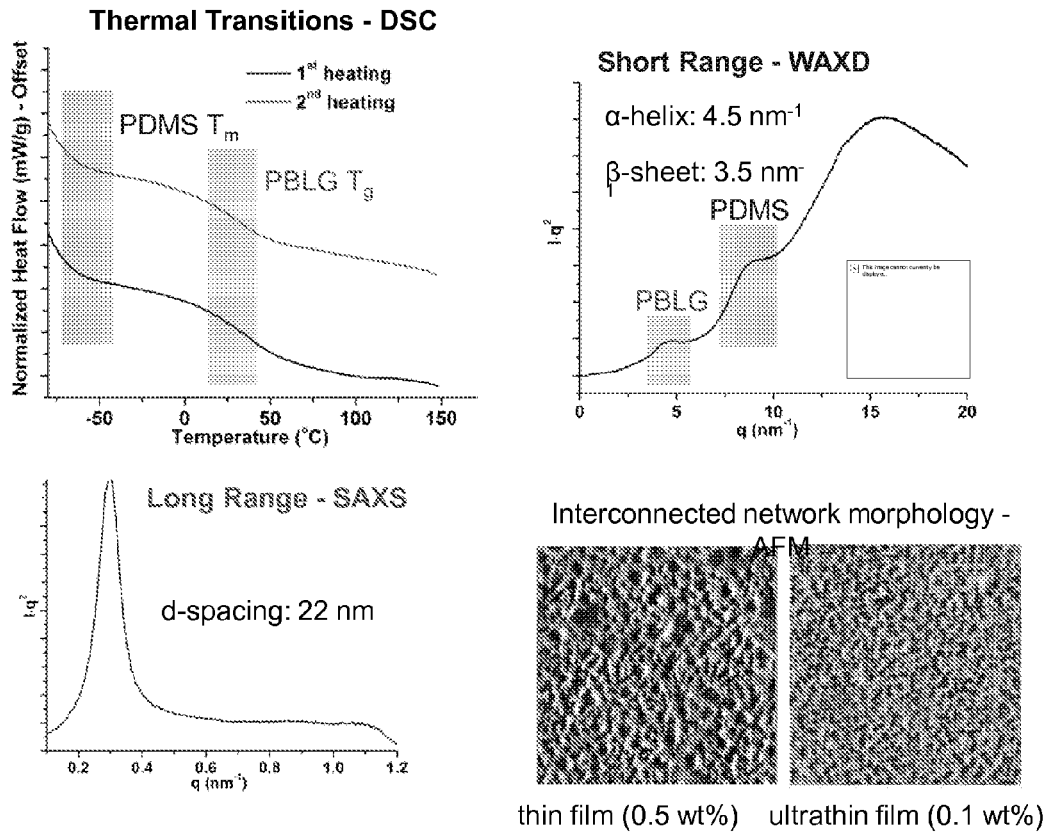
FIG. 18 portrays an atomic force microscope topographical scan of an example morphology and portrays graphic data concerning morphological characterizations of the exemplary material.
Figure 19:
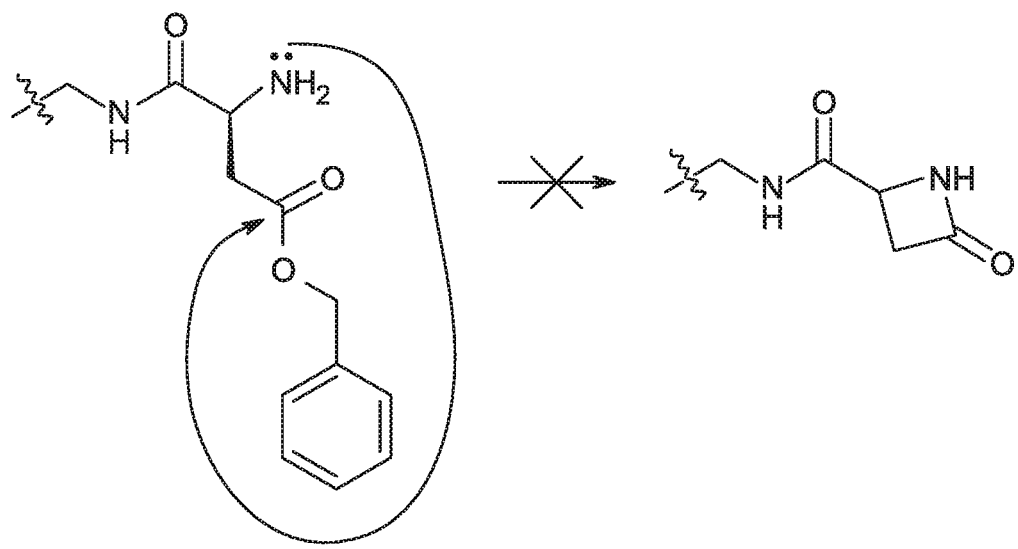
FIG. 19 illustrates an example man-made material with subject hierarchical organization.
Figure 19:
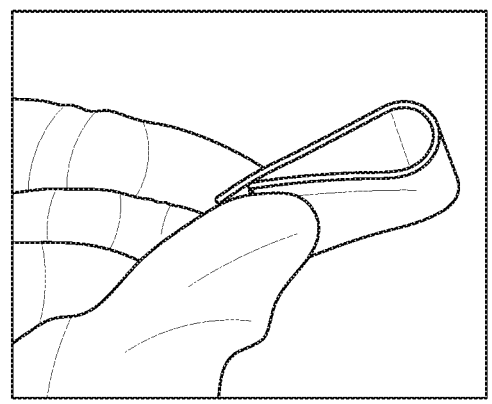
Figure 19:
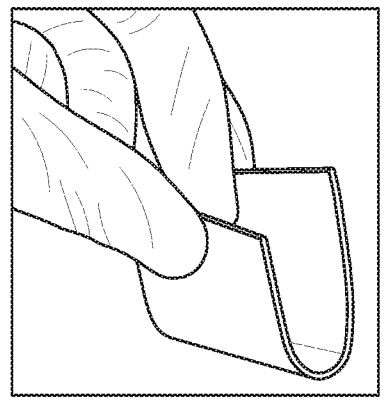

FIG. 13 is a representation of a novel peptidic coil-rod-coil copolymer incorporated into a segmented polymer. FIG. 14 illustrates peptide synthesis, end group functionalization, and PDMS addition. FIGS. 15-17 provides greater detail regarding peptide synthesis, end group functionalization, and PDMS addition, respectively. FIG. 18 describes morphological characteristics, and FIG. 19 depicts examples of the novel copolymer. Morphological studies indicate hierarchical organization for such chemistries. In addition, BLA based materials can be synthesized to perform in a similar manner. The BLA can allow for higher yields. Such higher yields can be due to a lack of β-lactam formation.

As previous discussed, natural materials often include desirable properties that can be mimicked to provide useful materials and structures. For example, naturally forming materials can be capable of withstanding many complex and harsh environments, while still maintaining their mechanical properties such as, for example, toughness, strength and extensibility. An examination of natural materials such as, for example, bone, collagen and spider silk, can show that a design element is a hierarchical architecture that, under deformation or stress, can utilize the multiple levels of organization to absorb energy and reinforce the material. Bone, an inorganic/organic composite, is composed of inorganic plate-like blocks (hydroxyapatite) encapsulated by an organic matrix composed of type I collagen. Similarly, nacre has a brick and mortar configuration comprised of bricks of crystallized inorganic minerals (aragonite) together with a complex mixture of proteins. Spider silk, a material with a tensile strength superior to high-grade steel, is a biological thermoplastic elastomer consisting of highly crystalline, alanine-rich β-sheet domains and an "oriented" amorphous, glycine-rich continuous matrix.

One area of research is the development of materials that are capable of mimicking nature's diverse and enhanced mechanical behavior. Materials suitable to such mimicking include thermoplastic segmented polyurethanes, which can provide a unique and dynamic framework for the design of high performance materials. Thermoplastic polyurethanes (TPUs) are an important and diverse class of polymers. Such multiblock copolymers are typically composed of a high melting temperature ($T_m$) or high glass transition temperature ($T_g$) hard segment (HS) and a flexible, low $T_g$ continuous soft segment (SS). The role of soft domain ordering on mechanical response in hierarchically-designed thermoplastic polyurethanes can be important to forming materials that mimic naturally formed materials.

For example properties such as thermal and mechanical properties of TPUs can be affected by SS ordering. For, polyurethanes with varying polycaprolactone (PCL) SS molecular weight, a crystallizable soft domain can enhance mechanical properties. For biodegradable polyurethanes containing crystallizable PCL SS, the crystallinity of the SS and the increased phase separation can reinforce the polyurethane structure and amplify the overall properties (tensile strength, initial modulus) by acting as physical crosslinks in a manner that is similarly attributed to the HS. Semicrystalline polyester diols can enhance polyurethane properties and crystalline soft domain morphology can provide additional reinforcement to the polyurethane hard phase, and at sufficient concentrations can demonstrate increased modulus and toughness. The soft and hard segment ordering can affect the morphology and mechanical behavior of semicrystalline polyurethanes. Due to the hierarchical nature of the segmented polyurethanes, the SS crystallinity can add extensibility and reinforced the polymer during deformation in a manner similar to the hard domains, allowing for increased energy dissipation and overall increased toughness. The crystalline domains within the continuous matrix can offer an additional means of modifying and designing high performance polyurethanes.

For multiblock copolymers, material properties can be tailored through the incorporation of peptidic segments. Such peptidic segments can mimic what is found in nature. Either the tetrapeptide Gly-Ala-Gly-Ala or poly(Ala), derived from the crystalline region of *Bombyx mori* (*B. mori*) silk and spider dragline silk, can be utilized as a β-sheet assembly encapsulated by a matrix of soft poly (ethylene glycol). Multiple approaches can be utilized to form the peptide segment. For example, a method includes the use of an aromatic hairpin residue to force formation of parallel β-sheets. In another example, a linear, random copolymer in which the β-sheets are unrestricted and free to assemble into parallel or antiparallel structures. Both exemplary methods can generate synthetic polymers with microphase separated nanostructures and very good mechanical properties. Tensile response could be modulated and tuned by varying both the building block structure (forced hairpin) and chemical nature. Generally well-defined ABA block copolymers can be synthesized with poly(β-benzyl-L-aspartate) (PBLA) as the A segment and PEO as the B segment. Film forming PBLA-b-PEO-b-PBLA can exhibit excellent flexibility and strength not observed for the individual PEO and PBLA blocks. Spherulitic formation can result in such properties as its hierarchical structure can work as a supportive framework. Through thermal treatment, a conformational change from α-helix to β-sheet can impart greater strength due to the multiple interchain hydrogen bonds.

The hierarchical ordering in the soft domain can impact polyurethane-ureas through bio-inspired peptidic segments. For example, the triblock poly(benzly-L-glutamate)-block-poly(dimethylsiloxane)-block-poly(benzyl-L-glutamate) (PBLG-b-PDMS-b-PBLG) can be employed as the soft block. Such a copolymer can form well-defined secondary structures based on the molecular weight of the peptide segment; at low molecular weight (<10 residues), the PBLG can form primarily β-sheets, while at higher molecular weight (>10 residues) the secondary structure is an α-helix. Such a secondary structural formation can promote ordering in the SS, which can act as an additional load-bearing component.

Materials that can be utilized include, but are not limited to, 1,2-bis(diethylphosphino)ethane (depe), bis(1,5-cyclooctadiene)nickel ($Ni(COD)_2$), Anhydrous N,N'-dimethylacetamide (DMAc), N-methyl-2-pyrrolidone (NMP), dibutyltin dilaurate (DBTDL), depe, $Ni(COD)_2$, tetrahydrofuron (THF), 1,6-hexamethylene diisocyanate (HDI), isophorone diisocyanate (IPDI), 1,4-butanediol (BDO), α,ω-bis(3-aminopropyl)poly(dimethylsiloxane) (PDMS), benzyl-L-glutamate N-carboxyanhydride (BLG-NCA). Tetrahydrofuron (THF) can be distilled over sodium metal prior to use; 1,6-hexamethylene diisocyanate (HDI), isophorone diisocyanate (IPDI) and 1,4-butanediol (BDO) can be vacuum distilled and stored under an N2 atmosphere; αω-bis(3-aminopropyl)poly(dimethylsiloxane) (PDMS) can be dried and degassed under vacuum at 100° C. for 5 hours and stored under an N2 atmosphere; and benzyl-L-glutamate N-carboxyanhydride (BLG-NCA) can be prepared according to literature procedures.

Figure 20:
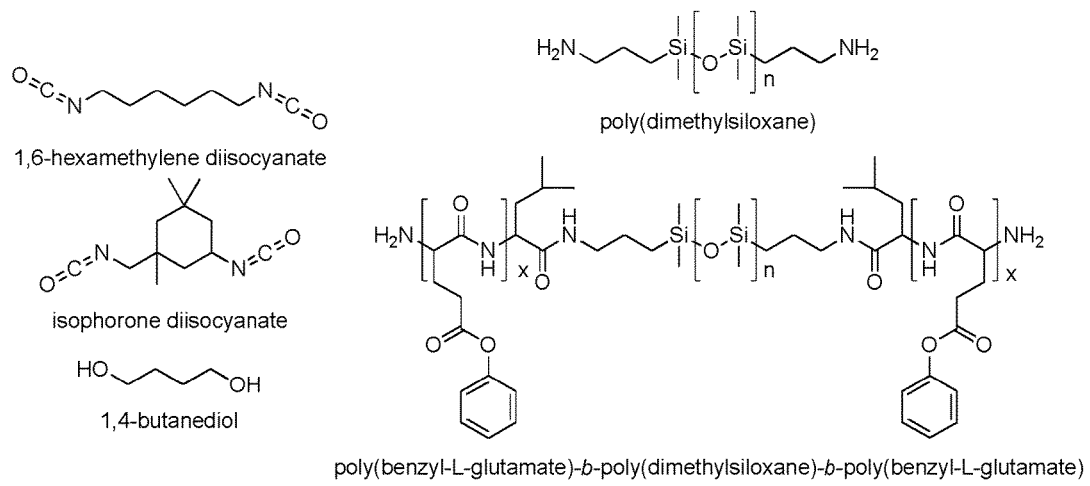
FIG. 20 illustrates example molecular structures of polyurethane components.

As will be understood, Poly(benzyl-L-glutamate)-b-poly (dimethylsiloxane)-b-poly(benzyl-L-glutamate) (PBLG-b-PDMS-b-PBLG) can be synthesized. In addition, the synthesis can be use a nucleophile or base as initiator. Polyurethanes/ureas (PUUs) can also be synthesized. Segmented PUUs can be prepared via a two-step prepolymer route using either HDI or IPDI and BDO as the hard segment and PDMS or PBLG-b-PDMS-b-PBLG as the soft segment (see molecular structures of polyurethane components in FIG. 20). The polymerizations can be carried out in an N2 atmosphere glove box to minimize side reactions with moisture. The hard segment content (weight percent, wt %) can be calculated using the following equation:

$$wt(\%)HS = \frac{(n+1)M_{DI} + nM_{BDO}}{(n+1)M_{DI} + nM_{BDO} + M_{SS}}$$

where n, $M_{DI}$, $M_{BDO}$, and $M_{SS}$ is the is the number of moles of BDO, the molecular weight of the diisocyanate, butanediol and the chosen soft segment, respectively. The hard segment content can be set at 33 wt % for PUUs; however, a modified hard segment content (wt(%)$HS_m$) can also be defined that considers the PBLG fraction:

$$wt(\%)HS_m = \frac{(n+1)M_{DI} + nM_{BDO} + M_{PBLG}}{(n+1)M_{DI} + nM_{BDO} + M_{PDMS} + M_{PBLG}}$$

As a synthetic example, in an N2 atmosphere glove box a 2-neck flask equipped with a dropping funnel and a Vigreux condenser was charged with IPDI (1.84 g, 8.29 mmol) dissolved in 2 mL NMP. PBLG-b-PDMS-b-PDMS (5.0 g, 1.0 mmol) and 5 drops of DBTDL was dissolved in 30 mL of NMP and slowly added to the IPDI solution through the dropping funnel over a 1 hour period. The reaction mixture was stirred for 3 hours at 65° C. to form the prepolymer. The prepolymer was then extended through the addition of BDO (0.657 g, 7.29 mmol) and the mixture stirred at 65° C. overnight (~16 hours). The reaction mixture was precipitated into methanol, filtered and dried under vacuum until constant weight.

For the segmented PUUs containing PBLG-b-PDMS-b-PBLG, NMP can be used as the reaction medium. For PUUs containing HDI, BDO and PDMS, a 50:50 mixture of DMAc:THF can be utilized. THF can be an appropriate solvent for the PUUs containing IPDI, BDO, and PDMS.

Absolute molecular weights and molecular weight distributions of the polypeptide soft segment and soluble polyurethanes can be determined by Gel Permeation chromatography (GPC) equipped with a Viscotek Model 270 Dual Detector light scattering unit and two Tosoh Biosep GMHHR-M columns in series with Polymer Labs Mesopore. Samples can be run in THF at 1 mL/min at 25° C.

Thermal phase transitions can be obtained using a TA Instruments Q100 Differential scanning calorimetry (DSC). As-precipitated samples can be subjected to two heating and cooling cycles with a heating rate of 10° C./min from 25° C. to 200° C. under an N2 atmosphere. A second heating/cooling cycle can be used to identify the glass transition, melting, crystallization temperature, and enthalpy of melting. The glass transition can be taken as the midpoint of the stepwise change in the heat flow signal. Melting and recrystallization can be determined from the peak maximum (exotherm) and the peak minimum (endotherm). Enthalpy of melting can be taken as the area under the melting peak.

PUU films can be prepared by solution casting from a 10 wt % solution into Teflon molds and allowed to dry in air for 3 days. After 3 days, the films can be annealed under vacuum at 75° C. for 24 hours. Film thicknesses can be on the order of 0.25 mm. PUUs containing PBLG-b-PDMS-b-PBLG can be cast from NMP. The PUUs derived from HDI, BDO, PDMS can be cast from DMAc. The PUU based on IPDI, BDO, and PDMS can be cast from THF.

Dynamic mechanical analysis (DMA) films can be prepared as described above. The films can be analyzed using a TA Instruments Q800 DMA operating at a frequency of 1 Hz, a temperature range of −125° C. to 100° C. and a heating rate of 3° C./min.

Small-angle X-ray scattering data can be acquired at the X27C beamline at the National synchrotron light source (NSLS) at Brookhaven National Laboratory. The polyurethane/urea thin films can be annealed at 75° C. under vacuum to improve hard and soft segment segregation. The X27C X-ray wavelength, λ, can be 1.371 Å, monochromatized using a double-multi-layer (silicon/tungsten) monochromator. The relative X-ray intensity can be measured before ($I_0$) and after ($I_1$) the sample by using proportional counters. Wide-angle X-ray data can be acquired using a X-ray source Micromax Rigaku 002+ producing Cu Kα radiation (λ=0.154 nm) and collimated using three pinholes. Due to the isotropic nature of the samples, data can be reduced from 2D (intensity vs. 2Θ, χ) to 1D (intensity vs. 2Θ), where 2Θ is the scattering angle and χ is the azimuthal angle. as q where:

$$q = 4\pi \sin(\theta)/\lambda.$$

A Veeco diMultiMode V Atomic Force Microscope (AFM) with a Nanoscope IIIa controller and a multimode scanning mode microscope can be used to probe the nanostructured morphology of the polyurethane/urea films. Phase images of the sample surfaces can be collected in tapping mode using NanoDevices Metrology Probes tips (350-380 kHz, 130 μm).

Tensile properties can be determined with an Intron model 5565 Universal Testing Machine equipped with a 1 kN load cell. Sample films can be prepared as described above and cut according to ASTM D 638. Samples can be elongated to failure at a rate of 100% initial gauge length per minute. Properties can be averaged over at least three samples.

A series of segmented PUUs can be synthesized by varying the HS type (crystalline vs. amorphous) and varying the SS type (peptidic vs. non-peptidic). Table 1 details examples of HS and SS type, molecular weight, and PDI of polyurethanes.

TABLE 1

Compositional details of polyurethanes and starting materials.

| Polymer | HS type | SS type | $M_n$ (g/mol) | PDI | HS content (wt %) | Modified HS content (wt %) |
|---|---|---|---|---|---|---|
| C-P | HDI-BDO | PBLG-PDMS-PBLG | 42700 | 2.4 | 33 | 66 |
| C-NP | HDI-BDO | PDMS | 58300 | 2.2 | 33 | 33 |

TABLE 1-continued

Compositional details of polyurethanes and starting materials.

| Polymer | HS type | SS type | $M_n$ (g/mol) | PDI | HS content (wt %) | Modified HS content (wt %) |
|---|---|---|---|---|---|---|
| AM-P | IPDI-BDO | PBLG-PDMS-PBLG | 44400 | 1.8 | 33 | 66 |
| AM-NP | IPDI-BDO | PDMS | 62500 | 2.1 | 33 | 33 |
| PBLG$_5$-b-PDMS-b-PBLG$_5$ | — | — | ~5000* | 1.07-1.1 | | |
| PDMS | — | — | ~2500 | | | |
| IPDI-BDO | — | — | 3100 | 1.1 | | |
| HDI-BDO | — | — | 2800 | 1.1 | | |

*Determined by NMR

The nomenclature for the hierarchically-designed polyurethane/ureas follows an X-Y structure. X is defined as the HS type (C: crystalline, AM: amorphous) and Y is defined as the SS type (P: peptidic, NP: non-peptidic).

Thermoplastic PUUs generally exhibit multiple thermal transitions corresponding to the individual chemical components of the microphase separated polymer. If phase mixing occurs, the temperature regions of the pure domains can be shifted or become indistinguishable. In order to maximize mechanical properties attributed to hierarchical ordering, it can be suitable to have well defined microphase separation such that the distinct domains (hard and soft) may exhibit their respective properties (dynamic crosslinks, extensibility). Utilizing DSC and DMA, soft and hard segment thermal transitions can be investigated. With respect to DSC, second heating data can be evaluated to eliminate any metastable microstructures due to initial thermal treatment. Similar thermal transitions can be observed in annealed films used for X-ray and mechanical analysis.

Figure 21:
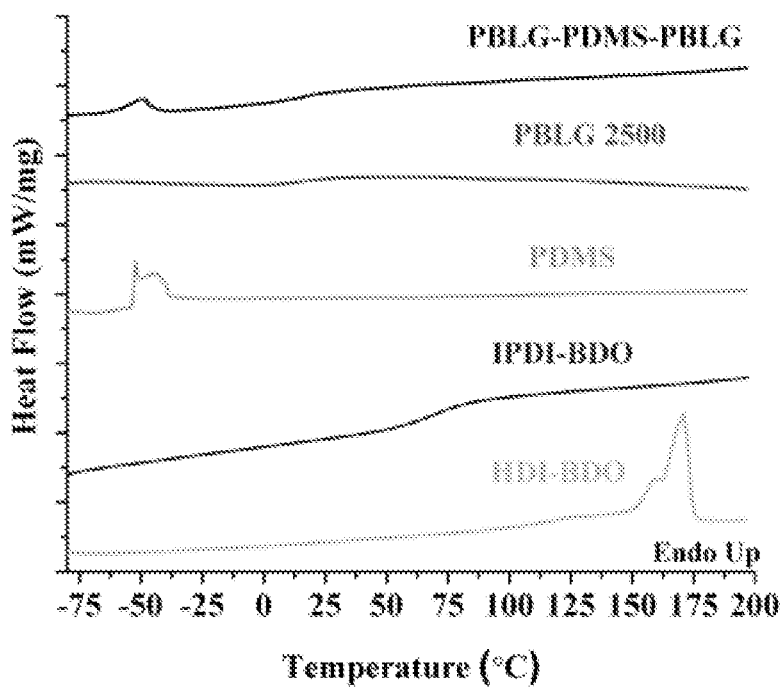
FIG. 21 portrays graphic data concerning DSC scans of exemplary materials.
Figure 21:
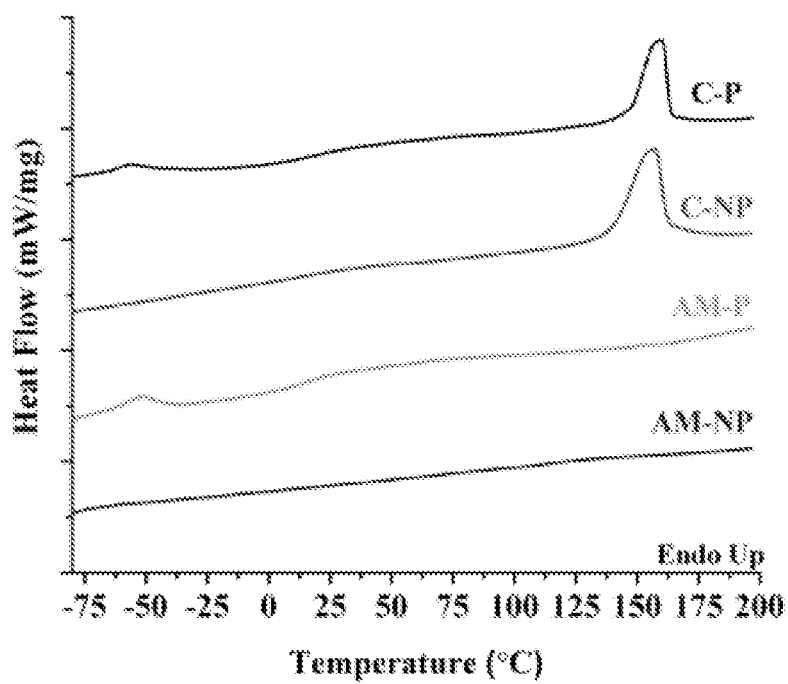

As shown in results of DSC thermograms (shown in Table 2 and FIG. 21), in the PUUs where soft segment transitions can be detected (C-P, NC-P), the PDMS $T_m$ and PBLG $T_g$ may only slightly shift in comparison with the pure components. Relatively small amounts of hard and soft domain can be mixed. The hard domain structure (amorphous vs. crystalline) can have minimal impact on the ability of PBLG-b-PDMS-b-PBLG form ordered structures. The PDMS melting transition can be suppressed in the non-peptidic systems, but observed in the peptide-containing PUUs. This may be due to a tethering or anchoring effect triggered by the PBLG glassy ordering. A similar effect can be demonstrated in polystyrene-b-polydimethylsiloxane (PS-b-PDMS) copolymer in which the PS anchoring junctions confined the PDMS block, resulting in behavior that can be analogous to semicrystalline PDMS homopolymer. FIG. 21, depicts a second heating DSC scan (10° C. min$^{-1}$) of polyurethane compositional materials and polyurethanes. Plots have been stacked for better clarity.

TABLE 2

Thermal transitions of polyurethanes and individual polyurethane components.

| | Soft segment | | | Hard Segment | | |
|---|---|---|---|---|---|---|
| Polyurethanes and components | PDMS T. (° C.) | PBLG $T_g$ (° C.) | PDMS ΔHf, % crystallinity | HDI-BDO T. (° C.) | IPDI-BDO $T_g$ (° C.) | HDI-BDO ΔHf, crystallinity |
| C-P | −56 | 20 | 3.1, 5 | 159 | — | 13.7, 16 |
| C-NP | — | — | — | 156 | — | 20.3, 24 |
| AM-P | −50 | 18 | 3.2, 5 | — | — | — |
| AM-NP | — | — | — | — | — | — |
| PBLG$_5$-b-PDMS-b-PBLG$_5$(P) | −49 | 15 | 7.4, 12 | — | — | — |
| PBLG 2500 | — | 19 | | — | — | — |
| PDMS (NP) | −48 | — | 11.1, 18 | — | — | — |
| IPDI-BDO (AM) | — | — | — | — | 71 | — |
| HDI-BDO (C) | — | — | — | 170 | — | 81.1, 96 |

In one example, the crystallinity of the HDI-BDO hard segment decreased (33%) upon the addition of the peptidic block. This can be due to reduced mobility induced by ridged PBLG. Additionally, the PDMS crystallinity was independent of the hard segment type, which is consistent with the PBLG anchoring argument as described above.

Figure 22:
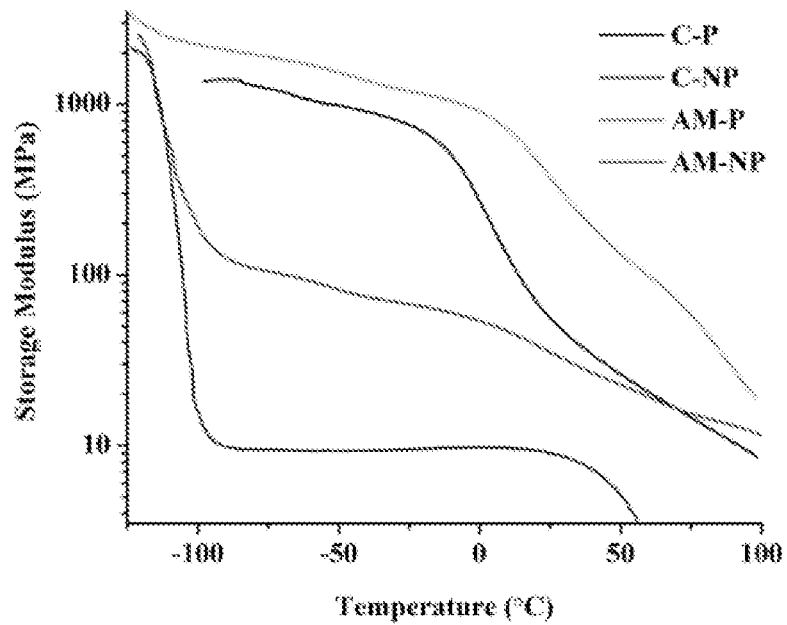
FIG. 22 portrays graphic data concerning dynamic behavior of exemplary materials.
Figure 22:
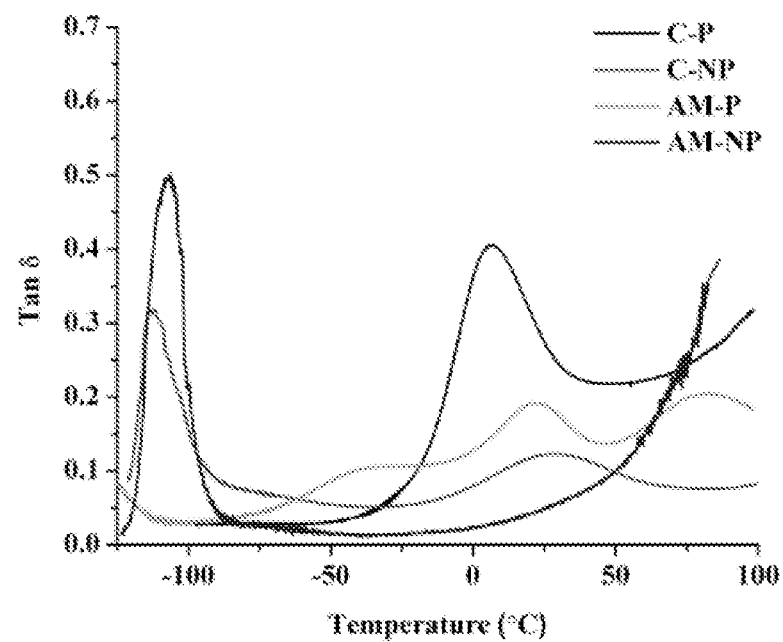

The multiphase nature of hierarchically-assembled PUUs can also be evaluated using dynamic mechanical analysis (DMA). DMA has proven to be a suitable tool in probing the thermo-mechanical properties of segmented PUUs, including for example stiffness (storage modulus) and molecular motion (tan δ). In one example, the dynamic behavior (exemplary data shown in FIG. 22) of both non-peptidic PUUs show sharp transitions around −110° C. corresponding to the $T_g$ of PDMS. However, a more gradual decrease in storage modulus is observed in the peptide-containing PUUs. With the addition of the peptidic block, the storage modulus for both the amorphous and crystalline hard segment PUUs can be significantly enhanced over a broader temperature range (AM-P: −110° C. to 18° C. vs. AM-NP: −110° C. to −90° C.). The PBLG segment can be reinforcing the PUU until the $T_g$ of the peptide is reached. A similar effect can be observed in a series of segmented PUUs containing an HDI-BDO hard segment and either amorphous PEO-b-PPO-b-PEO or semicrystalline PEO soft segment. In the PUU containing semicrystalline PEO, the low temperature stiffness can increase and extend over a broader range. Upon melting the PEO crystallites, a reduction in mechanical properties can be observed; however, a stable plateau modulus similar to the amorphous PUUs can be reached. The enhanced mechanical integrity can be attributed to the soft segment crystalline regions acting as reinforcing fillers while the mutual plateau modulus is accredited to the HDI-BDO hard segment.

Multiple tan δ transitions can be assigned to the respective segments of the polyurethanes, supporting the microphase separated morphological picture illustrated by DSC. In one example, in the AM-P PUU, a broad peak centered at −48° C. is observed, agreeing well with the PDMS melting transition seen in DSC. The broadness of the peak can be attributed to the restricted flexibility of the PDMS due to the ridged PBLG. However, in another example, this relaxation is not observed in the C-P PUU. This may be due to the more crystalline nature of the hard segment compounding with the ridged PBLG restricting molecular mobility. The glass transition of PBLG can be observed in both C-P and AM-P PUUs as broad peaks centered at 6° C. and 22° C., respectively. The decreased $T_g$ in C-P can indicate interfacial mixing with the hard domain. Hard segment softening (C-NP) is suggested by the board peak centered at 40° C. (ref HDI-BDO-PDMS).

Figure 23:
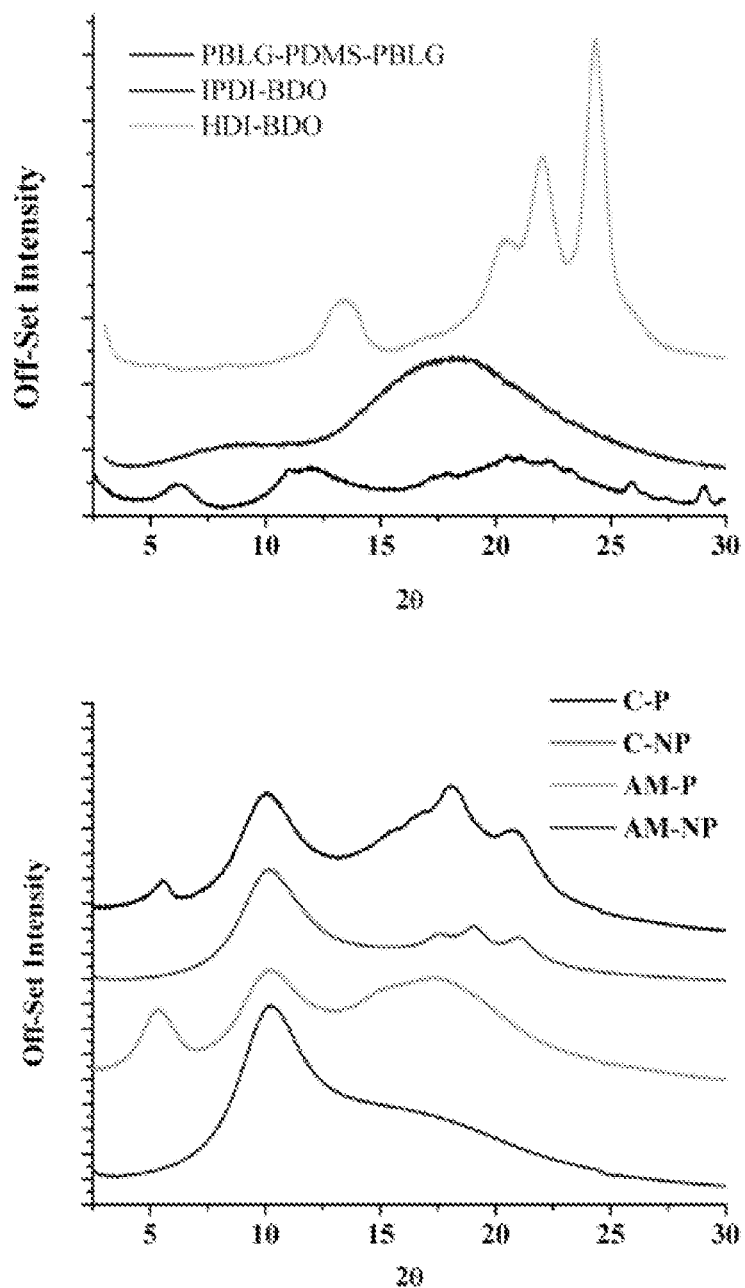
FIG. 23 depicts wide-angle X-ray scattering graphic data of exemplary materials.

Morphological studies, including wide-angle X-ray scattering (WAXS), small-angle X-ray scattering (SAXS) and atomic force microscopy (AFM), can allow for further elucidation of the structural characteristics of the PUUs. Short range ordering examined through WAXS (exemplary data shown in FIG. 23) can reveal a series of pronounced peaks in the region 2Θ=5°-25°. FIG. 23 depicts WAXS patterns of polyurethane compositional materials (left) and polyurethanes (right). The crystalline HDI-BDO scattering pattern reveals three peaks indicative of a triclinic crystal system with d-spacing of 0.431 nm associated with the (100) plane, 0.400 nm with the (110) plane and 0.364 nm with the (111) plane. These intensity maxima correlate well with the peaks observed for both C-P and C-NP; however, with decreased intensities due to lower degree of crystallinity. The scattering pattern for AM-NP shows a broad amorphous halo centered at 2Θ~16° due to the IPDI-BDO hard segment. The spectra for the peptide containing PUUs, C-P and AM-P, reveal a characteristic peak at 2Θ~5.1° that corresponds to β-sheet secondary structure. All PUUs show a peak at 2Θ~10° from the amorphous scattering of PDMS.

Figure 24:
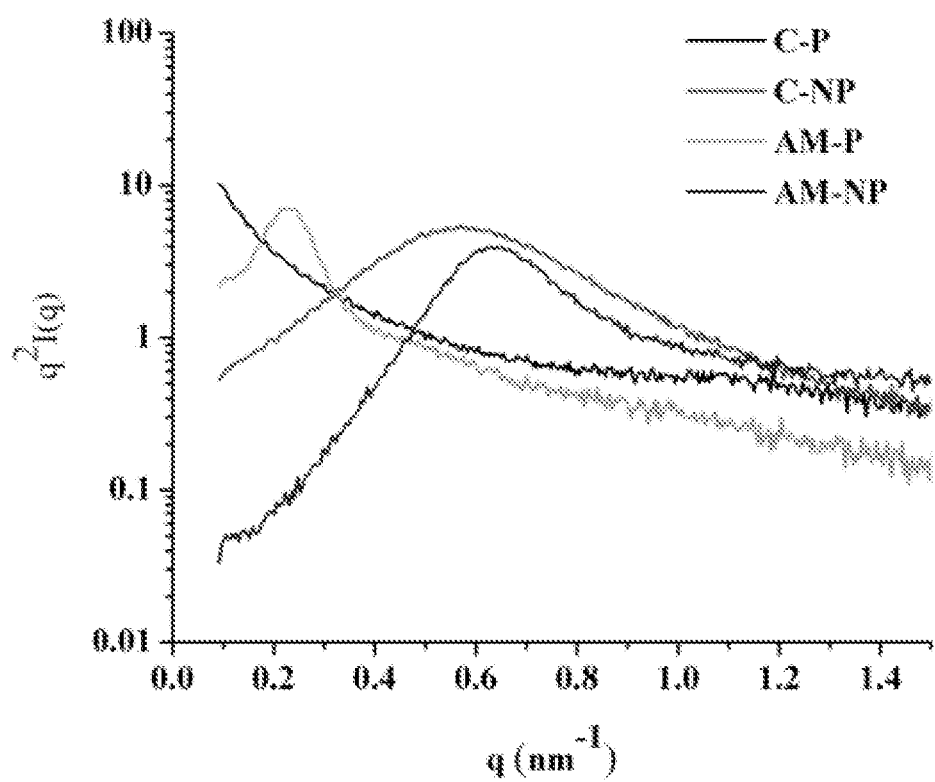
FIG. 24 depicts small-angle X-ray scattering graphic data of exemplary materials.

Small-angle X-ray scattering of FIG. 24 shows a phase separated morphology for C-NP, AM-NP, and AM-P with average domain spacing of 11 nm, 10 nm and 27 nm respectively. With the addition of the peptide, the domain spacing of the IPDI-BDO based PUUs nearly triples. SAXS models typically applied to polyurethanes can assume a two-phase system and consider the scattering peak arise from the electron contrast or electron density differences between the hard and soft phases. However, as suggested by DSC, DMA and WAXS results presented earlier, AM-P is a three-phase system consisting of an amorphous hard and soft domain and an ordered peptide domain. An approach to analyzing the three-phase PUU can be to consider one phase apart of another phase, attributable to electron density similarities, in a pseudo-two-phase system. The electron densities of IPDI-BDO, PBLG and PDMS are 0.632 mol·e⁻/cm³, 0.661 mol·e⁻/cm³, and 0.551 mol·e⁻/cm³ respectively. As a result of the similar electron densities of IPDI-BDO and PBLG, these two phases can be perceived as one large phase by SAXS.

Figure 25:
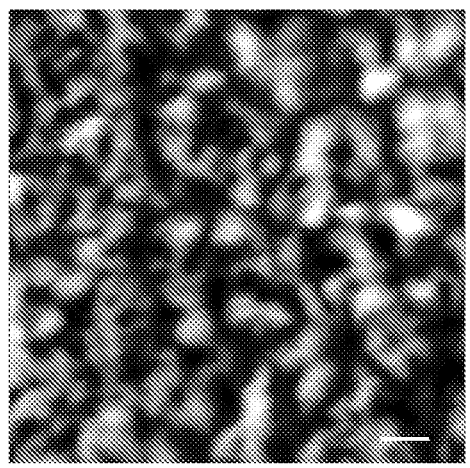
FIG. 25 portrays atomic force microscope phase images of example microtomed polyurethane films.
Figure 25:
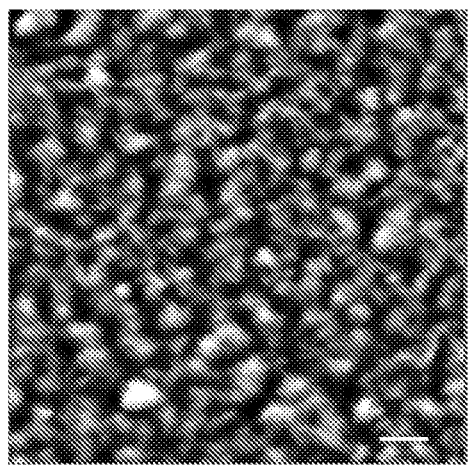
Figure 25:
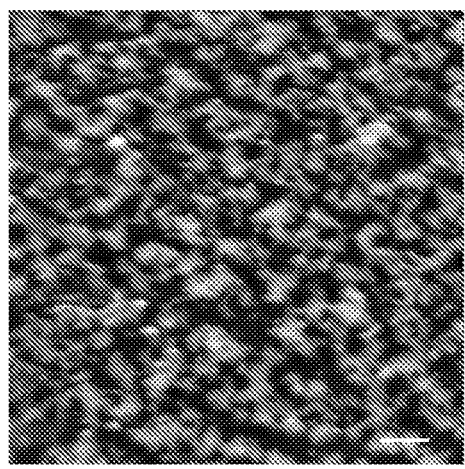
Figure 25:
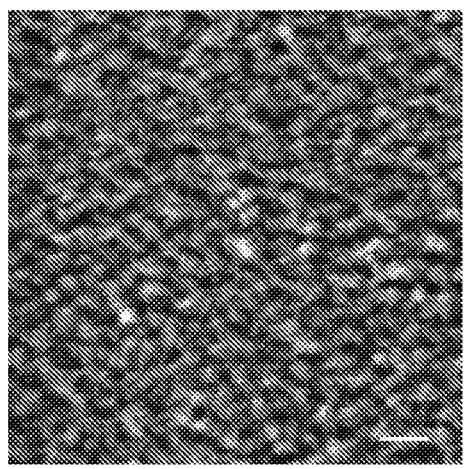

Visual interpretation and confirmation of microphase separation can be achieved by tapping mode AFM. FIG. 25 depicts AFM phase images of microtomed polyurethane films. The images are 1 μm by 1 μm with a 100 nm scale bar. Image (a) is C-P, image (b) is C-NP, image (c) is AM-P, and image (d) is AM-NP. In the phase contrast images the high modulus hard domains and low modulus soft domains can appear as light and dark regions, respectively. The average domain size can be overestimated due to the large AFM tip radius and consequently, may not correspond with the domain spacing given by SAXS. Nevertheless, comparisons can be made within the four samples. As indicated by all experiments presented and further established via AFM, these materials do have a phase separated morphology. Additionally, with the incorporation of the peptidic segment, an increase in domain size can be observed. Furthermore, the addition of the peptidic segment can shift the PUUs from a continuous soft-modulus matrix to a continuous hard-modulus matrix. Such a soft to hard modulus shift directly affects the mechanical properties (vide infra).

Figure 26:
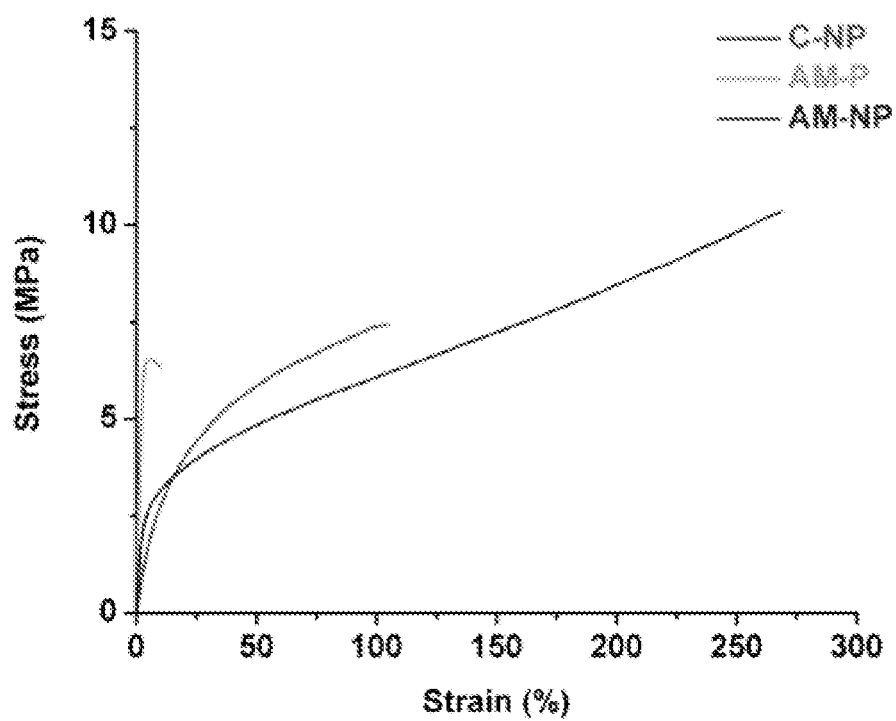
FIG. 26 portrays graphic data concerning tensile results of exemplary material.

Peptidic segment can have an impact on the mechanical properties. In one example, the elongation-at-break, modulus, ultimate tensile strength, and toughness for the PUUs is shown in FIG. 26 and furthered shown in Table 3. In this example, the stress-strain plot of AM-P exhibits a characteristic brittle failure with both low elongation and plastic deformation. The AM-P PUU's modulus is 3.5 times greater than the AM-NP. This generally brittle behavior may be attributed to the shift from a continuous soft-modulus matrix to a continuous hard-modulus matrix. If the peptidic segment is reclassified from the SS to the HS, the HS content increase from 33 wt. % to an effective HS content of 66 wt. %. This change from soft matrix to hard matrix justifies the decrease in elongation and increase in modulus.

TABLE 3

| Polymer | Elongation | Modulus | UTS | Toughness |
| --- | --- | --- | --- | --- |
| C-NP | 124.4 ± 13.2 | 36.1 ± 8.6 | 7.2 ± 1.2 | 5.6 ± 1.4 |
| AM-P | 15.3 ± 9.1 | 252.7 ± 5.6 | 6.6 ± 1.2 | 0.6 ± 0.2 |
| AM-NP | 248.6 ± 14.1 | 71.3 ± 6.4 | 11.0 ± 1.4 | 19. ± 5.1 |

Other materials that mimic structures found in nature include electrospun fibers. One example of materials that include electrospun fibers is an all-organic, stimuli-responsive polymer composite with electrospun fiber fillers.

Stimuli-responsive materials are suitable for a wide range of applications. Stimuli responsive polymer composites can be designed and fabricated using electrospun nanofibers as a filler. Incorporation of 4 wt % of filler into the polymer matrix can increase the tensile storage modulus by about two orders of magnitude. Upon exposure to water, the filler fibers plasticize and no longer provide mechanical reinforcement. The tensile storage modulus subsequently diminishes two orders of magnitude to the value of the neat matrix polymer.

Materials that can change their mechanical properties upon exposure to specific stimuli are suitable for a wide variety of applications including drug delivery, sensors, actuators, and shape-memory materials. There are a number of approaches for imparting stimuli-responsive properties into soft and hard materials upon exposure to a various stimuli. For example, one approach for such dynamic materials is to use stimuli-responsive filler materials for polymer composites. Because the filler can be arranged to be responsible for the dynamic response, it can be blended with a wide variety of polymers to impart stimuli-responsive properties to materials that are otherwise generally mechanically static. In one example, significant mechanical switching in a variety of polymers can be achieved by using cellulose nanowhiskers as filler for polymer nanocomposites. Such an approach is similar to the dermis of a sea cucumber. Another example is an all-organic, stimuli-responsive polymer composite fabricated using an electrospun mat of polyvinyl alcohol (PVA) as the filler. Such an approach can result in a two order of magnitude change in the storage modulus upon exposure to water.

Figure 27:
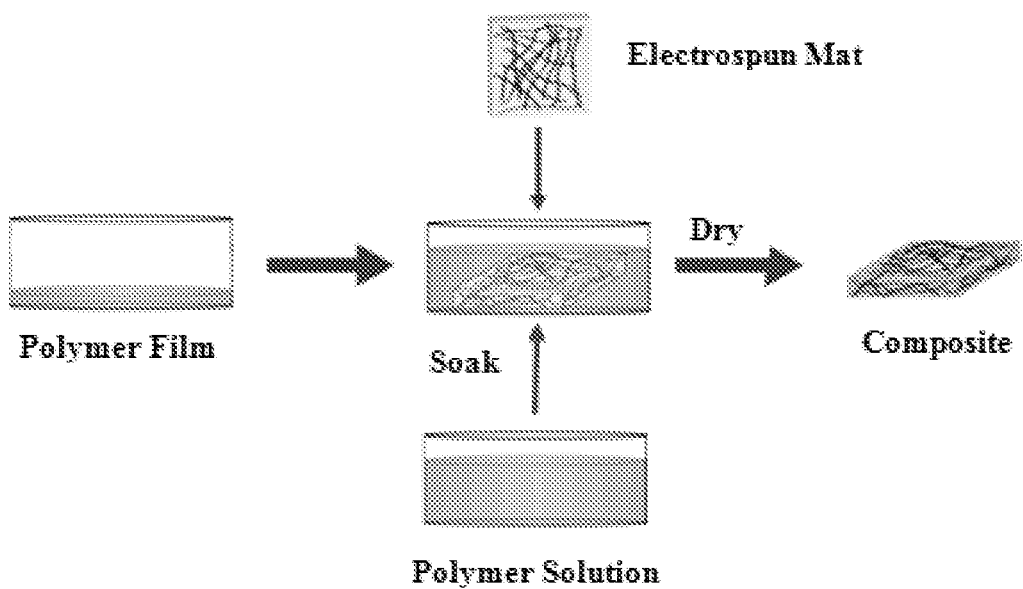
FIG. 27 schematically illustrates an exemplary composite film fabrication process.
Figure 28:
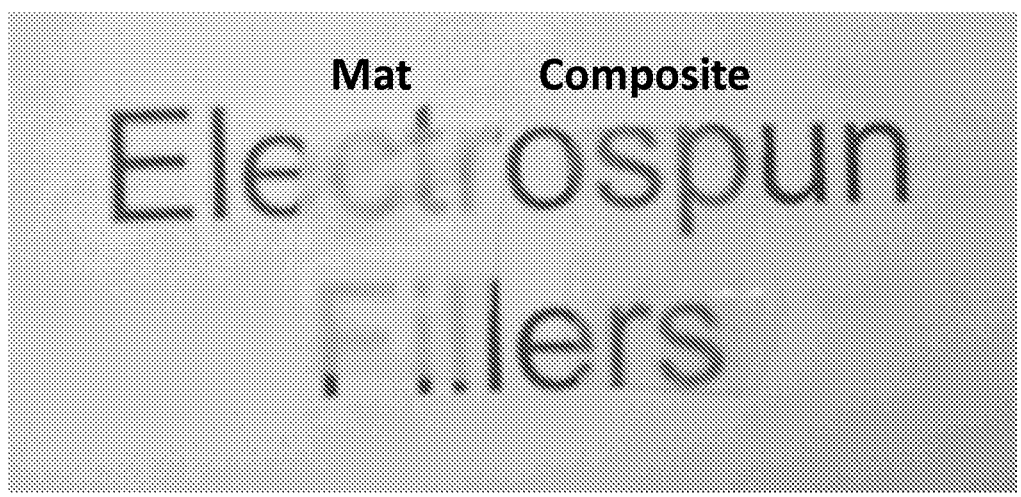
FIG. 28 portrays native electrospun mat and polymer composite film.

In one example, electrospinning can use electrostatic forces to produce continuous polymer nanofibers. Such an approach is suitable for a variety of applications, including cell scaffolds, filtration membranes, and electronic devices to drug delivery vehicles. In electrospinning, fibers can be generated by applying an electric field between a polymer solution and a grounded collector. When the electrostatic force overcomes the surface tension of the polymer solution, a stable jet or "Taylor cone" can be formed. As the jet travels toward the collector, it is constantly subjected to a stretching movement producing nanofibers. Such nanofibers can have a tunable diameter. In addition to applications such as fibrous mats, nanofibers fabricated via electrospinning can also be used as the filler component in polymer nanocomposite materials. Incorporation of electrospun nanofibers into a polymer matrix can increase the strength of the composite films compared to the corresponding neat polymers. Stimuli-responsive polymer composites can be fabricated from electrospun mats. Shape memory and actuation properties of electrospun polymer composites can be achieved using poly(ε-carprolactone) and carbon nanofibers respectively as filler materials. FIG. 27 schematically illustrates a composite film fabrication processes. FIG. 28 is a photograph of the native electrospun mat and polymer composite film showing the increase in transparency of the composite film. U.S. patent application Ser. No. 12/571,043, filed on Sep. 30, 2009, and titled "Benign Solvents for Forming Protein Structures" describes methods of forming mates and films, which is incorporated by reference as if fully rewritten herein.

Materials for use in forming electrospun polymer composites include, but are not limited to, 1:1 ethyleneoxide/epichlorohydrin copolymer (EO-EPI) Polymer composite films comprising a rubbery 1:1 ethyleneoxide/epichlorohydrin copolymer (EO-EPI) as the matrix and electrospun polyvinyl vinyl alcohol (PVA) can be fabricated to realize stimuli-responsive composite materials. EO-EPI can be used as the matrix because it has a low storage modulus and does not swell substantially in water. Furthermore, due to the hydrogen bond accepting nature of the ether functionality of the copolymer, strong interaction between the alcohol groups of the PVA filler and the polymer is expected. For the filler, PVA can be chosen due to its high strength (storage modulus ~1.6 GPa for the mat), fiber diameter in the nanometer range when electrospun, and hydrolytic stability of the fibers upon treatment with methanol. Treating the PVA mat with methanol can prevent the dissolution of the electrospun mat in water by increasing the crystallinity of the fibers that also results in an increase in the storage modulus of the mat.

Absorbance measurements can be taken on a Perkin-Elmer Lambda 1050 spectrometer. DMTA can be performed on a TA Instruments DMA Q800 operating in tensile mode. SEM can be performed on a JOEL JSM-6510LV microscope. Electrospinning can be performed on with a number of suitable apparatus and procedures. For example, aqueous solution of PVA (99% hydrolysis) can be prepared by stirring a specified amount of polymer in water (10 wt %) at 80° C. until the polymer is fully dissolved. Upon cooling, 1-2 drops of the surfactant Triton-X100 can be added to reduce the surface tension and stirred for 10-15 min. The solution can be loaded into a syringe and subjected to the electro spinning conditions of a flow rate of 1.0 mL/hr, 20 kV, and 20 cm tip to collector distance. After formation of the mat (typically 1 hr), the mat can be removed from the collector and submerged into methanol for 24 hr. The mat can be dried under vacuum and stored in a desiccator until use.

With reference again to FIG. 27, an exemplary fabrication process for the polymer composites is schematically shown. To obtain uniform films, an electrospun PVA mat can be placed into an EO-EPI solution (100 mg/mL in toluene) in a Teflon mold. The solution can be dried under ambient conditions and removed from the mold, yielding a uniform film ~300 μm thick. As noted above with reference to FIG. 28, composite films can be significantly more transparent than the corresponding electrospun mat, which can indicate strong matrix-filler interaction, which is necessary for mechanical reinforcement.

Figure 29:
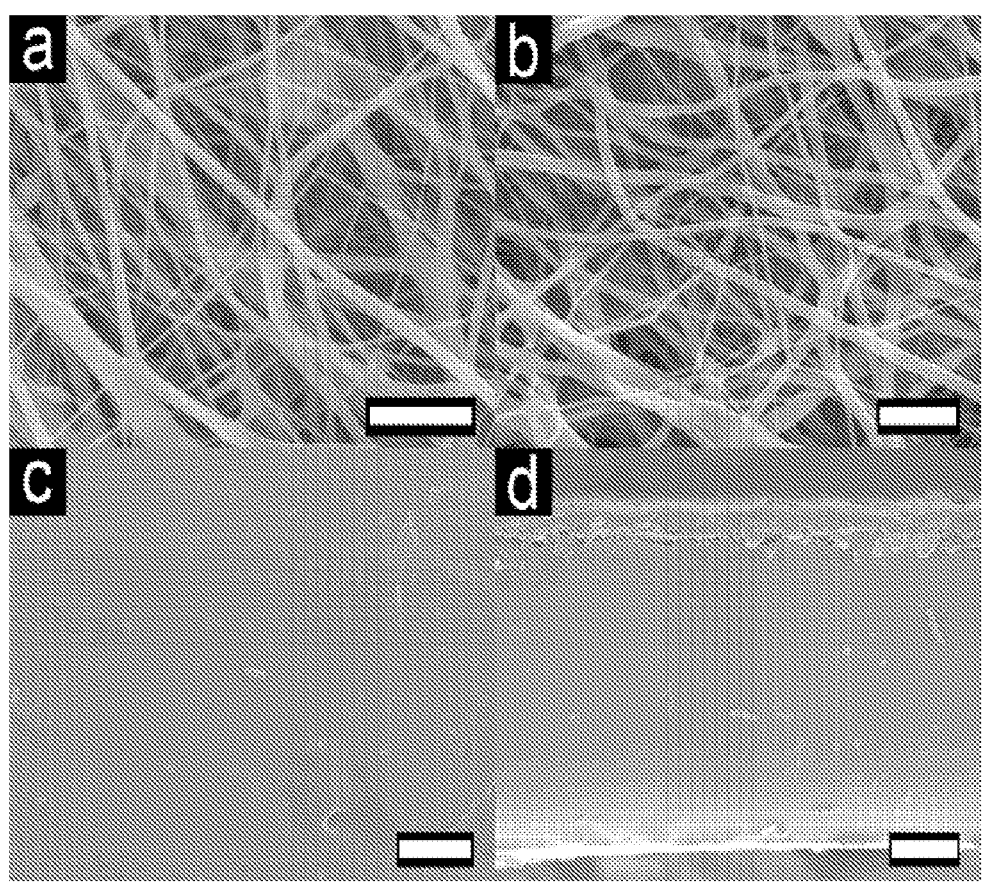
FIG. 29 depicts scanning electron microscope images of various exemplary materials.

FIG. 29 depicts SEM images of (a) native electrospun PVA mat (scale bar 10 μm), (b) PVA mat after methanol soaking (scale bar 10 μm), (c) surface of the composite film (scale bar 75 μm), and (d) cross-section of the composite film (scale bar 75 μm). As will be understood, SEM can be used to review the structure of the composite films. In one example, upon electrospinning, the PVA mat was found to consist of one-dimensional fibers with a diameter of 508±216 nm. Fiber diameter distribution can be controlled by electrospinning conditions and the PVA solution properties. Methanol soaking can increase the fiber diameter to 716±197 nm. Composite films were found to be smooth on the surface indicating the electrospun mat is fully incorporated into the film. Cross sectional SEM revealed a sandwich-type structure in the composite film with regions of neat polymer on both sides of the electrospun mat. The EO-EPI polymer also appears to be well interfaced with the electrospun mat with only a few regions of delamination.

Figure 30:
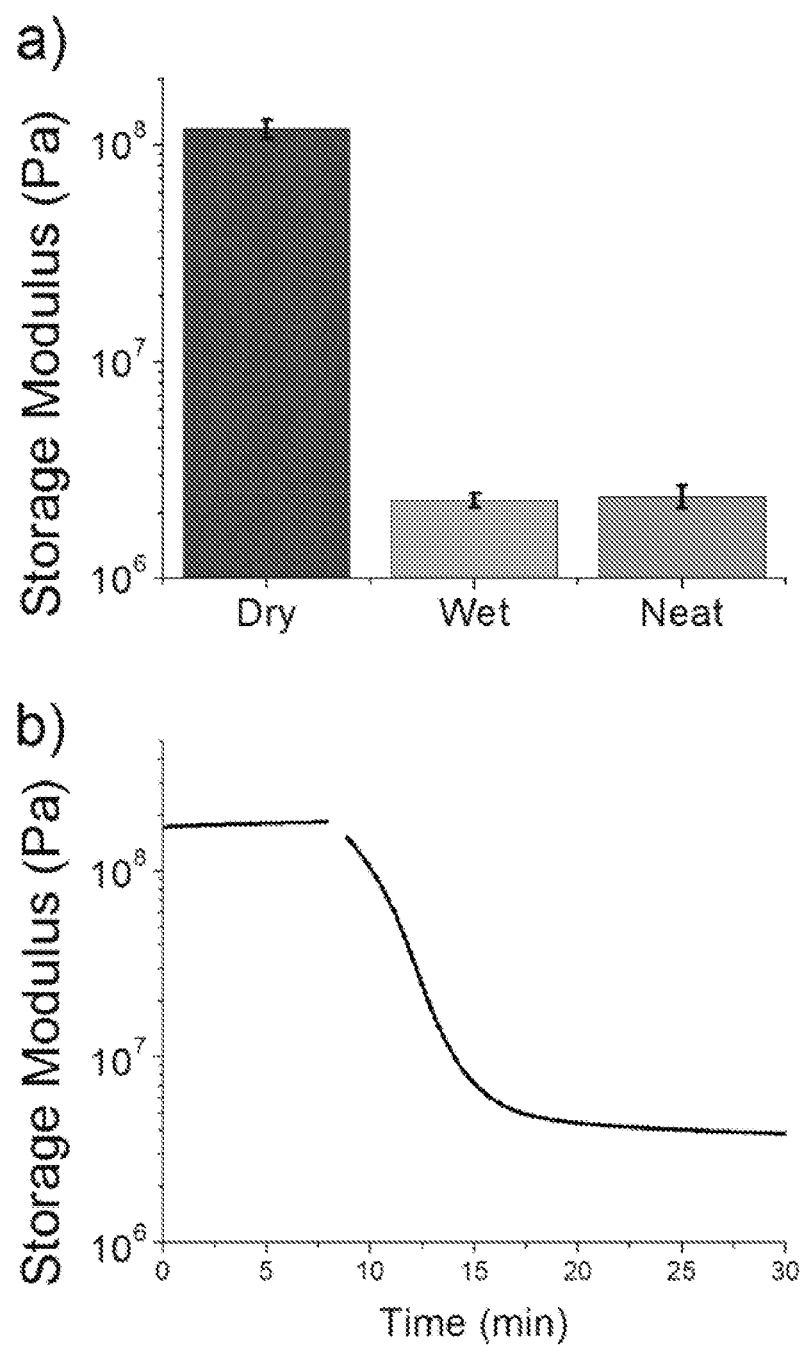
FIG. 30 portrays graphic data concerning tensile results of exemplary material.

Evaluating the stimuli-responsive mechanical behavior can be achieved by conducting dynamic mechanical thermal analysis (DMTA) to obtain, for example, tensile storage modulus (E') in the dry and wet state. In FIG. 30, graph (a) depicts tensile storage modulus of EO-EPI with PVA composite dry, EO-EPI with PVA composite wet, and the neat EO-EPI polymer dry; and graph (b) depicts storage modulus change as a function of time after the addition of water, where the line break in the plot corresponds to the addition of water.

At room temperature, EO-EPI is above its glass transition temperature ($T_g$=−35° C.) and thus in a generally rubbery state resulting in a low tensile storage modulus of E'=2.4±0.3 MPa. With the inclusion of 4 wt % of PVA electrospun mat, the tensile storage modulus increased two orders of magnitude to E'=118±12 MPa. In one example, subsequent to exposure to water, the tensile storage modulus was found to dramatically decrease to E'=2.3±0.2 MPa, which is similar to the tensile storage modulus of the neat polymer, without substantial increase in swelling. At room temperature neat EO-EPI swells about 19.3±1.9% w/w in water, while the composite swells about 28.3±3.6% w/w. The modulus change occurs over the course of 10-20 minutes. In the composite film, upon uptake of water, the PVA fibers soften so that no reinforcement to the polymer matrix occurs. Since the PVA fibers no longer reinforce the composite film, the mechanical properties return to those of the EO-EPI matrix. Drying of the film did not restore the storage modulus fully resulting in a one-directional responsive system.

Figure 31:
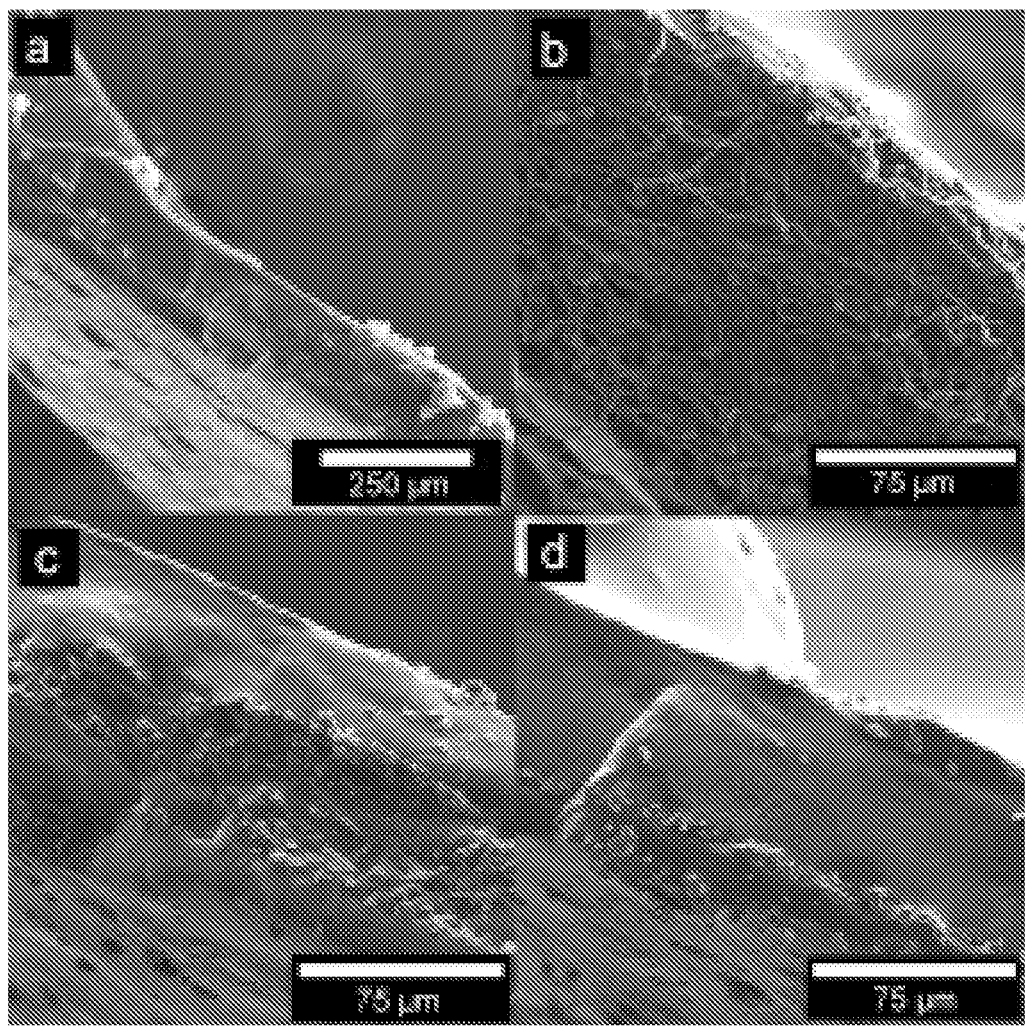
FIG. 31 depicts scanning electron microscope images of various exemplary materials under various conditions.

Whether there was any significant delamination of the matrix and filler contributing to the stimuli-responsive softening can be determined by studying cross-sectional SEM images of dried composite material after water soaking. FIG. 31 depicts SEM images of (a) composite film after water immersion and drying; (b) upper left portion of image (a); (c) middle portion of image (a); and (d) bottom right portion of image (a). Significant delamination between the filler and matrix is not observed. Thus, irreversible loss of crystallinity is likely the most significant factor in the reduction of storage modulus and one-directional behavior of composites.

Figure 32:
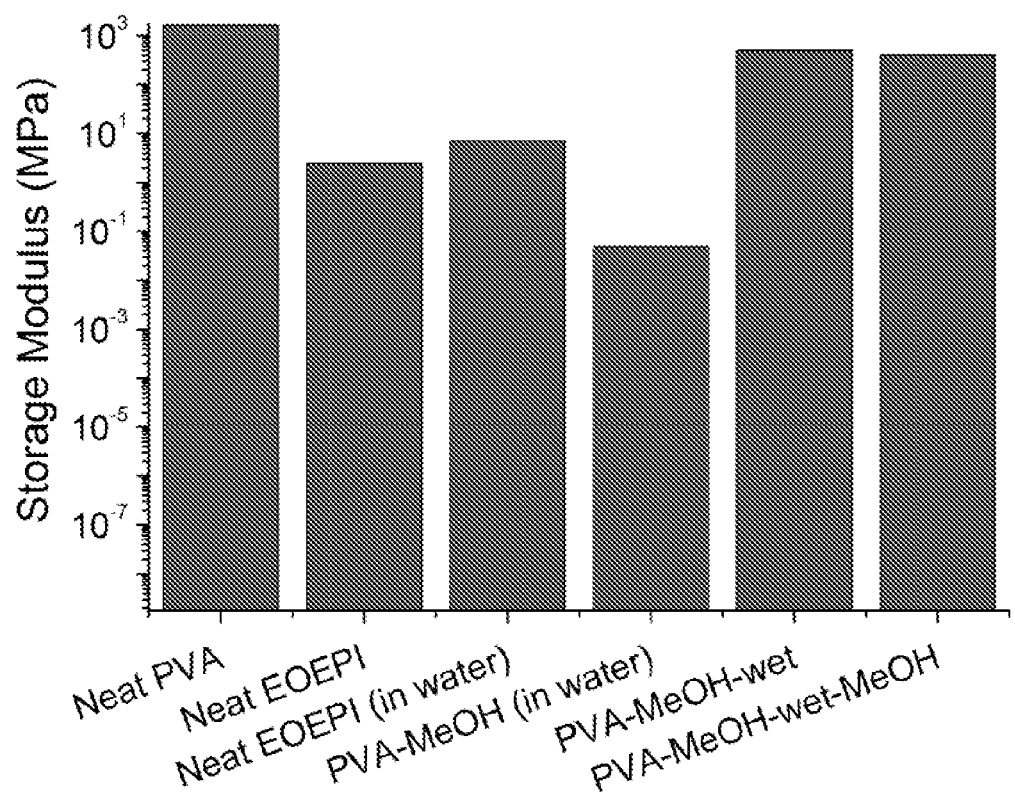
FIG. 32 portrays graphic data concerning DMTA analysis of individual components.

One-directional behavior of composites can further be determined by DMTA analysis of individual components. One example of such an analysis is illustrated in FIG. 32, which depicts tensile storage modulus of individual components of a composite. At room temperature, neat PVA is below its glass transition temperature (75° C.) and thus in a glassy state resulting in a higher storage modulus (~1700 MPa). In one example, a PVA mat tested in water submersion had a storage modulus decreased about five orders of magnitudes to ~0.05 MPa. This explains the softening of wet PVA causing an overall reduction of storage modulus of the composite. A substantial increase of storage modulus (~500 MPa) is noticed after drying of water soaked PVA mat. Inhibition of water movement out of PVA through the EO-EPI matrix can be accounted for preventing restoration of the storage modulus of composite resulting in a one-directional responsive system.

Figure 33:
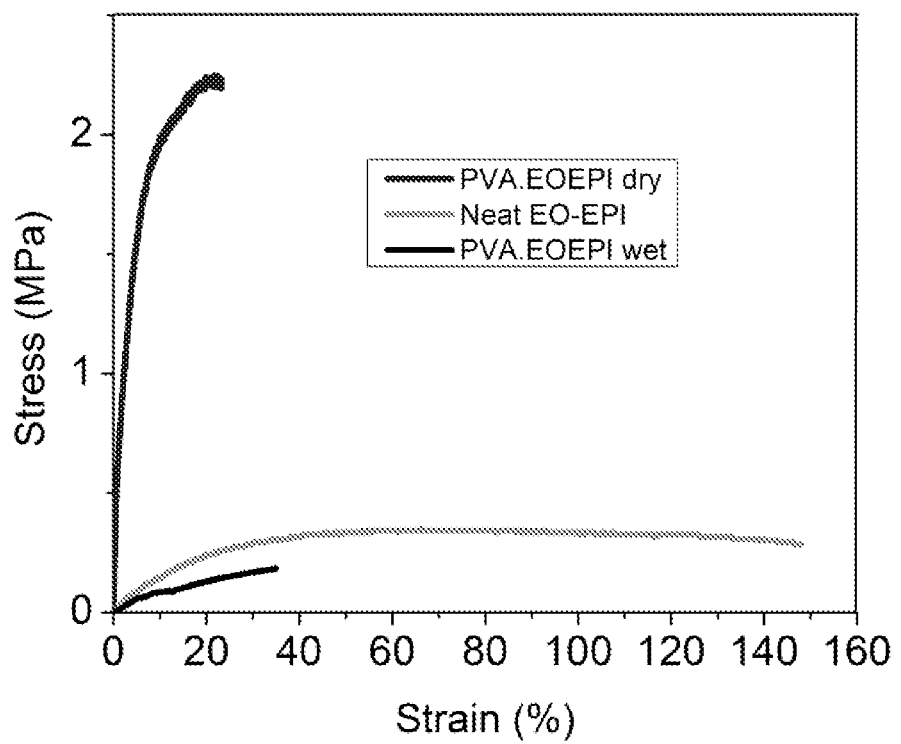
FIG. 33 portrays graphic data concerning tensile results of exemplary material.

FIG. 33 depicts tensile stress-strain curves for neat EO-EPI, EO-EPI/PVA composites when dry, and EO-EPI/PVA composites when whet. Differential scanning calorimetry (DSC) reveals a general loss of crystallinity of PVA mat in the composite after drying of water soaked composite. Neat PVA mat after water soaking and drying regained 77% of crystallinity. Thus, loss of crystallinity can account for the significant reduction of storage modulus and one-directional behavior of composites. As noted above, neat EO-EPI is in a rubbery state at room temperature and shows higher elongation at break (~150%) and lower tensile strength (~0.33 MPa). The reinforcement of polymer matrix in the composite is shown by its higher elastic modulus (~104 MPa), tensile strength (~2.45 MPa) and toughness (~0.42 MJ/m$^3$). As will be understood, strong interaction between the high modulus, crystalline PVA electrospun mat and the rubbery EO-EPI matrix can lead to effective stress transfer and enhancement of the overall strength of the material.

The fabrication and mechanical properties of an all-organic stimuli-responsive composite film can be affected by how it is formed. An electrospun mat of PVA can be incorporated into a soft polymer (EO-EPI) matrix by mixing the mat with a polymer solution and evaporating the solvent. The resulting composite film can be more transparent than the initial mat indicating good matrix-filler interactions. Upon the incorporation of 4 wt % of PVA mat as filler, the storage modulus can increase two orders of magnitude. Exposure to water can plasticize the PVA fibers. Such plasticization can negate the reinforcement effect of fiber inclusion. The hydrated composite film can have a tensile storage modulus equivalent to the neat dry polymer, which can demonstrate the ability to change the storage modulus upon exposure to a specified trigger. Since electrospinning is a robust technique able to form nanofibers from a wide variety of polymers to be used as fillers, this general approach can form stimuli-responsive composites using an assortment of stimuli.

Figure 34:
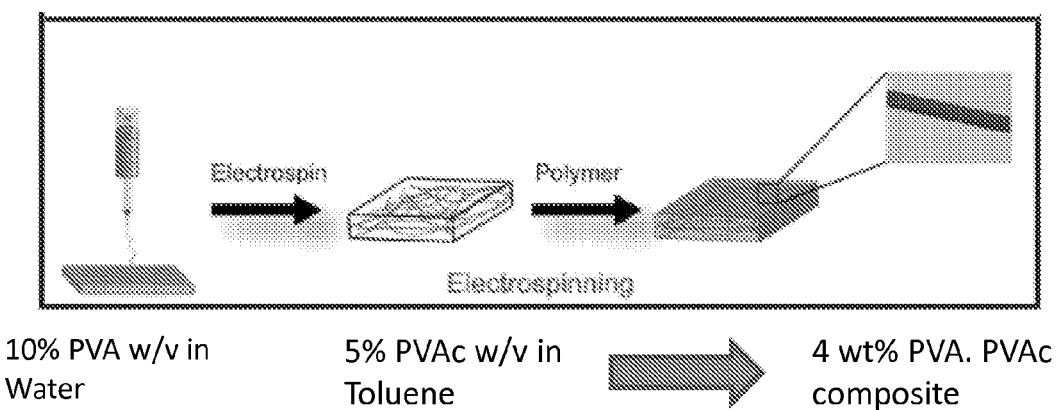
FIG. 34 schematically illustrates an exemplary electrospinning process.
Figure 35:
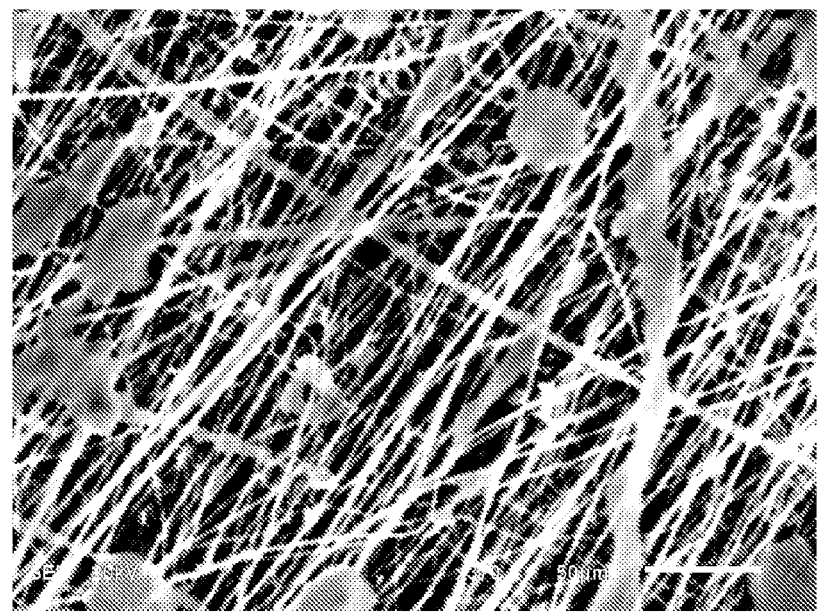
FIG. 35 depicts a scanning electron microscope image of an exemplary material.
Figures 36, 37:
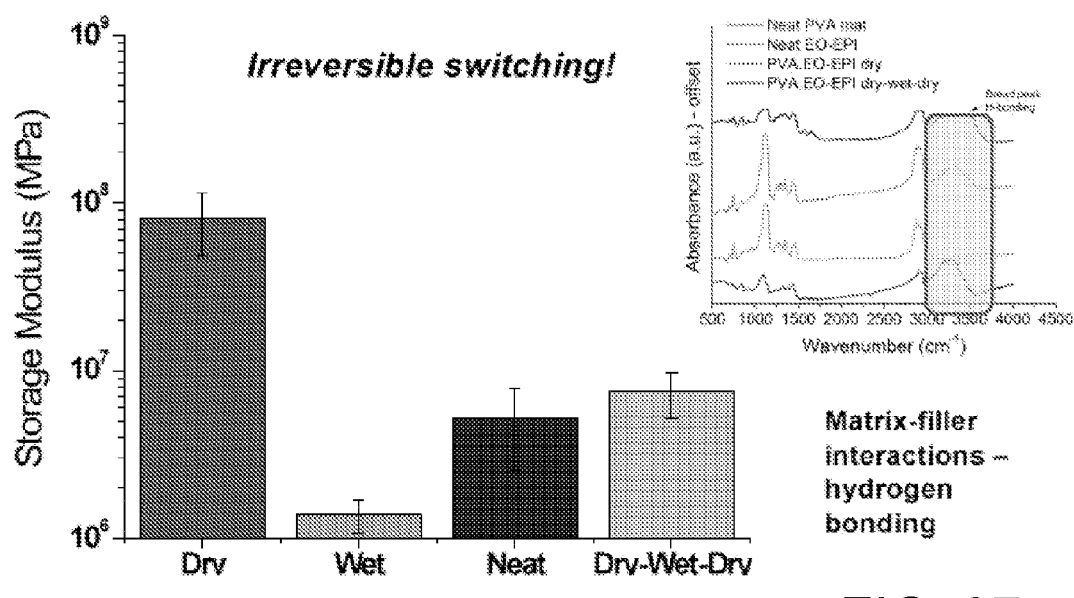
FIG. 36 portrays graphic data concerning storage modulus of exemplary materials/conditions.
FIG. 37 portrays graphic data concerning absorbance of exemplary materials/conditions.

As previously noted, an all-organic composite with electrospun fibers can have any number of uses such as, for example, a controlled drug delivery system or for optical modulation. In one example, PVA can be used as a filler in a EO-EPI matrix at percent weights of 4% and 15% respectively. In one example, PVA can be used as a filler in a PVAc matrix at percent weights of 4% and 15% respectively. As illustrated schematically in FIG. 34, an electrospinning process can be used to form a 4 wt % PVA/PVAc composite from 10% PVA w/v in water and 5% PVAc w/v in toluene. The resulting mat and composite are shown in FIG. 28. FIG. 35 is an SEM image of the 10% PVA w/v in water. FIGS. 36 and 37 are charts depicting storage modulus and absorbance of PVA/EO-EPI (4%) composites.

Figure 38:
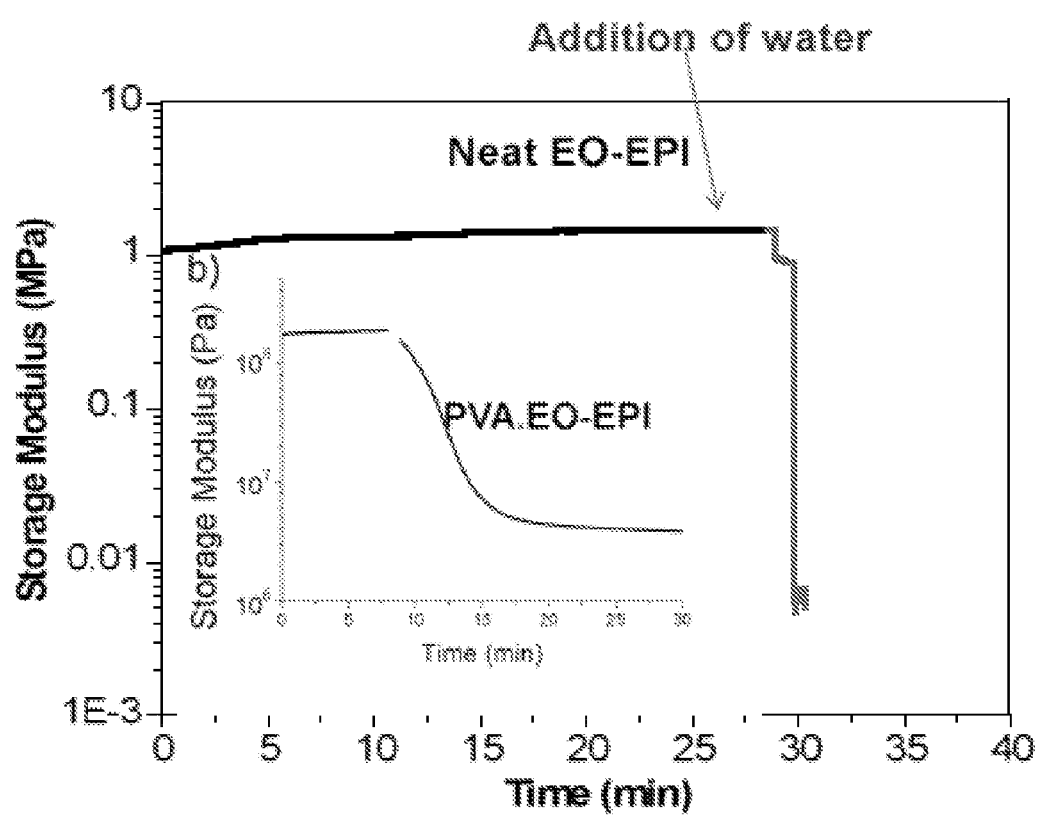
FIG. 38 portrays graphic data concerning storage modulus of exemplary materials/conditions.
Figure 39:
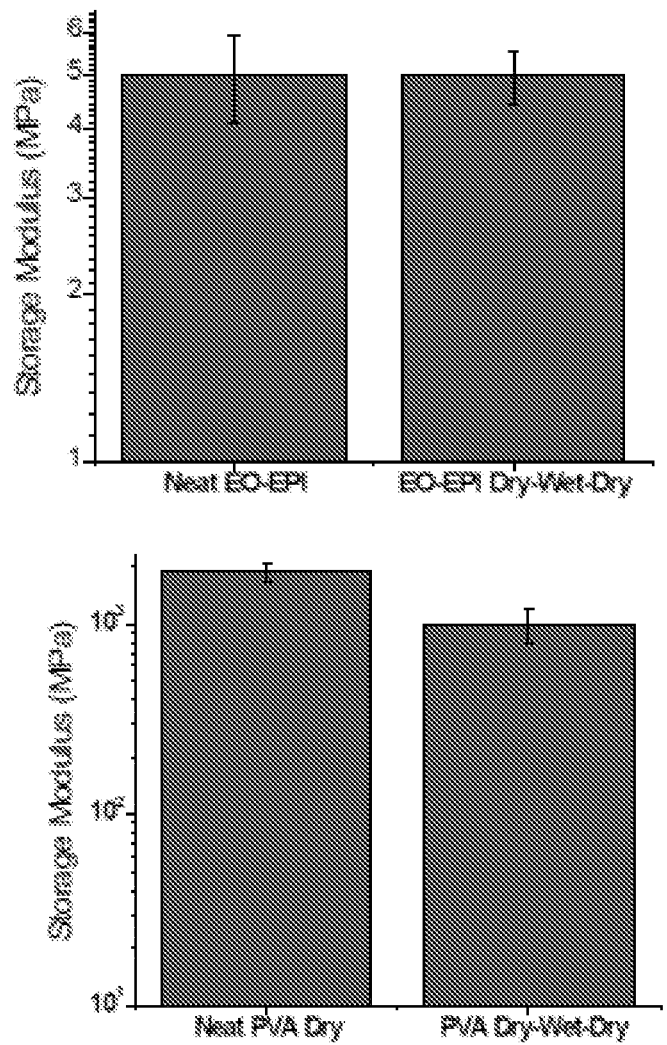
FIG. 39 portrays graphic data concerning storage modulus of exemplary materials/conditions.
Figure 40:
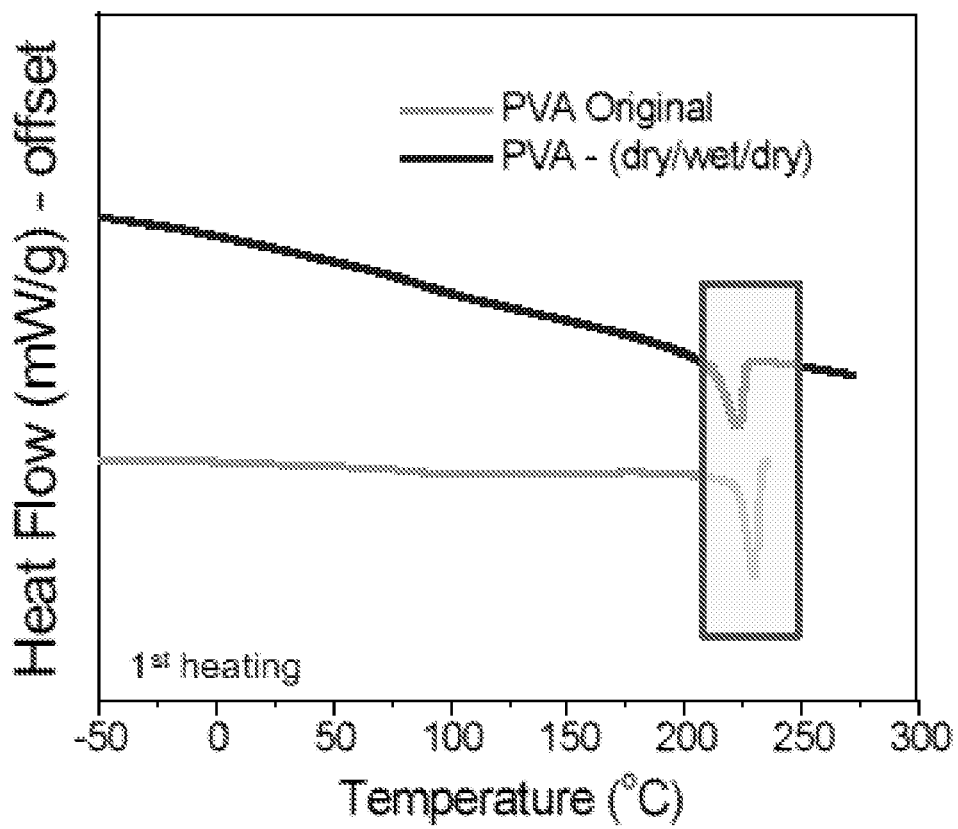
FIG. 40 portrays graphic data concerning heat flow of exemplary materials/conditions.
Figure 41:
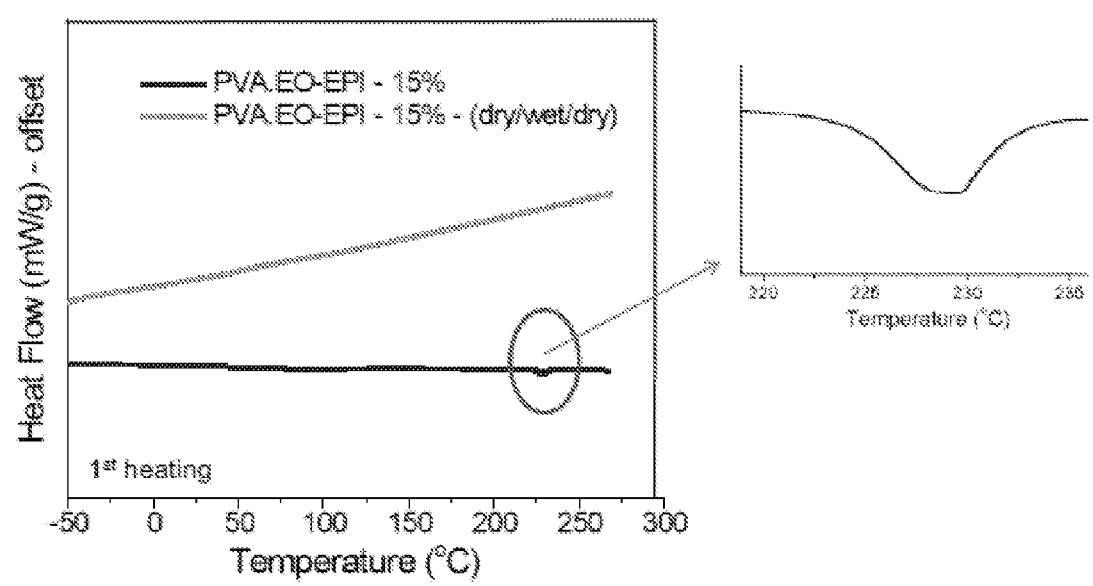
FIG. 41 portrays graphic data concerning heat flow of exemplary materials/conditions.
Figure 42:
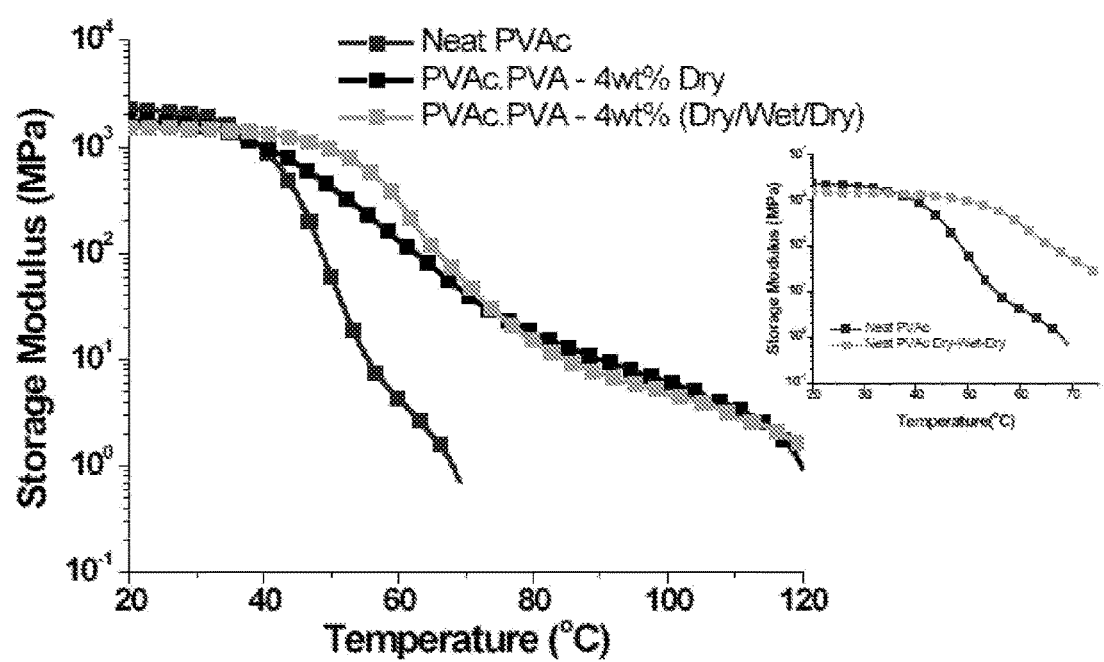
FIG. 42 portrays graphic data concerning storage modulus of exemplary materials/conditions.
Figure 43:
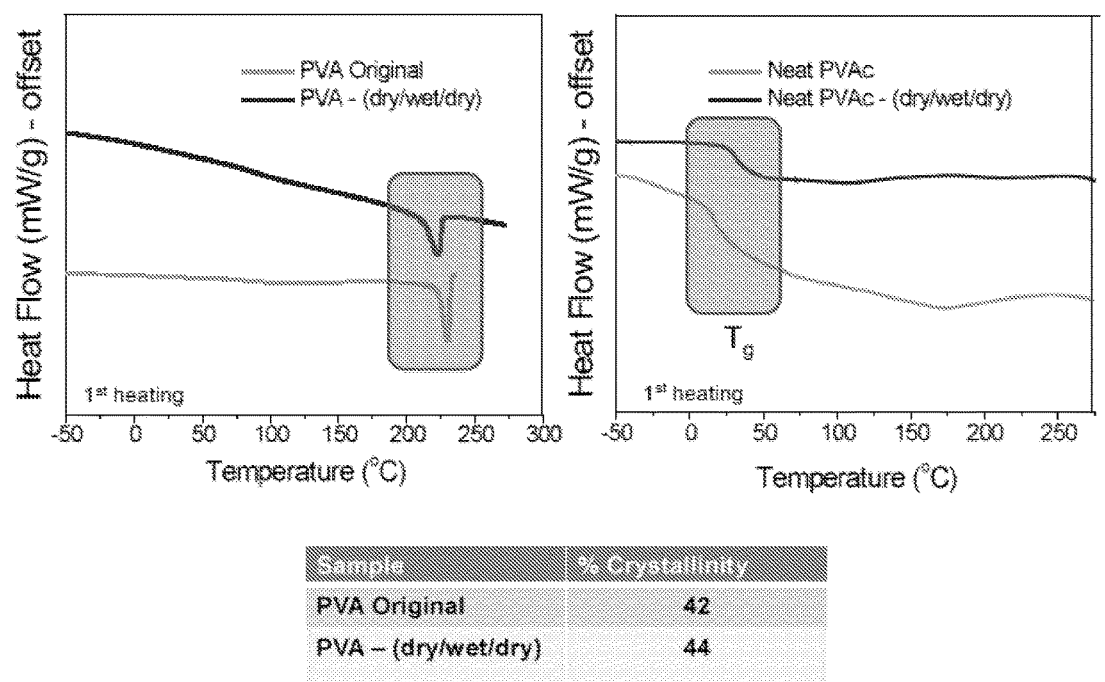
FIG. 43 portrays graphic data concerning heat flow of exemplary materials/conditions.
Figure 44:
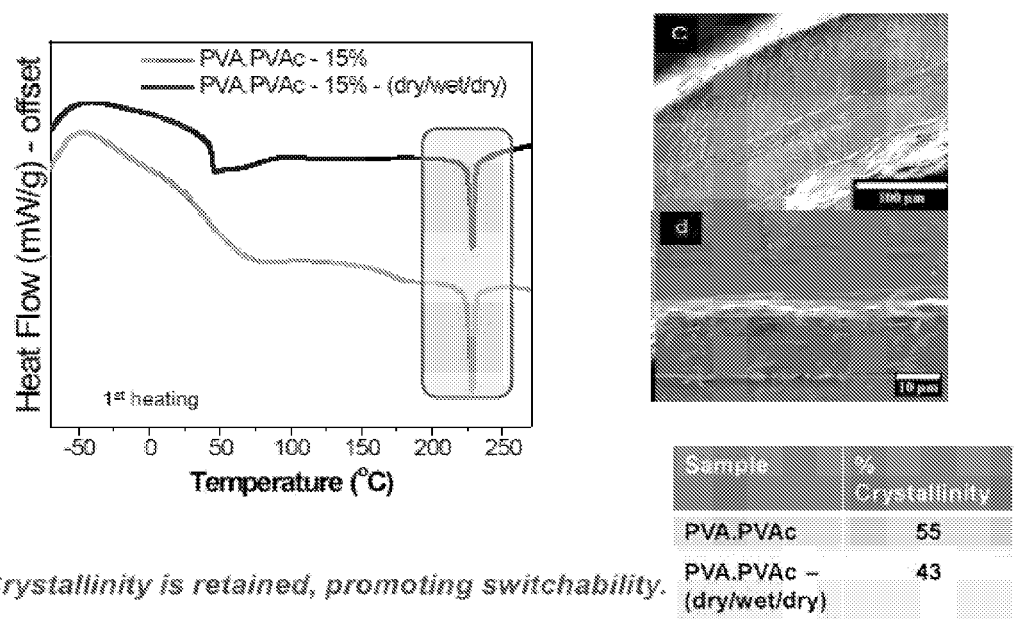
FIG. 44 portrays graphic data concerning heat flow of exemplary materials/conditions, as well as depicts a scanning electron microscope image of an exemplary material.
Figure 45:
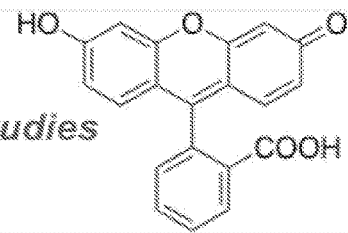
FIG. 45 illustrates set-up particulars of an exemplary dye release study.
Figure 45:
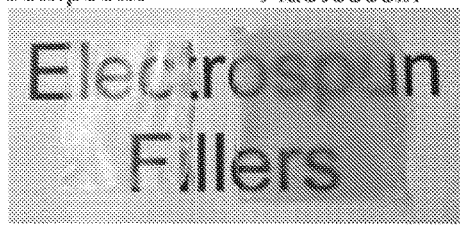
Figure 45:
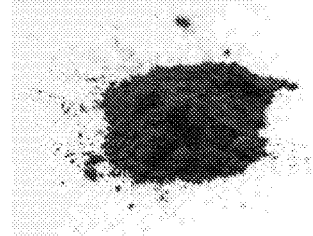
Figure 45:
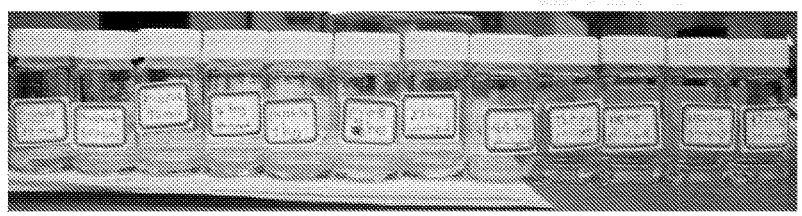
Figure 46:
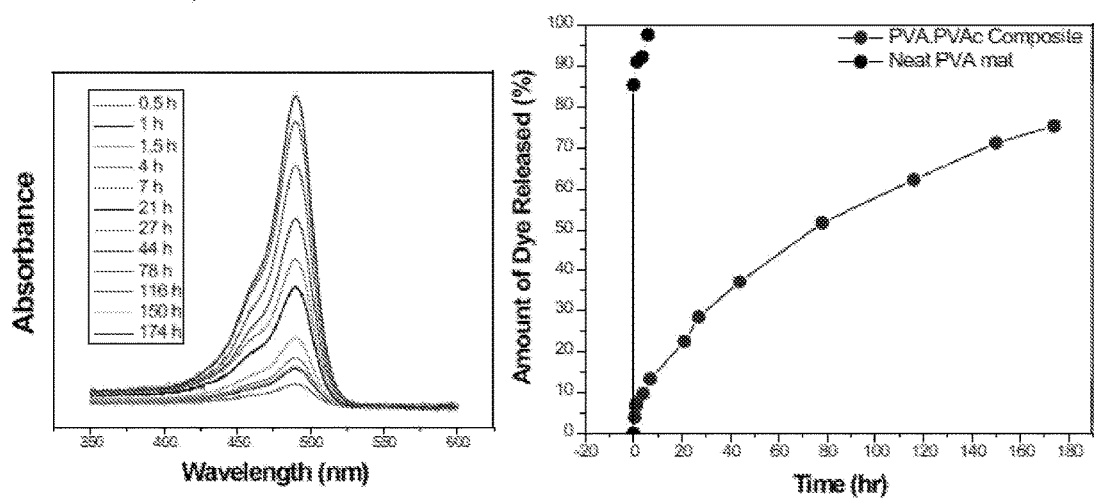
FIG. 46 portrays results of an exemplary dye release study.

FIGS. 38 and 39 depict exemplary effects of water on a PVA/EO-EPI composite. The decrease in the modulus for neat EO-EPI is more rapid than for the composite. Also, PVA reduces the rate of the decrease in modulus. FIGS. 40 and 41 depict exemplary heat flow for a composite. As is shown in FIG. 41, a crystalline peak is absent in the dry/wet/dry composite. A representative sample, of a PVA/EO-EPI composite used for crystalline analysis is shown in FIG. 31. FIG. 42 depicts an exemplary relationship between storage modulus and temperature for PVA/PVAc composites. FIGS. 43 and 44 depict the results of PVA and PVAc crystallinity analysis. FIGS. 45 and 46 depict the set-up and results of a dye release study, indicating that composites as described herein can be utilized for controlled drug release.

Figure 47:
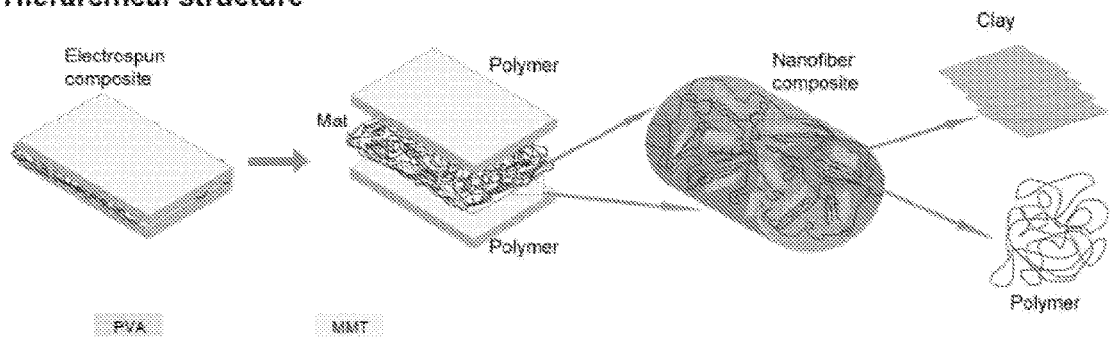
FIG. 47 schematically illustrates an exemplary composite forming process.
Figure 48:
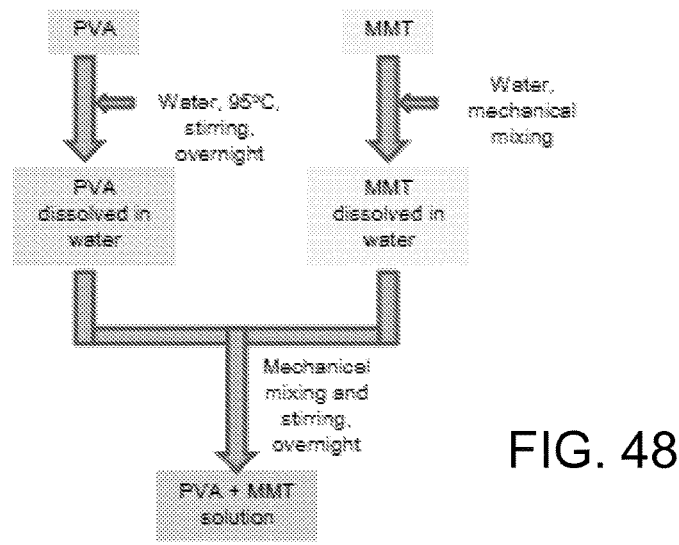
FIG. 48 schematically illustrates an exemplary composite forming process.
Figure 49:
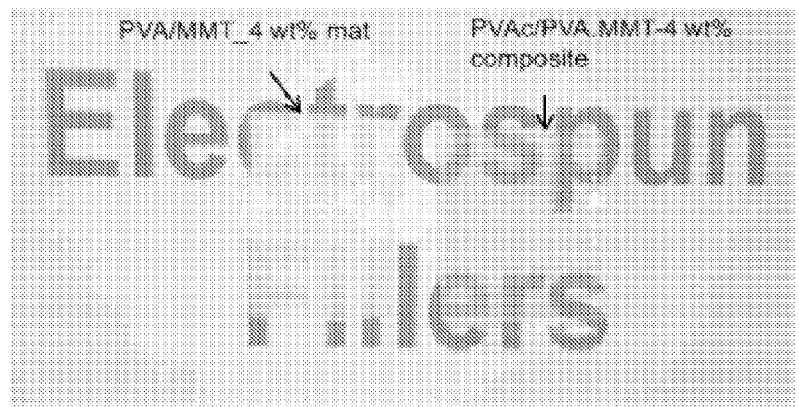
FIG. 49 depicts a photograph image of an exemplary material.
Figure 50:
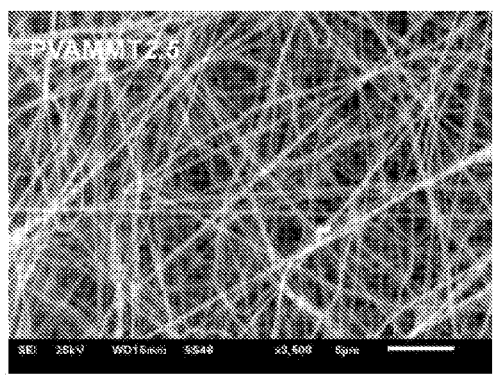
FIG. 50 depicts a scanning electron microscope image of an exemplary material.
Figure 51:
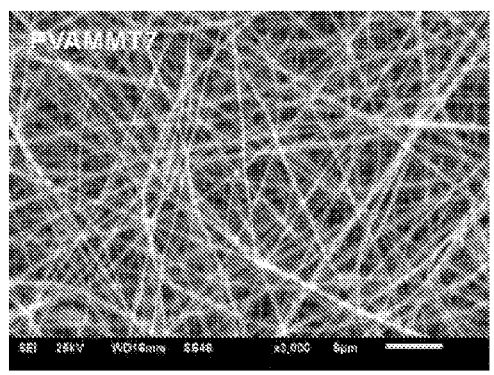
FIG. 51 depicts a scanning electron microscope image of an exemplary material.
Figure 52:
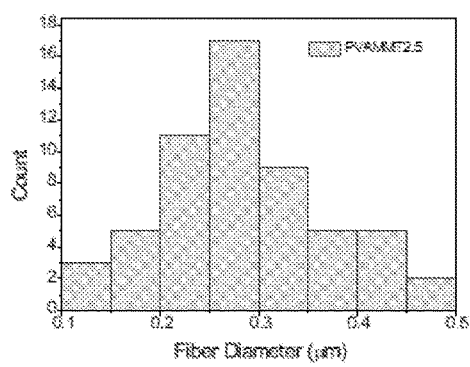
FIG. 52 portrays graphic data concerning fiber diameter results of exemplary material.
Figure 53:
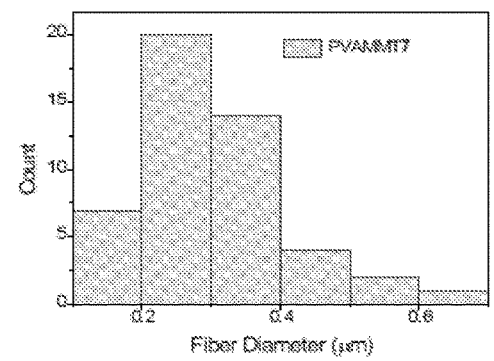
FIG. 53 portrays graphic data concerning fiber diameter results of exemplary material.

FIGS. 47 and 48 illustrate another method of forming a composite. A composite can be formed from PVA and a montmorillonite (MMT). The PVA can be placed in water at 95° C. and stirred to dissolve the PVA in water. MMT can be placed in water and mixed mechanically to dissolve the MMT in water. The dissolved PVA and MMT can be mechanically mixed to form a PVA and MMT solution from which a nanofiber composite can be electrospun. PVAc can also be used in place of PVA. FIG. 49 are photographs of PVA/MMT composite (at 4 wt %) and of PVAc/MMT composite (at 4 wt %). FIGS. 50 and 51 are SEM image of PVA/MMT composites. FIGS. 52 and 53 are charts of the fiber diameter of PVA/MMT composites.

Figure 54:
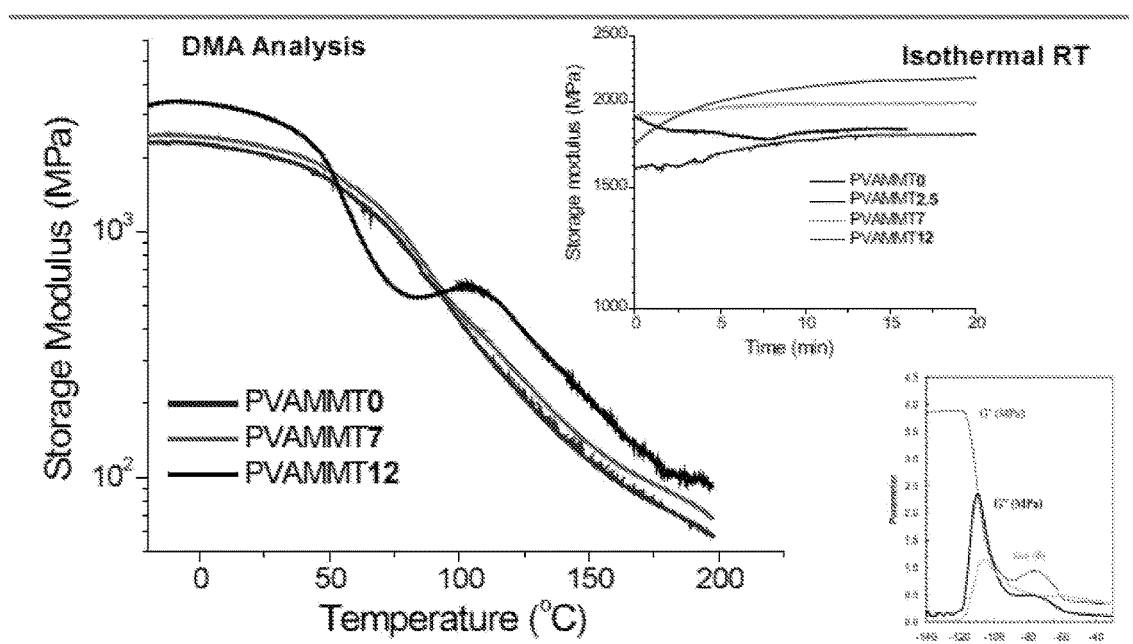
FIG. 54 portrays graphic data concerning exemplary mechanical behavior of PVA/MMT composites.
Figure 55:
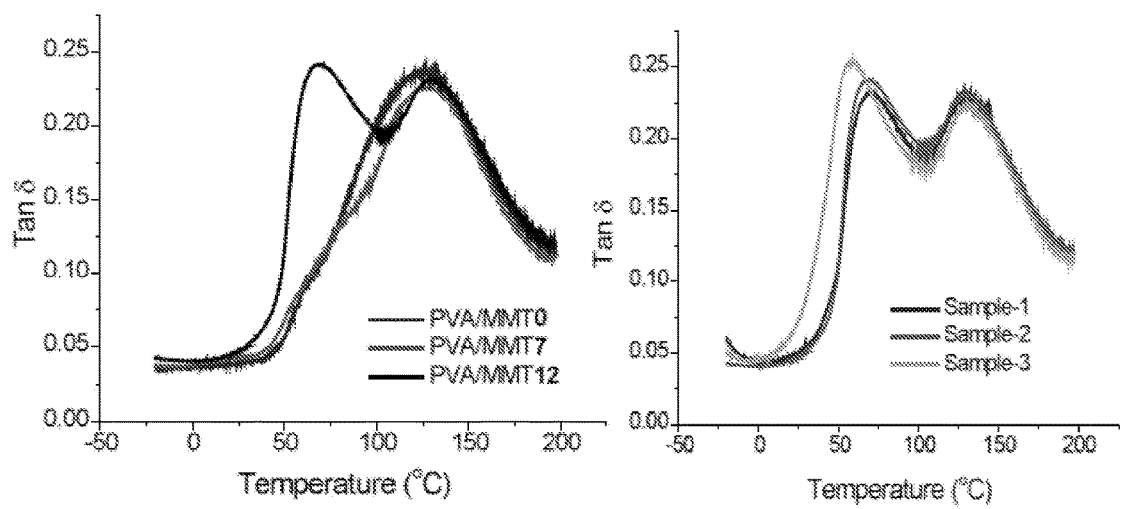
FIG. 55 depicts exemplary tan δ analysis of PVA/MMT composites.
Figure 56:
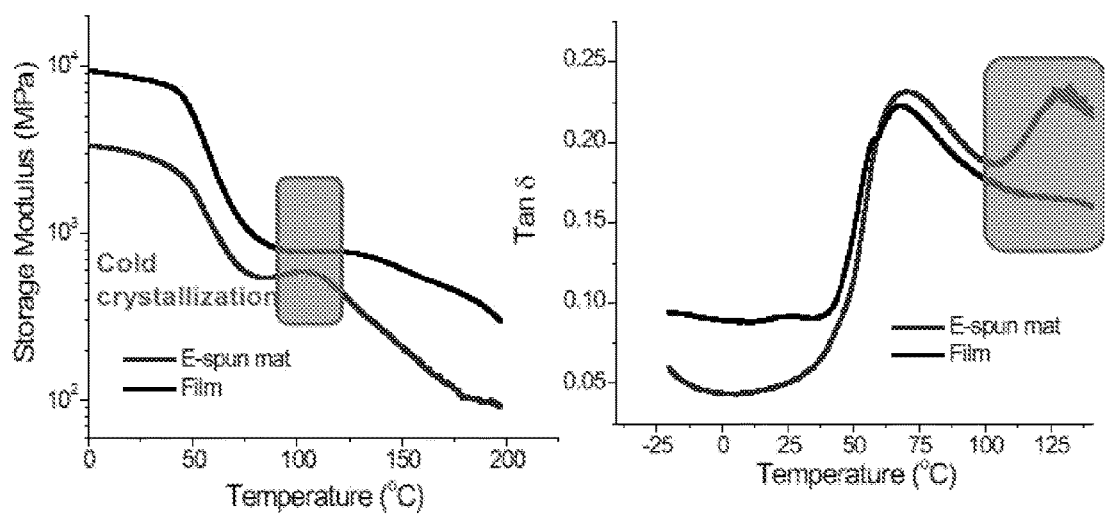
FIGS. 56 and 57 compare graphic data of PVA/MMT electrospun mats to films.
Figure 57:
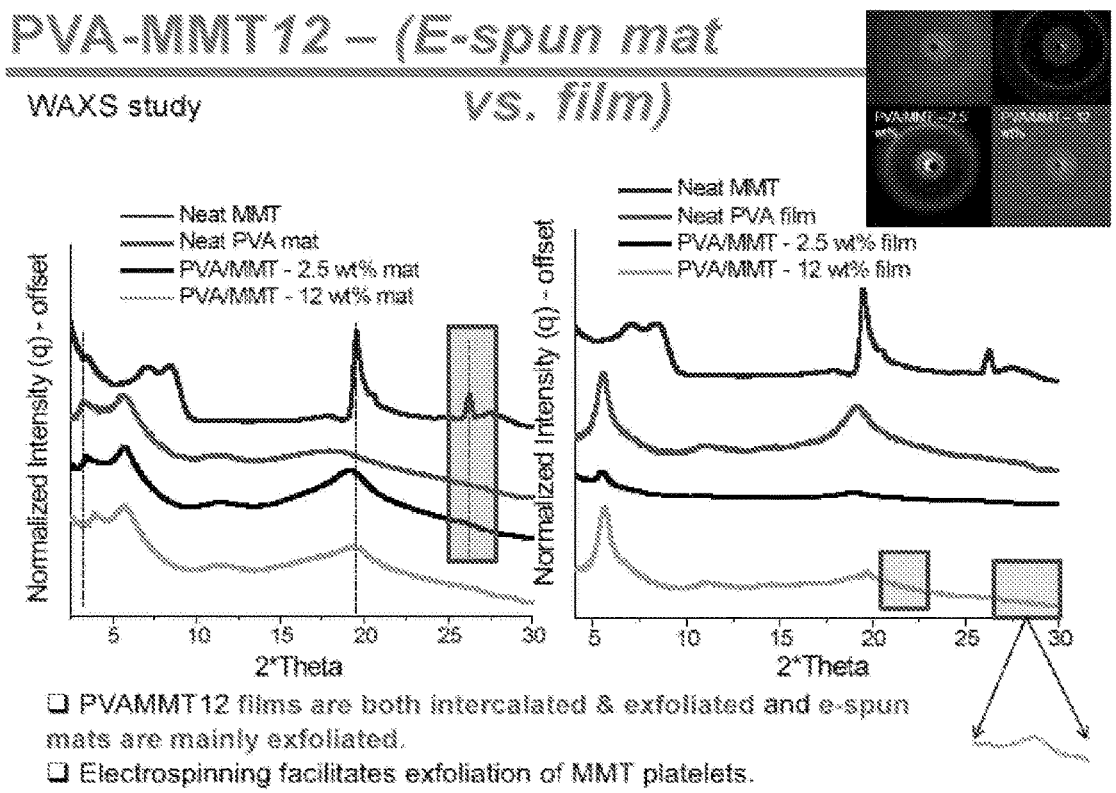
Figure 58:
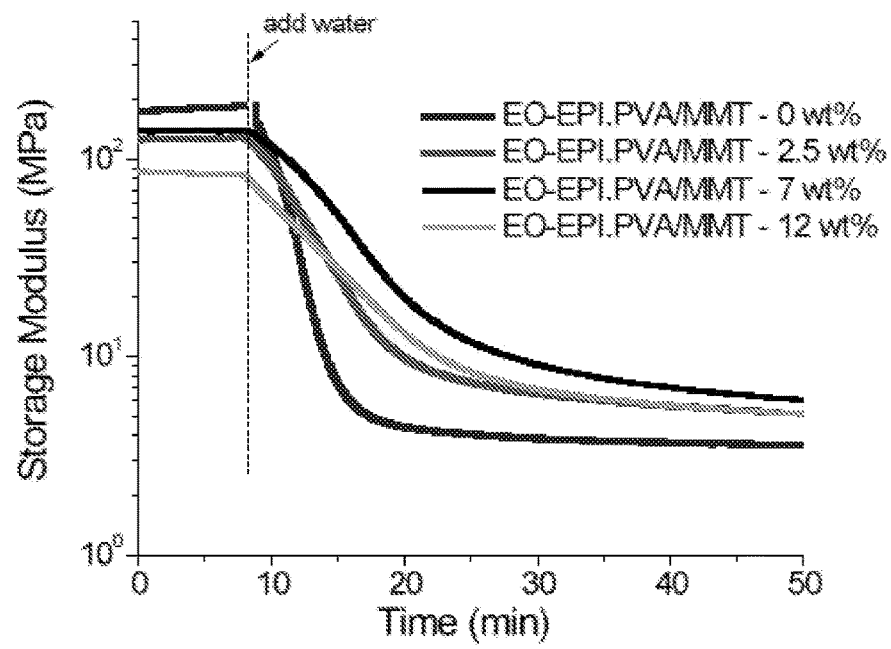
FIG. 58 portrays graphic data concerning storage modulus of exemplary materials/conditions.

FIG. 54 depicts exemplary mechanical behavior of PVA/MMT composites. FIG. 55 depicts exemplary tan δ analysis of PVA/MMT composites. FIGS. 56 and 57 compare PVA/MMT electrospun mats to films. FIG. 58 depicts softening due to water of a composite of EO-EPI, PVA and MMT.

Figure 59:
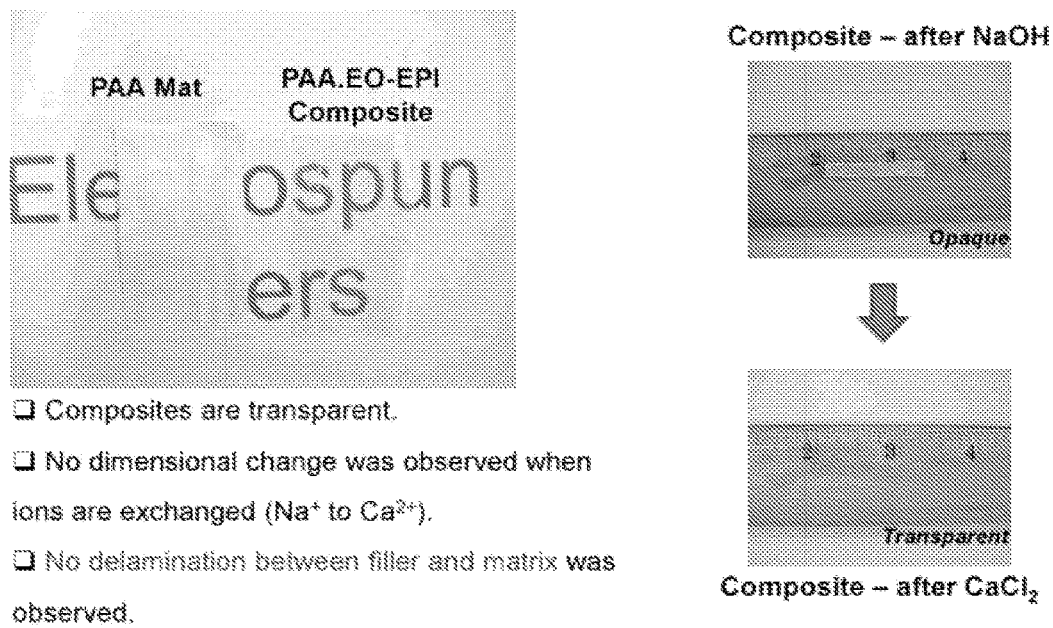
FIG. 59 depicts photograph images of exemplary materials.
Figure 60:
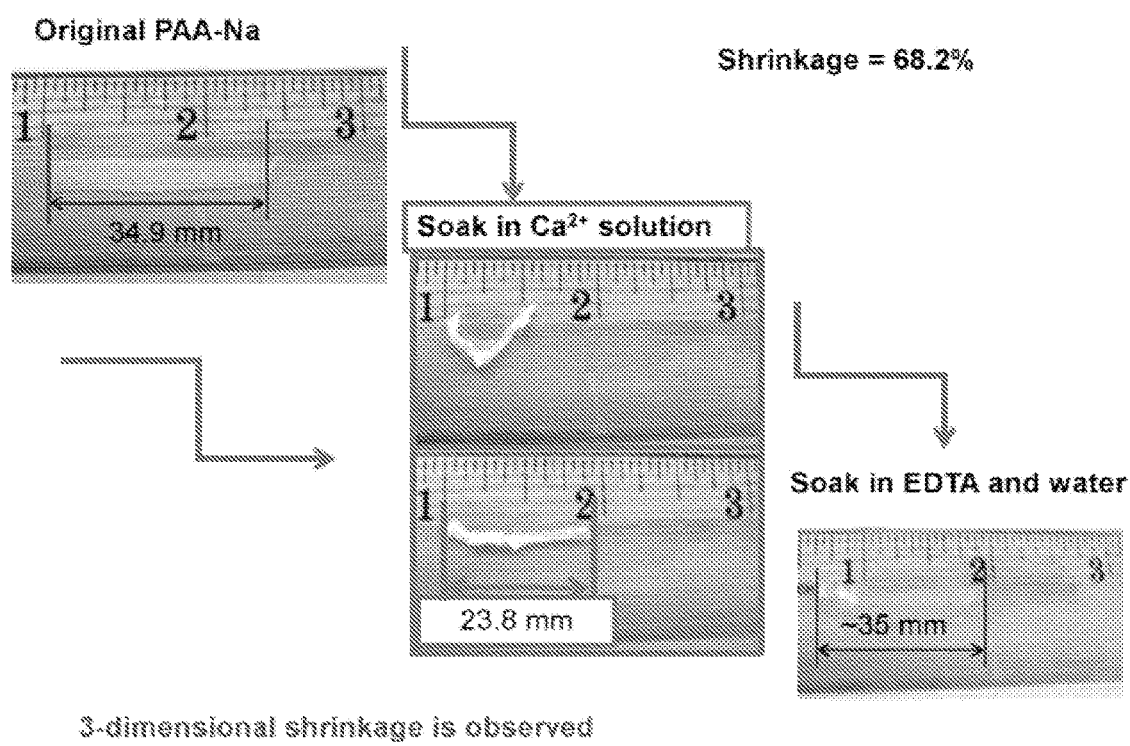
FIG. 60 depicts shrinkage of the ion-responsive mat.
Figure 61:
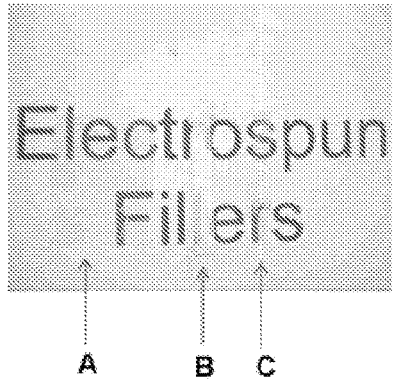
FIG. 61 further depicts transparency of composites.
Figure 61:
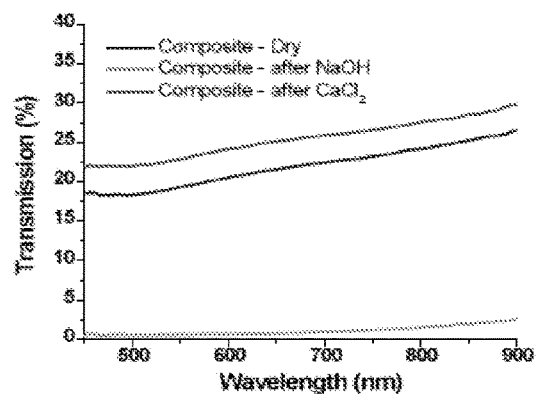
Figure 62:
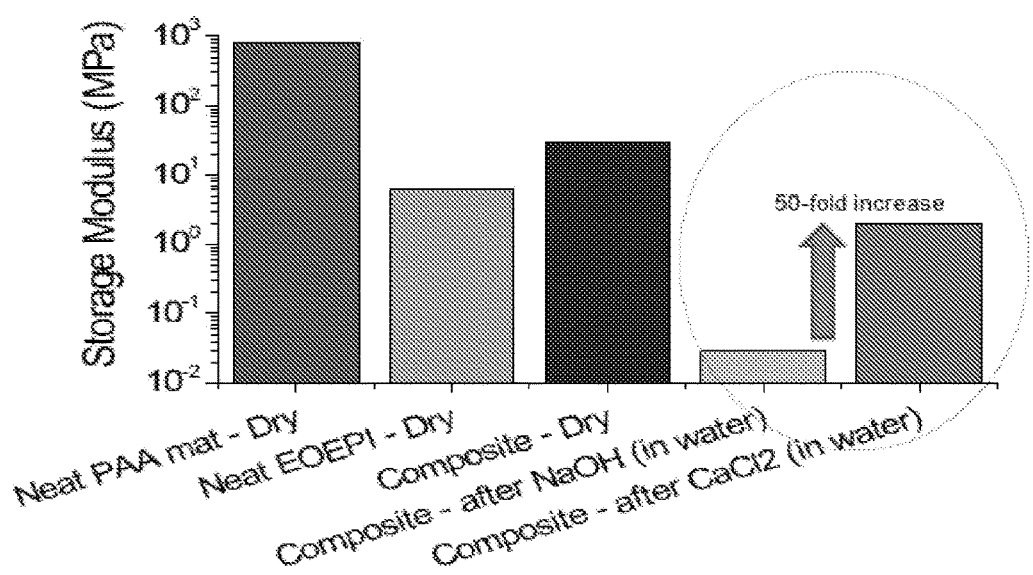
FIG. 62 portrays graphic data concerning storage modulus of exemplary materials/conditions.
Figure 63:
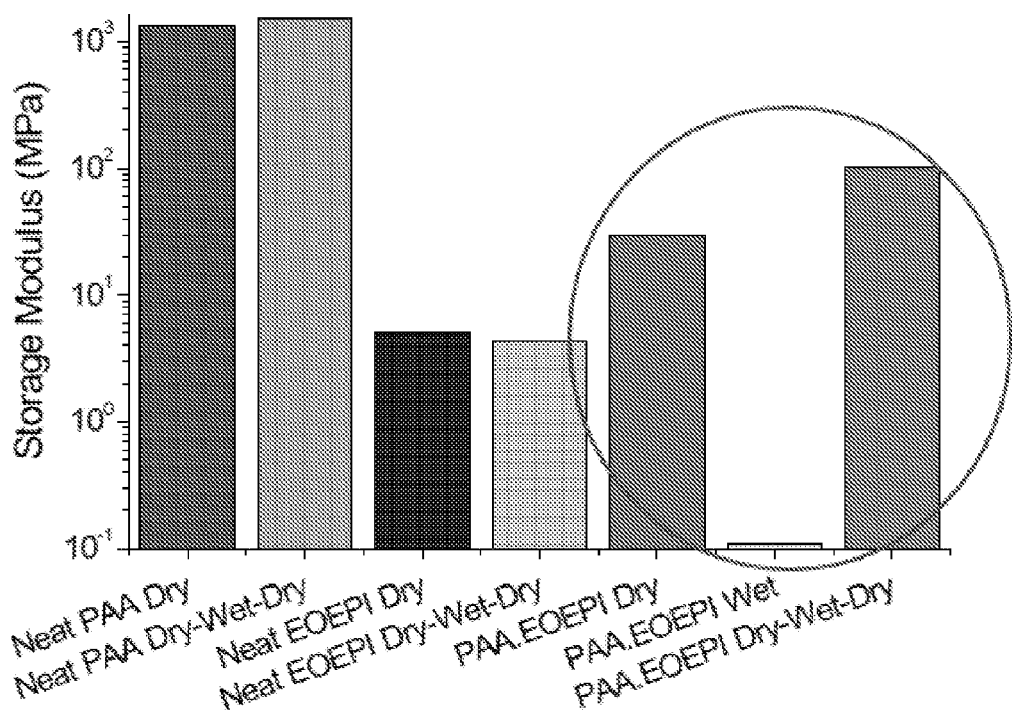
FIG. 63 portrays graphic data concerning storage modulus of exemplary materials/conditions.
Figure 64:
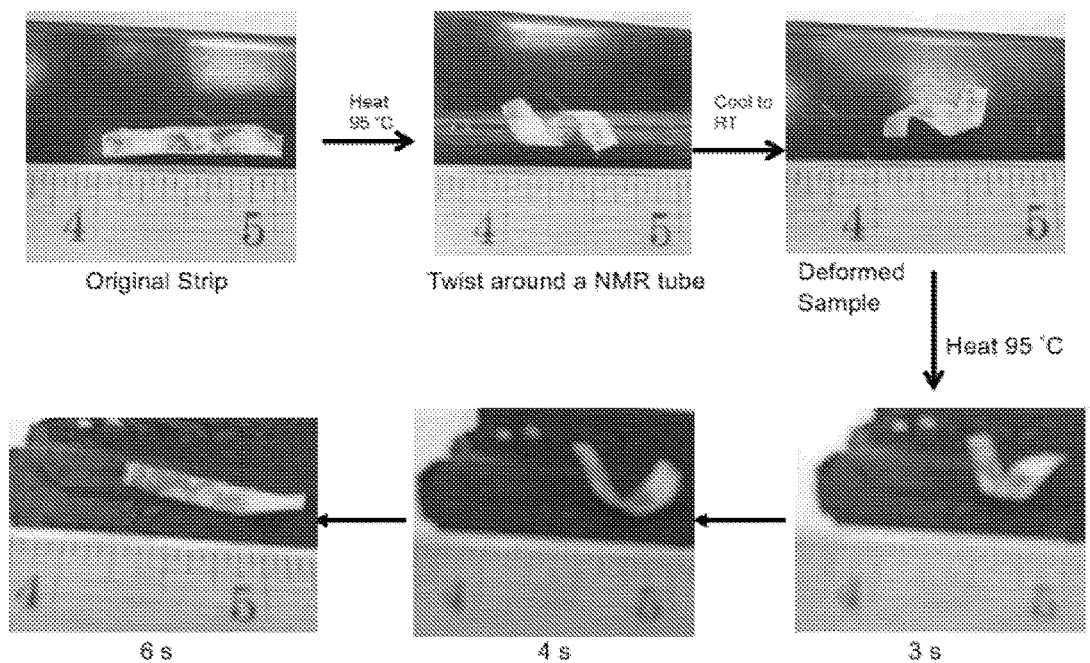
FIG. 64 depicts photograph images of exemplary materials.
Figure 65:
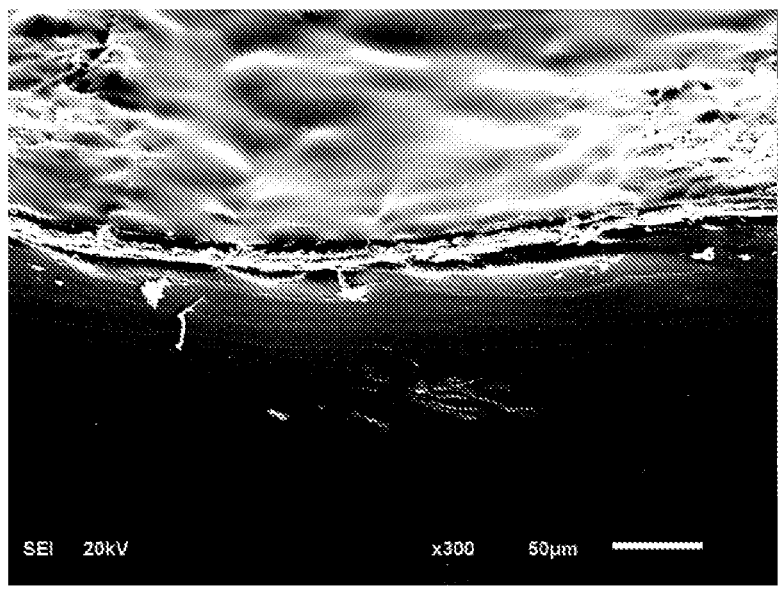
FIG. 65 depicts a scanning electron microscope image of an exemplary material.
Figure 66:
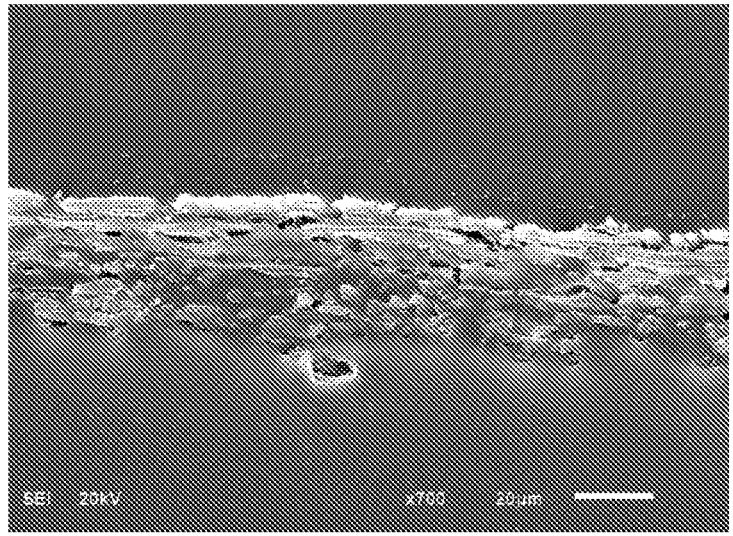
FIG. 66 depicts a scanning electron microscope image of an exemplary material.
Figure 67:
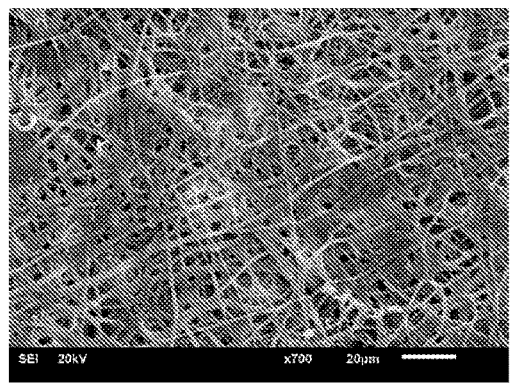
FIG. 67 depicts scanning electron microscope images of an exemplary materials.
Figure 67:
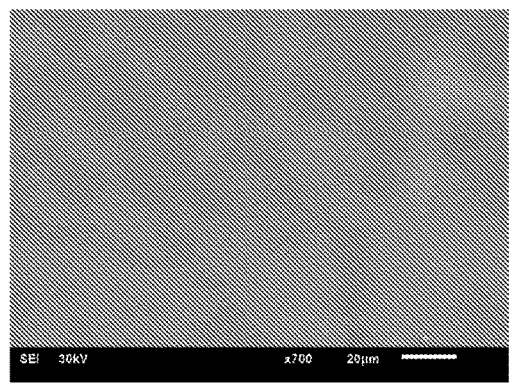
Figure 67:
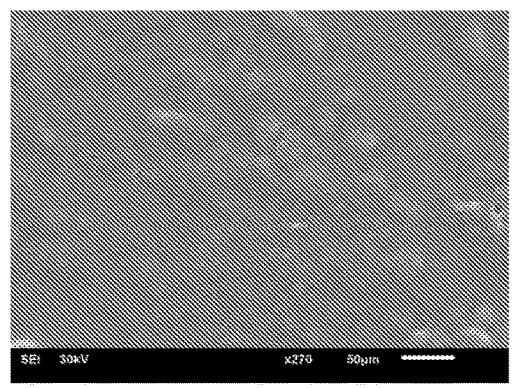
Figure 67:
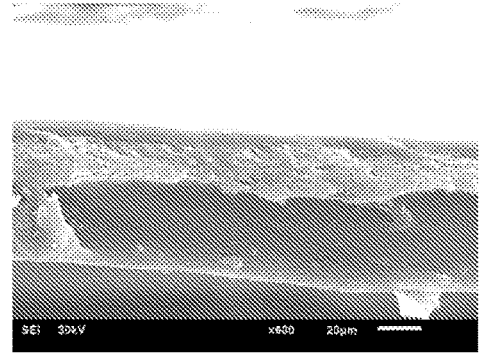
Figure 67:
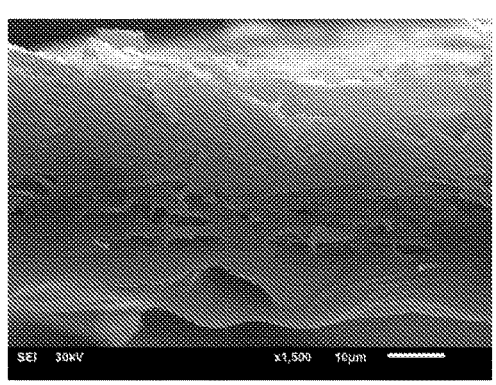

In another example, poly(acrylic acid) (PAA) can be used as a filler for an EO-EPI matrix. FIG. 59 depicts the transparency of the PA/EO-EPI composite as compared to a PAA mat. As will be understood, such a composition is ion-responsive. FIG. 60 depicts shrinkage of the ion-responsive mat. FIG. 61 further depicts transparency of composites. FIG. 62 depicts the switchability of composites via ion exchange. FIG. 63 depicts the two-way switchability of composites. FIG. 64 depicts shape memory of composite materials. FIGS. 65 and 66 are scanning electron microscope images of exemplary materials and describe additional methods of forming composites. FIG. 67 is scanning electron microscope images of exemplary materials.

Nature employs several materials and structures for inspiring the designing and fabrication of high-performance materials with enhanced properties. When mechanical properties of a single-phase system are insufficient for an application, composite materials can offer an important strategy to impart increased strength and toughness. By introducing nanoscale filler components, greater enhancement in mechanical function compared to traditional macro- and microscale fillers is possible due to the greater surface area and lower percolation thresholds stemming from the higher aspect ratios of the nanoscale fillers. In this Perspective, we will discuss polymer nanocomposites drawing from the lessons of wood (network of preformed, high-modulus cellulose nanorods), spider silk (self-assembly of ordered domains), and tendon (hierarchical ordering).

Bioinspiration can be thought of as a biological concepts, mechanisms, functions, and design features are abstracted as a starting point on the road to new synthetic materials and devices with advanced structures and functions. Creative use of design motifs found in nature can be employed to fabricate novel materials. Nature employs several strategies in fabricating high-performance materials from which can be gleaned important lessons. For example, the strength and elasticity of wood, whose cell walls are comprised of cellulose fibers embedded in a matrix of lignin, can be largely governed by the ordering of the cellulose fibers in the protein matrix. Spider silk also has a blend of high strength and flexibility. Silk's mechanical properties come from crystalline domains tethered together by amorphous regions. Tendon is comprised of ordered collagen bundles tied together by a matrix of proteoglycans. Because of the hierarchical ordering of the tendon, the overall strain of the tendon is always larger than the strain exhibited in the individual fibrils.

Using the previous examples, several important lessons are evident from the design and function of the natural composite materials. While each of the previously mentioned natural systems involves many factors to obtain their unique properties, an illustrative property of each system will be discussed as inspiration for man-made composite materials. For example, wood demonstrates the importance having a well-dispersed network of high-strength rods in a softer matrix to impart increased strength. Furthermore, by using components with complementary strengths (a matrix with high compressive strength and a filler with high tensile strength, for example), a synergistic net effect can be attained. For spider silk, the role of self-assembly in processing and material function is shown. Spiders store the silk-forming proteins in a β-sheet-deficient conformation, allowing the proteins to maintain solubility and facilitate the spinning process. During spinning, a morphological transition from a β-sheet-deficient to β-sheet-rich material occurs, providing the unique combination of strength, flexibility, and toughness observed in spider silk. Finally, hierarchical ordering within a composite, such as a tendon, can contribute to interesting mechanical properties. With ordering across multiple scales, stress relief events due to the reorganization of individual components can be an avenue toward increased toughness. While polymeric materials give rise to a wide array of bulk properties depending upon their molecular composition and architecture, these material properties can be insufficient for some demanding technologies, such as high-strength and low weight materials needed for the wings on airplanes. Various high performance polymers have been developed by incorporating rigid or associative segments into the polymer backbone, but a balance between strength and processability must be found for practical applications. In order to access material properties otherwise unobtainable via pure polymers while maintaining processability, additives and fillers are often introduced to a polymer matrix to generate a composite material. A composite is generally defined as a material comprised of two or more constituents that have significantly different mechanical properties and that remain separate and distinct within the final structure.

To be considered a nanocomposite, the size of the filler component must be on the nanoscale. Early additives to be exploited in polymer composites, such as glass fibers (diameter ~10-30 μm), were generally microscopic in scale. While enhanced mechanical properties were achieved with these materials, the enhancement per weight of filler was limited because of the low surface area to volume ratio. Recent focus has shifted to the use of nanoscale fillers in lieu of the traditional microscopic fillers in order to expand the potential range of composite materials even further. Nanoscale fillers typically have much higher aspect ratios that lead to greater surface area per mass and lower percolation thresholds which enable mechanical enhancement at lower filler contents than with traditional fillers. Because less filler material is needed, lighter and more cost-effective materials have been produced and used by the automotive, aerospace, and construction industries.

Figure 68:
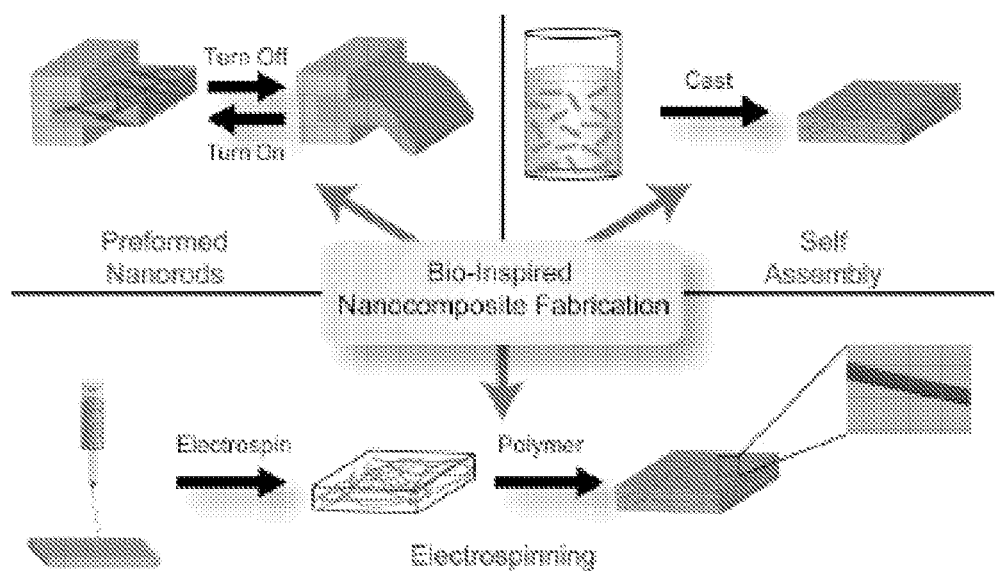
FIG. 68 is a schematic representation of exemplary fabrication methods

Polymeric composite materials are typically classified as either hybrid, both organic and inorganic components, or wholly organic. Polymer nanocomposites can draw from the lessons of wood (network of preformed, high-modulus cellulose nanorods), spider silk (self-assembly of ordered domains), and tendon (hierarchical ordering). Specifically, (i) preformed rods from renewable resources as filler materials, (ii) self-assembled small molecules, and (iii) fibers generated by electrospinning FIG. 68 is a schematic representation of fabrication methods for bioinspired polymer nanocomposites.

Wood comprises networks of preformed cellulose nanorods. The fibers, which have high strength due to their crystalline structure, can be isolated from a wide variety of sources, including wood, cotton, algae, bacteria, and sea tunicates. These cellulose fibers typically have aspect ratios varying between 10 and 100 and diameters ranging from 4 to 20 nm, depending on the cellulose source. The high elastic moduli (100-150 GPa) of cellulose fibers makes them an excellent reinforcing component in polymer nanocomposites. Examples are discussed below.

One area where cellulose nanofiber composite materials are of interest is in optically transparent applications. When the individual components of a composite material are one-tenth the wavelength of light, these composites are typically free of scattering. It is found that at 60-70 wt % loading of cellulose fibers in epoxy resin up to 80% transmission of the incident light was achieved. The transmission loss attributed to the nanofiber network is found to be less than 10% even though refractive indices of the two components are mismatched. Coupled with high transparency, the nanocomposite films are found to exhibit significantly higher mechanical strength and lower thermal expansion coefficients. The Young's modulus of the composite film was 20-21 MPa, while the tensile strength reached values near 325 MPa.

As another example, epoxy resins reinforced with cellulose nanofibers isolated from sea tunicates and cotton. While nanofibers isolated from sea tunicates have a higher aspect ratio than cotton-derived fibers, cotton is a more readily available source material. A simplified composite fabrication technique can use solvent exchange instead of lyophilization and redispersion of the cellulose nanofibers that is commonly employed to fabricate cellulose nanocomposite films. This strategy is important because lyophilization is typically a limiting step in terms of time, energy, and cost for the film production process. Using this simplified approach, films with a well-dispersed percolating network of nanofibers can be fabricated. While the inclusion of cellulose nanofibers is found to moderately improve the mechanical properties below the glass transition temperature ($T_g$) of the epoxymatrix, once above the $T_g$ of the matrix, the tensile storage modulus was found to significantly increase from about 16 MPa for the matrix polymer to about 1.6 GPa for sea tunicate composites and about 215 MPa for cotton composites.

Understanding of the interactions between the filler and the matrix that give rise to enhanced properties can assist in designing materials. Raman spectroscopy has emerged as a powerful tool for evaluating the stress transfer from polymer matrix to the cellulose nanofibers. Such a technique can be used to study stress transfer efficiency between composite films of poly-(L-lactic acid) (PLLA) and bacteria-derived cellulose nanofibers cultured for either 3 (BC3) or 6 days (BC6), which primarily impacts the total surface area of the filler. The composites fabricated from bacterial cellulose cultured for 3 days were found to have about 15 times the surface area of the nanocomposites fabricated from bacterial cellulose cultured for 6 days as measured by nitrogen adsorption. Young's modulus and stress-at-failure were found to increase for both PLLA nanocomposites compared to neat PLLA. While the overall increase in the modulus and failure stress was higher for the BC6 nanocomposites compared to the BC3 nanocomposites, the specific Young's modulus (divided by density) was similar. The BC3 nanocomposite was found to have an increased interaction with PLLA matrix, which was attributed to the significantly increased surface area compared to the BC6 nanocomposite.

Another approach is the fabrication of stimuli-responsive or "smart" materials. One example of an all organic, stimuli-responsive polymer nanocomposite that closely mimics the adaptability and structure of the sea cucumber dermis. Nanocomposite materials made from a rubbery matrix and cellulose nanofibers isolated from tunicates can be fabricated by solution casting followed by compression molding. When exposed to a chemical stimulus, for example water, the interactions between the rigid cellulose nanofibers of the filler can be minimized. Upon the weakening of the support matrix, the tensile modulus is found to reversibly decrease by a factor of 40 when ethylene oxide-epichlorohydrin 1:1 copolymer (EO-EPI) is used as the matrix. The modulus differential can be even greater, up to several orders of magnitude, when filler softening is coupled with a thermal transition ($T_g$) of the polymer matrix with a poly-(vinyl acetate) (PVAc) matrix. Similar results have been achieved using cotton, a much more readily available and industrially relevant material, as the source of cellulose nanofibers.

The nanocomposites can be conditioned by either drying in vacuum, equilibrium swelling in deionized water, or swelling to saturation in deionized water followed by redrying in vacuum.

Using a construction inspired by natural wood, stiff filler rods in a soft matrix, stronger polymeric materials can be produced. Cellulose nanofibers have been shown to be a versatile and robust natural filler material for use in a multitude of applications. Mechanically dynamic materials using cellulose nanofibers have been realized by understanding and controlling the filler-filler and filler-matrix interactions. The possibility of multifunctional or multi-stimuli responsive nanocomposite materials exists with the introduction of additional switching segments to control and tailor filler interactions.

Spider silk is generally self-assembling of ordered domains. Using organization strategies inspired by nature, it is possible to controllably create assemblies of molecules into an array of ordered and functional architectures. Using nature-inspired self-assembly of small molecules into nanostructures as a nanocomposite fabrication strategy, nanocomposite materials with structures reminiscent of spider silk that display improved mechanical properties have been developed.

One example of a self-assembling small molecule fillers in polymer nanocomposite materials is dibenzylidene sorbitol (DBS). DBS is a butterfly-shaped amphiphile capable of inducing gel formation in various organic liquids and polymer melts by forming a three dimensional network of nanofibers. Thermal and mechanical properties of a DBS derivative, 1,3:2,4-di-p-methylenebenzylidene (MDBS), in the matrix of a polypropylene copolymer with 3 wt % ethylene can be formed. The MDBS nanofibers served as nucleation sites, which induced heterogeneous nucleation of polymer spherulites. At lower concentrations, MDBS served as a clarifying agent, resulting in films with increased transparency and yield strength. At higher concentrations of MDBS, the diameter of the nanorods increased, reducing optical clarity but further improving the ultimate mechanical properties. These results can be an indication that at higher concentrations MDBS acts as a reinforcing agent, but at lower concentrations it behaves as a clarifying or nucleating agent.

Figure 69:
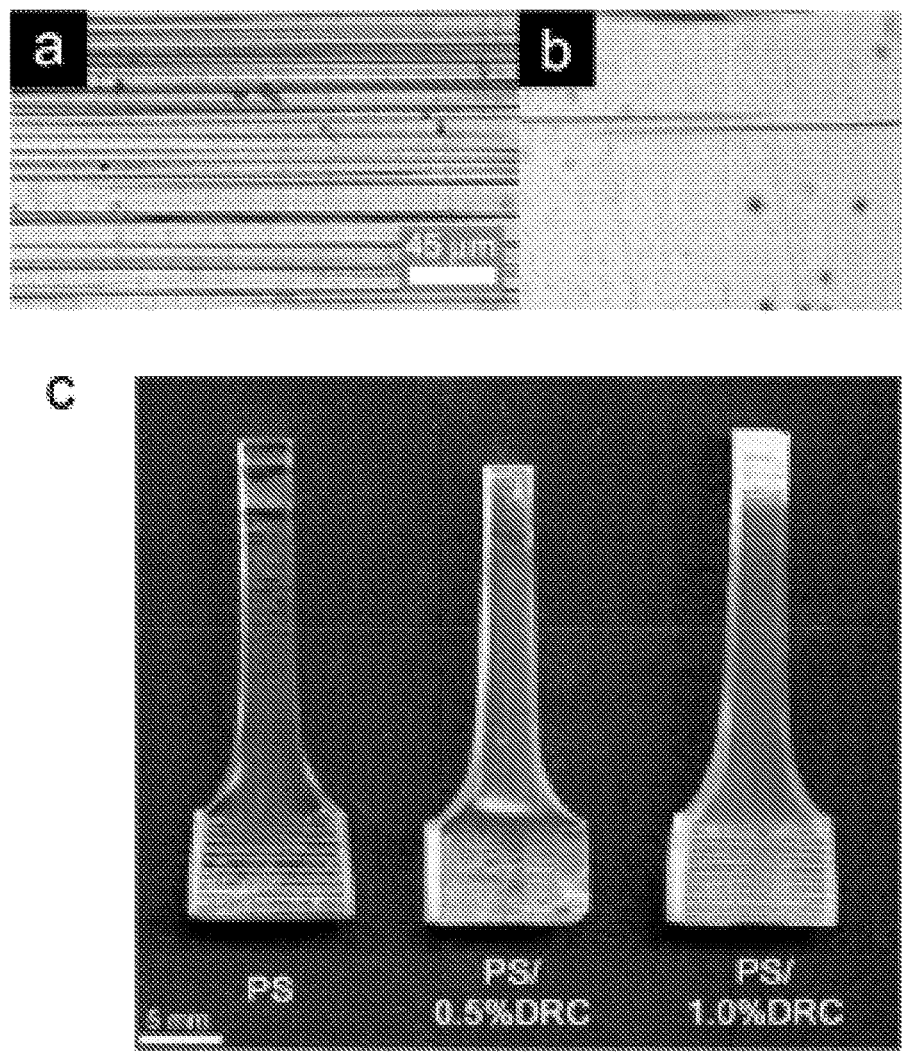
FIG. 69 depicts a scanning electron microscope images of an exemplary materials.

In one example, a class of molecules known as dendron rod-coils (DRC) self-assemble into nanoribbons approximately 10 nm wide, 2 nm thick, and micrometers long. In styrene monomer, the DRCs were found to induce gel formation at concentrations as low at 0.1 wt %. Upon thermal polymerization of the preformed gel, birefringence was found to increase with a maximum at 0.5 wt % of DRC. The observed increase in birefringence was attributed to increased alignment of the polymer chains induced by the DRC nanofibers. It is also noted that the Charpy impact strength of the polystyrene/DRC nanocomposite with 0.5 wt % DRC was nearly double that of pure polystyrene. It was also revealed that the improved toughness and ductility of the nanocomposites were due to increased stress whitening and craze density in the DRC modified films (as shown in FIG. 69). The smaller and higher-density crazes in DRC composites resembled those formed in more highly oriented polymers when stressed in tension along their axis of orientation. The filler-induced change of local polymer chain orientation in these DRC-based nanocomposites modified the crazing patterns, enhancing mechanical behavior.

Bitumen can be reinforced via small molecule incorporation. Using aliphatic diacids as the self-assembling nanofiller, a percolated network of micrometer long nanofibers formed upon cooling in bitumen at concentrations as low as 3 wt %. The softening temperature of bitumen can be studied to investigate the reinforcement of the matrix, revealing that, with as low as 3 wt % of diacid incorporated into the composite, the softening temperature increased by as much as 60 degrees Celsius (as shown in FIG. 69), suggesting mechanical reinforcement of the bitumen matrix. It can be determined that, below room temperature, the elastic modulus is an order of magnitude higher for the nanocomposite material than pure bitumen. Although the room temperature mechanical properties are enhanced with the inclusion of self-assembling diacids, the melt viscosity at typical processing temperatures remained unchanged.

Figure 70:
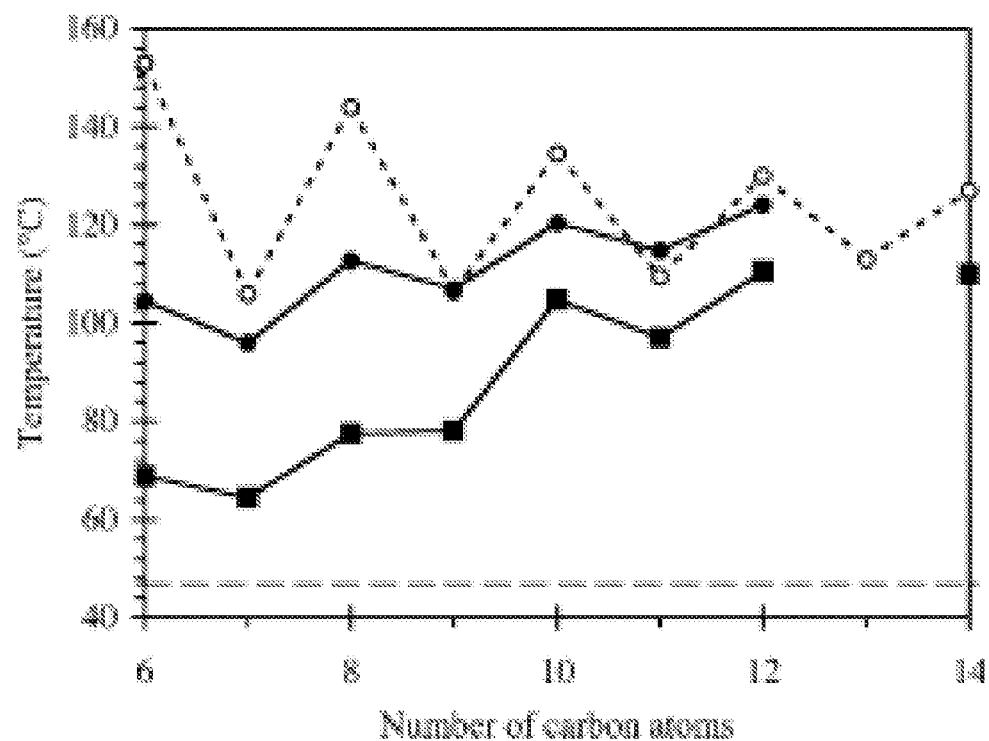
FIG. 70 portrays graphic data concerning temperature of exemplary materials/conditions.
Figure 71:
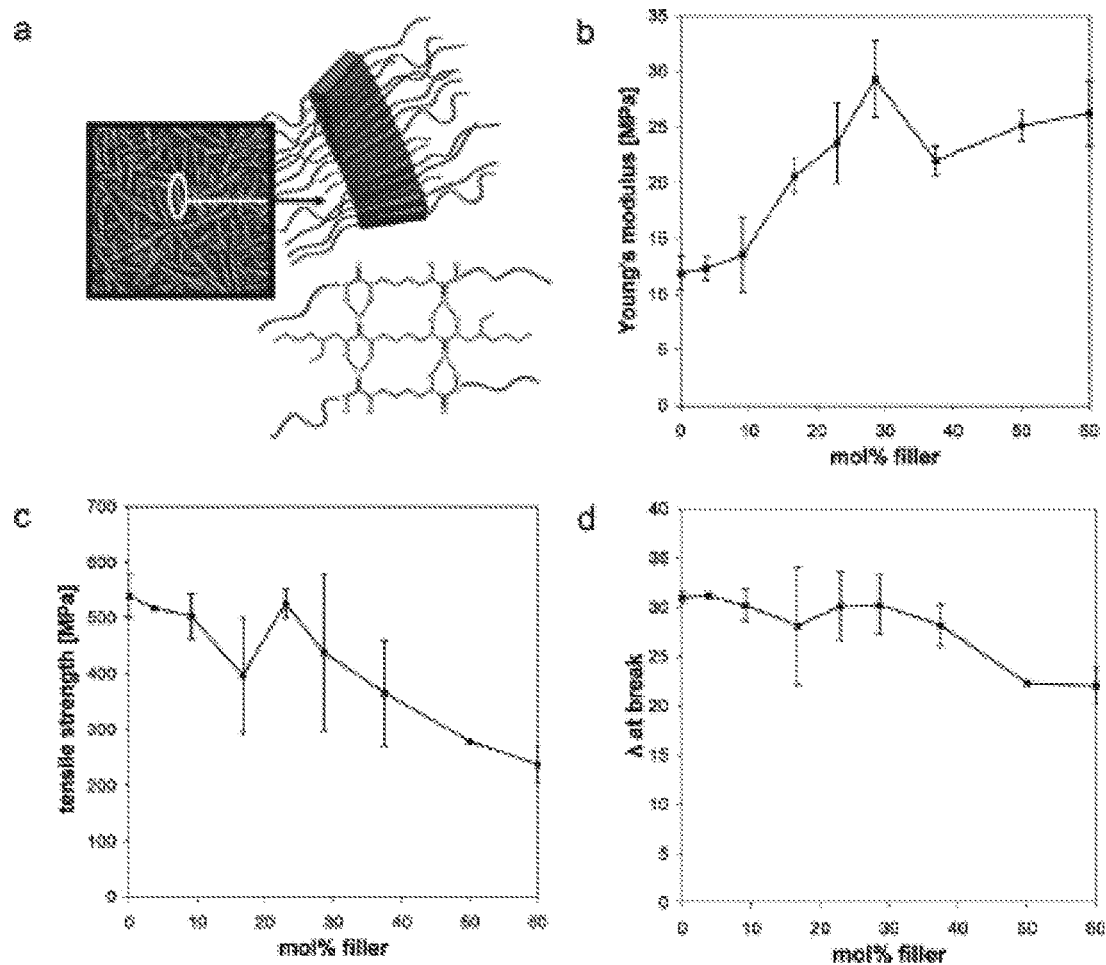
FIG. 71 depicts exemplary materials.

FIG. 69 illustrates transmission opticalmicroscopy images of craze microstructure of 250% prestrained specimens just below the fracture surfaces of (a) PS/0.5 wt % DRC and (b) PS homopolymer. (c) photographs of 250% prestrained tensile specimens after testing failure in uniaxial tension. FIG. 70 illustrates softening temperature of bitumen with 3% (w/w) diacid (shown as solid squares) vs. the number of carbon atoms of the diacids. These values can be compared to the softening temperature of pure bitumen (dashed line), the melting temperature (open circles), and the sublimation temperature (at a pressure of 0.5 Pa) (solid circles) of pure diacids The interaction between the matrix and filler can be crucial for optimal performance in polymer nanocomposite materials. As an example, when segmented polyurethanes are mixed with smectic clay particles, enhancement of the thermo-mechanical properties occurs when the clay particles are confined within the hard segment of the polymer. When the clay particles are located in the soft segment, substantial reduction in toughness and extensibility occurs. While most composite materials rely on simple mixing to achieve matrix-filler interaction, using molecular recognition, similar to the "lock-and-key" mechanisms pervasive throughout biological systems, is an underused strategy to impart mechanical enhancement of polymeric systems. A molecular filler designed to be a perfect fit with the corresponding elastomeric polymer is shown schematically in FIG. 71. FIG. 71 illustrates (a) modular approach: the supramolecular filler (red) is incorporated into the polymer hard domains (blue) via bifurcated hydrogen bonds. Young's modulus (b), tensile strength (c), and k at break (d) of films containing increasing amounts of filler. Data derived from true σ-λ curves.

Mixing up to 7.3 wt % (23 mol %) increased the Young's modulus by over 100% while not influencing the yield strength, tensile strength, and strain at break (see FIGS. 71b-71d). At concentrations below 23 mol %, the fillers preferentially associated with the hard segment due to matching hydrogen bonding motifs and molecular size. Above 23 mol %, the filler began to phase separate, forming a secondary hard phase in the composite material. Furthermore, studies have revealed that filler materials with no matching or without hydrogen-bonding groups tend to not interact with the polymer hard segments, further underscoring the importance of molecular compatibility needed for optimal properties.

Using self-assembling small molecules offers an important processing advantage over preformed particles or rods by not altering the melt rheology and mimics nature's strategy for spinning spider silk. As previously mentioned, spider silk is stored in a random conformation, allowing the protein to maintain solubility. Once spun, a conformational transformation occurs, yielding the crystalline domains needed for its mechanical integrity. Since the self-assembly of small molecules is often reversible by external stimuli, usually via temperature, only minimal impact on the melt viscosity would be expected upon dissolution of the small molecule additive at low concentrations. After processing and upon cooling, the small molecules can then assemble into a nanofibrillar arrangement, creating the reinforcing filler component. Furthermore, by controlling the crystallinity and size parameters of the self-assembled nanofibers, the mechanical properties of the composites should be able to be controlled.

Tendons are hierarchical ordering. Electrospinning processes are able to create nanofibers from a wide array of polymers for applications ranging from cell scaffolds to filtration membranes and electronic devices to drug delivery vehicles. As previously described, in electrospinning, fibers are generated by applying an electric field between a polymer solution and a grounded collector. When the electrostatic force overcomes the surface tension of the polymer solution, a stable jet or "Taylor cone" can be formed. As the jet travels toward the collector, it is constantly subjected to a stretching movement producing nanofibers of tunable diameter. Nanofibers fabricated via electrospinning have also been used as the filler component in polymer nanocomposite materials. These electrospun nanofibers can be oriented into ordered arrays, providing a pathway to fabricate hierarchically organized composites with an arrangement inspired by the fiber packing observed in tendon.

Nanocomposite films can be uniform. For example, electrospun nylon-4,6 (30-200 nm diameter) in an epoxide matrix. At only about 4 wt % loading of nanofibers, the Young's modulus and fracture stress were found to significantly increase, while the fracture strain significantly decreased. Epoxide and rubber matrices can be reinforced with fibrous mats of poly(benzimidazole) (PBI). When incorporated into epoxy resins, the Young's modulus, fracture toughness, and the fracture energy were found to increase with increasing content of PBI fibers. Furthermore, when compared against composite films containing a commercial PBI fiber filler, a more significant enhancement in mechanical properties was reported via incorporation of the electrospun PBI fibers due to the increased surface area of the electrospun fibers. In a rubber matrix, the Young's modulus of the PBI nanofiber-reinforced composite was 10 times higher than the neat rubber and significantly higher than carbon black reinforced rubber composite materials.

Figure 72:
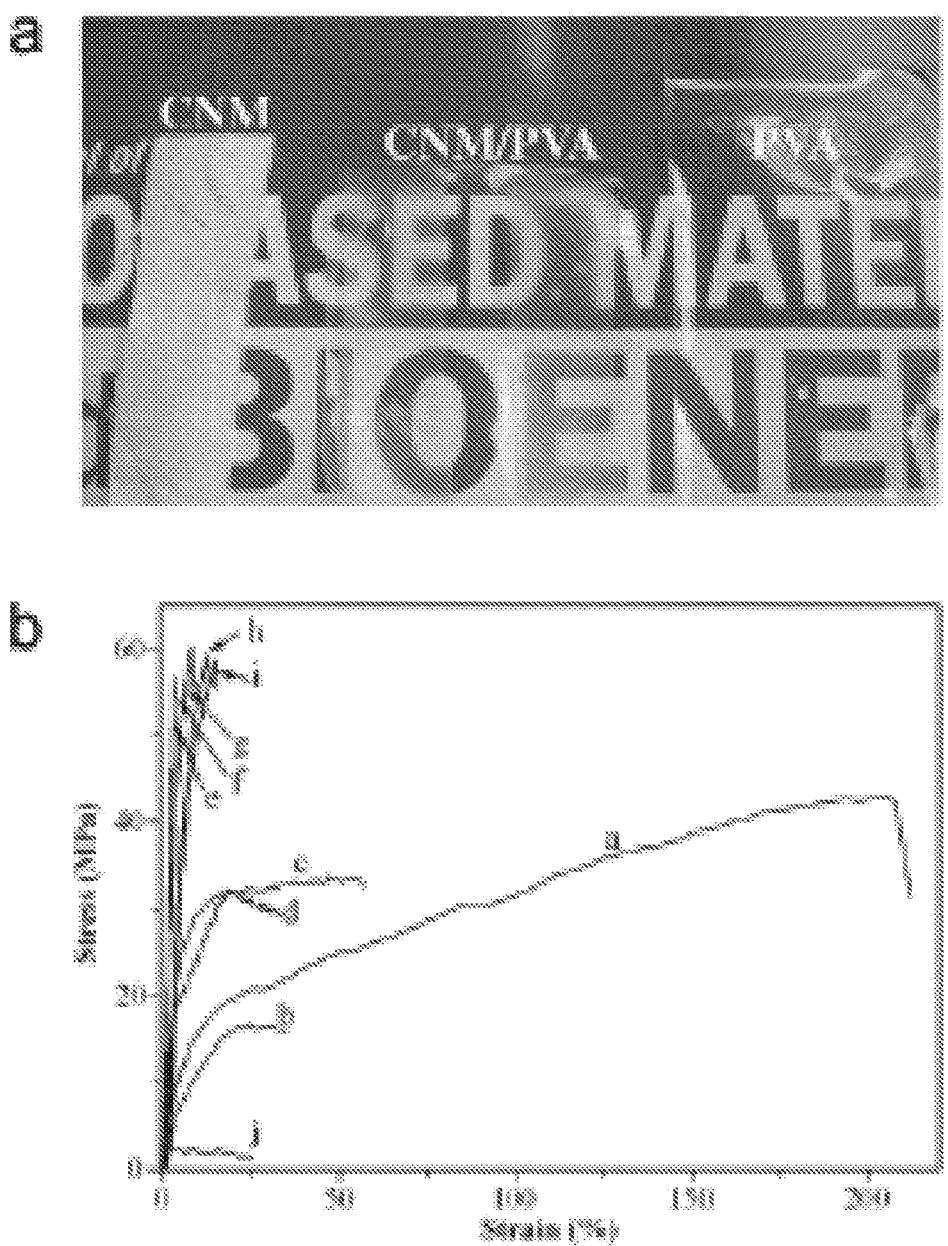
FIG. 72 depicts exemplary materials.

Poly(vinyl alcohol) (PVA) films can be reinforced with a cellulose nanofiber mat electrospun from an acetone/N,N-dimethylacetamide solution with fibers ranging between 100 and 900 nm. Complete hydrolysis of the cellulose mat was achieved via treatment with a base, which facilitated impregnation with hydrophilic PVA to produce highly transparent films. The cellulose acetate fibers are relatively hydrophobic, but upon hydrolysis, the hydrophilic alcohol groups were able to hydrogen bond with the PVA, creating a uniform composite film. These PVA/electrospun cellulose nanofiber films with loadings up to 40 wt % transmitted 75% of incident light. At high cellulose nanofiber content, the PVA composite exhibited an increase in mechanical strength by 50% and Young's modulus by more than 600%. FIG. 72 depicts the (a) appearance of films—cellulose nanofibrous mat (CNM)/PVA composite film contains 40 wt % CNM; and (b) stress-strain curves of CNM/PVA composite films—mass content of CN Min the composite films is (a) 0, (b) 4.7, (c) 5.5, (d) 8.4, (e) 23, (f) 24, (g) 40, (h) 50, (i) 60, and (j) 100.

Another area in which polymeric nanocomposite containing electrospun fillers have found application is in shape memory elastomeric materials. Shape memory can be created for elastomeric composites from electrospun mats of poly-(ε-caprolactone) (PCL) and a silicone rubber (Sylgard 184). Thermal characterization revealed that the composite film has three distinct transitions attributed to the glass transition of Sylgard 184 ($T_g$=−114.4 degrees Celsius), the glass transition of PCL ($T_g$=−49.5 degrees Celsius), and the melting transition of PCL ($T_g$=60.6 degrees Celsius). Shape memory was imparted to the elastomeric nanocomposite through the melting of the semi-crystalline PCL fibers. The Sylgard composite showed a sharp recovery centered at 60 degrees Celsius, corresponding to the melting temperature of the PCL fibers and exhibited almost complete shape fixing and recovery.

Figure 73:
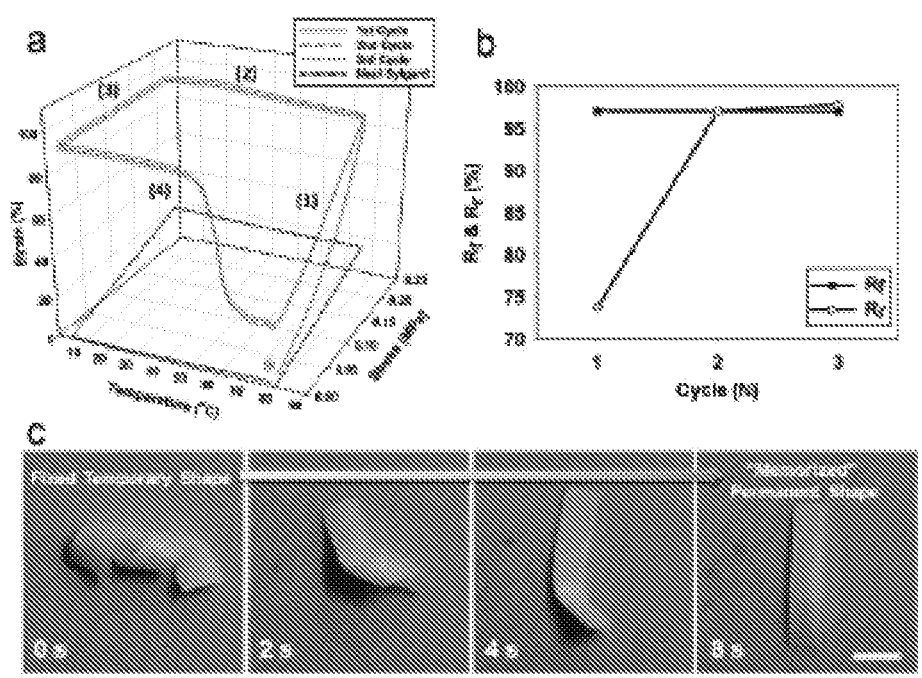
FIG. 73 depicts exemplary materials.

FIG. 73, illustrated shape memory properties of Sylgard/PCL SMECs, (a) stress-temperature-strain plot showing the one-way shape memory (1WSM) cycles of Sylgard/PCL, compared with neat Sylgard (the asterisk indicates the onset point), (b) fixing ratio ($R_f$) and recovery ratio ($R_r$) calculated for three cycles, (c) photographs of Sylgard/PCL composite showing the recovery from a fixed temporary shape to its "memorized" permanent shape on a temperature-controlled plate at 80 degrees Celsius (the scale bar represents 5 mm).

By controlling the hierarchical ordering within electrospun composites, tunable and responsive mechanical properties are achievable. For example, exploitation of the crystalline structure within the electrospun fibers makes possible shape memory behavior. Electrospinning is a facile and readily adaptable processing technique, which affords a unique strategy for the development of ordered, nanofiber arrays. By using well-aligned nanofibers, mechanically anisotropic materials are also feasible. Using core-shell nanofibers produced by coaxial electrospinning, the potential to fabricate composites with a hierarchical structure reminiscent of the organization in tendon exists.

Stimuli-responsive materials are suitable for a wide range of applications. The design and fabrication of all-organic, stimuli responsive polymer composites using electrospun nanofibers as the filler are disclosed herein. Incorporation of 4 wt % of filler into the polymer matrix increased the tensile storage modulus two orders of magnitude. Upon exposure to water, the filler fibers plasticize and no longer provide mechanical reinforcement. The tensile storage modulus subsequently diminishes two orders of magnitude to the value of the neat matrix polymer. A range of polymer matrices have also been explored, which allows two-way switchable mechanical behavior. Sustained drug release has been achieved through control of matrix-filler interactions and tailoring of the burst release profile of hydrophilic model drug compounds. Additional, the optical properties of these composites can be tuned via refractive index matching to achieve transparent, responsive composites.

Structural materials exhibiting multi-functionality are suitable for regenerative medicine and drug delivery. Examples of functionality include delivery of therapeutic compounds and optical transparency. Electrospinning can be used to fabricate structural materials. Two important approaches for improving optical transparency in electrospun fibers are highly-oriented fibers and infiltration of isotropic mats with polymer matrices.

Highly aligned fibers of polystyrene, PMMA, poly (HEMA) and PLGA, can be obtained by controlled electrospinning parameters including, but not limited to, voltage and needle-to-drum distance. Electrical forces can be arranged such that they do not dominate viscous forces. In another example, void spaces are filled with a material having a greater refractive index than air and relatively close to that of random electrospun fibers. Toward that end, electrospun poly(vinyl alcohol) (PVA) fibers can be impregnated with rubbery 1:1 ethyleneoxide/epichlorohydrin copolymer (EO-EPI) as the matrix.

The foregoing description of examples has been presented for purposes of illustration and description. It is not intended to be exhaustive or limiting to the forms described. Numerous modifications are possible in light of the above teachings. Some of those modifications have been discussed, and others will be understood by those skilled in the art. The examples were chosen and described in order to best illustrate principles of various examples as are suited to particular uses contemplated. The scope is, of course, not limited to the examples set forth herein, but can be employed in any number of applications and equivalent devices by those of ordinary skill in the art.

What is claimed is:

1. A polymer composite comprising:
   a filler comprising an electrospun polymer mat of a first material;
   a matrix comprising a polymer film of a second material;
   wherein the electrospun polymer mat is soaked in methanol and then the electrospun polymer mat is soaked in the second material to form the polymer composite;
   further wherein the filler is arranged to respond to a stimulus so that the mechanical properties of the polymer composite change.

2. The polymer composite of claim 1, wherein the first material is poly(vinyl alcohol).

3. The polymer composite of claim 1, wherein the second material is ethylene oxide-epichlorohydrin 1:1 copolymer.

4. The polymer composite of claim 1, wherein the filler is about four percent by weight of the polymer composite.

5. The polymer composite of claim 1, wherein the filler can be arranged so that the tensile storage modulus of the polymer composite changes in response to the filler being exposed to a stimulus.

6. The polymer composite of claim 1, wherein the filler can be arranged so that the transparency of the polymer composite changes in response to the filler being exposed to a stimulus.

7. The polymer composite of claim 1, wherein the filler can be arranged so that the shape memory of the polymer composite changes in response to the filler being exposed to a stimulus.

* * * * *